US008653278B2

(12) United States Patent
Kozikowski et al.

(10) Patent No.: US 8,653,278 B2
(45) Date of Patent: Feb. 18, 2014

(54) ISOFORM SELECTIVE HDAC INHIBITORS

(75) Inventors: Alan P. Kozikowski, Chicago, IL (US); Mira Jung, Rockville, MD (US); Anatoly Dritschilo, Bethesda, MD (US); Arsen Gaysin, Berwyn, IL (US); Pavel A. Petukhov, Naperville, IL (US); Werner Tueckmantel, Yorktown Heights, NY (US); Hongbin Yuan, San Diego, CA (US); Yufeng Chen, Jinhua (CN)

(73) Assignees: Georgetown University, Washington, DC (US); The Board of Trustees of the University of Illinois, Urbana, IL (US)

( * ) Notice: Subject to any disclaimer, the term of this patent is extended or adjusted under 35 U.S.C. 154(b) by 78 days.

(21) Appl. No.: 12/375,348

(22) PCT Filed: Aug. 2, 2007

(86) PCT No.: PCT/US2007/017205
§ 371 (c)(1), (2), (4) Date: Mar. 26, 2010

(87) PCT Pub. No.: WO2008/019025
PCT Pub. Date: Feb. 14, 2008

(65) Prior Publication Data
US 2010/0196502 A1 Aug. 5, 2010

Related U.S. Application Data

(60) Provisional application No. 60/835,259, filed on Aug. 3, 2006, provisional application No. 60/853,928, filed on Oct. 24, 2006, provisional application No. 60/835,616, filed on Aug. 4, 2006.

(51) Int. Cl.
C07D 277/04 (2006.01)
(52) U.S. Cl.
USPC ............ 548/146; 548/182; 548/184; 548/185
(58) Field of Classification Search
USPC .................. 548/146, 182, 184, 185
See application file for complete search history.

(56) References Cited

U.S. PATENT DOCUMENTS

| 2002/0103192 A1 | 8/2002 | Curtin et al. |
| 2002/0177594 A1 | 11/2002 | Curtin et al. |
| 2005/0014839 A1 | 1/2005 | Kozikowski et al. |
| 2006/0047123 A1 | 3/2006 | Ahmed et al. |

FOREIGN PATENT DOCUMENTS

| WO | WO-02/26696 A1 | 4/2002 |
| WO | WO-02/46129 A2 | 6/2002 |
| WO | WO-2008/019025 A2 | 2/2008 |
| WO | WO-2008/019025 A3 | 2/2008 |

OTHER PUBLICATIONS

Patani et al., Chem Rev, 1996, vol. 96 (8), especially p. 3147.*
Glaser, et al., "Differential protein acetylation induced by novel histone deacetylase inhibitors," Biochemical and Biophysical Research Communications, 325 (2004), pp. 683-690.*
Kozikowski, et al., J. Med. Chem., 2007, 50(13), 3054-3061 (published Jun. 1, 2007).*
Glaser, et al., Biochemical and Biophysical Research Communications, 2004, v.325, pp. 683-690.*
Patani et al., Chem Rev, 1996, vol. 96 (8), especially p. 3149.*
Glaser, et al., Biochemical and Biophysical Research Communications, 325, 2004, pp. 683-690.*
Jung, M., et al., "Rational Design and Development of Radiation-Sensitizing Histone Deacetylase Inhibitors", *Chemistry & Biodiversity*, 2(11):1452-1461 (2005).
Kozikowski, A. P. et al., "Functional Differences in Epigenetic Modulators—Superiority of Mercaptoacetamide-Based Histone Deacetylase Inhibitors Relative to Hydroxamates in Cortical Neuron Neuroprotection Studies", *J. Med. Chem.*, 50(13):3054-3061 (Jun. 28, 2007).
Supplementary European Search Report from PCT/US2007/017205 dated Nov. 9, 2010.
Glaser, K. B. et al., "Differential protein acetylation induced by novel histone deacetylase inhibitors", *Biochemical and Biophysical Research Communications*, 325:683-690 (Elsevier, Inc., 2004).
Lavoie, R. et al., "Design and Synthesis of a Novel Class of Histone Deacetylase Inhibitors", *Bioorganic and Medicinal Chemistry Letters*, 11:2847-2850 (Elsevier Science Ltd., 2001).
Moradei, O. et al., "Histone Deacetylase Inhibitors: Latest Developments, Trends and Prospects", *Curr. Med. Chem. - Anti-Cancer Agents*, 5:529-560 (Bentham Science Publishers Ltd., 2005).
International Search Report for PCT/US07/17205 mailed May 21, 2008.

* cited by examiner

Primary Examiner — Susannah Chung
(74) Attorney, Agent, or Firm — Alan W. Steele; Foley Hoag LLP

(57) ABSTRACT

One aspect of the invention relates to isoform-selective HDAC inhibitors. Also provided are methods of sensitizing a cancer cell to the cytotoxic effects of radiotherapy. The invention also provides methods for treating cancer, methods for treating neurological diseases and methods for treating malaria. Additionally, the invention provides pharmaceutical compositions comprising an HDAC inhibitor of the invention; and kits comprising an HDAC inhibitor of the invention.

10 Claims, 22 Drawing Sheets

| Compound Number | R | HDAC Inhibition (IC$_{50}$) |
|---|---|---|
| 7a | −NH−C(O)−CH$_2$−NH$_2$ | 200 nM |
| 7b | −NH−C(O)−CH(NH$_2$)−CH$_2$−Ph | 80 nM |
| 7c | −NH−C(O)−pyrrolidinyl | 80 nM |
| 7d | −NH−C(O)−CH(NH$_2$)−CH$_2$−(indol-3-yl) | 50 nM |
| 7e | −NH−C(O)−CH(NH$_2$)−CH$_2$−(4-hydroxyphenyl) | 30 nM |
| 7f | −NH$_2$ | 80 nM |
| 25 | −H | 55 nM |

| Compound Number | R | HDAC Inhibition (IC$_{50}$) |
|---|---|---|
| 10a | -NH-C(O)-CH$_2$-NH$_2$ | 3 μM |
| 10b | -NH-C(O)-CH(NH$_2$)-CH$_2$-Ph | 7 μM |
| 10c | -NH-C(O)-pyrrolidine | 1.5 μM |
| 10d | -NH-C(O)-CH(NH$_2$)-CH$_2$-(3-indolyl) | > 1 μM |
| 10e | -NH-C(O)-CH(NH$_2$)-CH$_2$-(4-hydroxyphenyl) | > 1 μM |

| Compound Number | R | HDAC Inhibition (IC$_{50}$) |
| --- | --- | --- |
| 16 | —NH$_2$ | 2% inhibition at 100 nM |
| 17 | —NO$_2$ | 40-50 nM |
| 26 | —H | 15 nM |

| Compound Number | R | HDAC Inhibition (IC$_{50}$) |
| --- | --- | --- |
| 19 | —NO$_2$ | 22 nM |
| 22 | —NH—C(=O)—O—CH$_3$ | 5 nM |
| 23 | —NH$_2$ | 8 nM |

Figure 9a

| Compound | IC$_{50}$ proliferation (μM) | | | |
| --- | --- | --- | --- | --- |
| | SQ20B | PC3 | MCF7 | HeLa |
| SAHA | 3 | 1 | 0.75 | 2 |
| 7a | 30 | 20 | 40 | 15 |
| 7b | 7 | 8 | 3 | 4.5 |
| 7c | 25 | 20 | 15 | ND |
| 7d | 60 | 20 | 27 | 30 |
| 7e | 36 | 8 | 9 | 20 |
| 7f | 0.28 | 4.5 | 1.5 | 0.75 |
| 10a | > 60 | > 60 | > 60 | ND |
| 10b | > 60 | 50 | > 60 | ND |
| 10c | > 60 | 55 | > 50 | ND |
| 19 | 0.1 | 0.8 | 2 | 0.8 |
| 22 | 0.2 | 0.1 | 0.4 | ND |
| 23 | 0.1 | 0.9 | 0.4 | 0.1 |
| 25 | 0.8 | 0.4 | 0.7 | 0.1 |
| 26 | 0.1 | 0.75 | 0.42 | 0.2 |

Figure 9b

| Compound | IC$_{50}$ proliferation (μM) | | | |
|---|---|---|---|---|
| | SCC-35 | DU145 | MCF7/ADR | MDA-231 |
| 7f | 2.58 | 0.18 | 10 | 1 |
| 26 | 0.28 | 0.19 | 0.4 | < 0.4 |
| 22 | 0.19 | 0.52 | ND | ND |
| 25 | 0.1 | 0.58 | 0.35 | < 0.4 |
| 23 | 0.1 | 0.32 | 3 | < 0.4 |
| 19 | 0.38 | 0.32 | 3 | < 0.4 |

| Compound | IC$_{50}$ proliferation (μM) | | |
|---|---|---|---|
| | NHP-5 | MCF10A | Hs-68 |
| 7b | 80 | 100 | > 300 |
| 7d | 100 | > 100 | > 300 |
| 7e | 100 | > 100 | > 300 |

Figure 10

| Compound (0.5 μM) | HDAC activity remaining (%) | | | |
|---|---|---|---|---|
| | HDAC1[a] | HDAC2[a] | HDAC3[a] | HDAC8[b] |
| SAHA | 12.2 | 16.8 | 21.0 | 63.3 |
| TSA | 2.3 | 3.0 | 32.5 | 48.2 |
| 7a | 25.8 | 37.0 | 15.1 | 57.4 |
| 7b | 56.3 | 71.5 | 53.6 | 36.2 |
| 7c | 14.7 | 24.1 | 47.7 | 72.2 |
| 7d | 11.3 | 49.5 | 70.3 | 30.3 |
| 7e | 29.1 | 38.5 | 63.9 | 43.4 |
| 7f | 7.01 | 10.0 | 48.8 | 24 |
| 10a | 54.2 | 66.0 | 84.6 | 80.3 |
| 10b | 80.7 | 90.8 | 65.8 | 92.9 |
| 10c | 83.3 | 81.3 | 67.5 | 98.2 |
| 19 | 0.4 | 1.0 | 34.8 | 33 |
| 22 | 11.7 | 16.5 | 25.6 | 56.2 |
| 23 | 1.0 | 0.4 | 38.5 | 45 |
| 25 | 6.0 | 7.0 | 50.4 | 52 |
| 26 | 1.0 | 0.4 | 36.5 | 55 |

27

| HDAC Inhibition (IC$_{50}$) | IC$_{50}$ proliferation (μM) | | | |
|---|---|---|---|---|
| | SQ20B | PC3 | MCF7 | HeLa |
| 100 nM | > 60 | > 30 | 40 | ND |

28

| HDAC Inhibition (IC$_{50}$) | IC$_{50}$ proliferation (μM) | | | |
|---|---|---|---|---|
| | SQ20B | PC3 | MCF7 | HeLa |
| 300 nM | 15 | 10 | 9 | ND |

Figure 18

| Class | Examples |
|---|---|
| Sensitive | HB3, 3D7 |
| Resistant sensitized by Verapamil | FCB, DD2, V1/S, FCR-3 |
| Resistant but not sensitized by Verapamil | 7G8 |

[A]

| Strain Orgin | AGT = 26 (nM) | Y88 = 23 (nM) | Y90 = 19 (nM) |
|---|---|---|---|
| 7G8 Brazil | 8 | 0.175 | 10 |
| DD2 Indochina | 6 | 0.6 | 12 |
| FCR-3 Gambia | 12 | 0.6 | 22 |
| 3D7 Netherlands | 15 | 1.25 | 30 |
| HB3 Honduras | ND | 0.9 | ND |

[B]

chloroquine (CQ)

| Strain | Origin | IC$_{50}$-K2 (nM) |
|---|---|---|
| FCB | Colombia | 125 |
| HB3 | Honduras | 250 |
| 7G8 | Brazil | 300 |
| 3D7 | ? | 450 |
| DD2 | Thailand | 185 |
| V1/S | Vietnam | 250 |
| FCR-3 | Gambia | 175 |

[A]

| Strain | IC$_{50}$-CQ (nM) | IC$_{50}$-CQ+ K2 (nM) | Fold change |
|---|---|---|---|
| FCB | 325 | 60 | 5.5 |
| DD2 | 150 | 40 | 3.5 |

[B]

ISOFORM SELECTIVE HDAC INHIBITORS

RELATED APPLICATIONS

This application is a §371 national stage application of Patent Cooperation Treaty Application number PCT/US2007/017205, filed Aug. 2, 2007; which claims the benefit of priority to U.S. Provisional Patent Application Ser. No. 60/835,259; filed Aug. 3, 2006; U.S. Provisional Patent Application Ser. No. 60/835,616; filed Aug. 4, 2006; and U.S. Provisional Patent Application Ser. No. 60/853,928; filed Oct. 24, 2006; all of which are hereby expressly incorporated by reference in their entireties.

GOVERNMENT SUPPORT

This invention was made with support provided by the Department of Defense (Grant No. PC030471), and the National Cancer Institute (Grant No. P02 CA74175); therefore, the government has certain rights in the invention.

BACKGROUND OF THE INVENTION

Inhibitors of histone deacetylases (HDAC) have been shown to modulate transcription and to induce cell growth arrest, differentiation and apoptosis. HDAC inhibitors also enhance the cytotoxic effects of therapeutic agents used in cancer treatment, including radiation and chemotherapeutic drugs. Marks, P., Rifkind, R. A., Richon, V. M., Breslow, R., Miller, T., Kelly, W. K. Histone deacetylases and cancer: causes and therapies. *Nat Rev Cancer*, 1, 194-202, (2001); and Marks, P. A., Richon, V. M., Miller, T., Kelly, W. K. Histone deacetylase inhibitors. *Adv Cancer Res*, 91, 137-168, (2004). Moreover, recent evidence indicates that transcriptional dysregulation may contribute to the molecular pathogenesis of certain neurodegenerative disorders, such as Huntington's disease, spinal muscular atrophy, amyotropic lateral sclerosis, and ischemia. Langley, B., Gensert, J. M., Beal, M. F., Ratan, R. R. Remodeling chromatin and stress resistance in the central nervous system: histone deacetylase inhibitors as novel and broadly effective neuroprotective agents. *Curr Drug Targets CNS Neurol Disord*, 4, 41-50, (2005). For example, suberoylanilide hydroxamic acid (SAHA) has been shown to penetrate into the brain, and to improve dramatically the motor impairment in a mouse model of Huntington's disease, thus validating the pursuit of this class of molecules in the treatment of neurodegenerative diseases. Hockly, E., Richon, V. M., Woodman, B., Smith, D. L., Zhou, X., Rosa, E., Sathasivam, K., Ghazi-Noori, S., Mahal, A., Lowden, P. A., Steffan, J. S., Marsh, J. L., Thompson, L. M., Lewis, C. M., Marks, P. A., Bates, G. P. Suberoylanilide hydroxamic acid, a histone deacetylase inhibitor, ameliorates motor deficits in a mouse model of Huntington's disease. *Proc Natl Acad Sci USA*, 100, 2041-2046, (2003). A recent review has summarized the evidence that aberrant histone acetyltransferase (HAT) and histone deacetylases (HDAC) activity may represent a common underlying mechanism contributing to neurodegeneration. Moreover, using a mouse model of depression, Nestler has recently highlighted the therapeutic potential of histone deacetylation inhibitors (HDAC5) in depression. Tsankova, N. M., Berton, O., Renthal, W., Kumar, A., Neve, R. L., Nestler, E. J. Sustained hippocampal chromatin regulation in a mouse model of depression and antidepressant action. *Nat Neurosci*, 9, 519-525, (2006).

Thus, the potential of HDAC inhibitors is tremendous, but the translation of these ideas to the clinic will likely require the design of isoform selective molecules to minimize side effect issues. While several HDAC inhibitors are now in the clinic, most of these do not show significant selectivity for the individual HDAC isoforms, of which eleven are currently known that operate by zinc dependent mechanisms (class I includes HDACS 1, 2, 3, 8, and 11) and class II includes 4, 5, 6, 7, 9, and 10). Hu, E., Dul, E., Sung, C. M., Chen, Z., Kirkpatrick, R., Zhang, G. F., Johanson, K., Liu, R., Lago, A., Hofmann, G., Macarron, R., de los Frailes, M., Perez, P., Krawiec, J., Winkler, J., Jaye, M. Identification of novel isoform-selective inhibitors within class I histone deacetylases. *J Pharmacol Exp Ther*, 307, 720-728, (2003). Recently, it has been suggested that the non-sirtuin HDACs can be divided into three equally distinct groups with the third class comprised of proteins related to the human HDAC11 gene. Gregoretti, I. V., Lee, Y. M., Goodson, H. V. Molecular evolution of the histone deacetylase family: functional implications of phylogenetic analysis. *J Mol Biol*, 338, 17-31, (2004).

Class I enzymes (HDACs 1, 2, 3 and 8) range in size from 42-55 kDa, and are homologs of yeast Rpd3. They are ubiquitously expressed, predominantly nuclear and mainly function as transcriptional corepressors. Class II enzymes (HDACs 4, 5, 6, 7, 9 and 10) range in size from 120-160 kDa are homologs of yeast Hda1. Their distribution is tissue specific, suggesting distinct functions in cellular differentiation and developmental processes. Finally, as mentioned above, HDAC 11 is another recently identified member of the HDAC family that bears low similarities with HDAC class I and class II and therefore could not be definitively classified in either class.

In order to learn more about the role that the individual HDACs play in cell growth and/or differentiation, neuroprotection, and apoptosis, it is important to develop agents showing selectivity for individual isoforms or a small subset of these isoforms. While some degree of isoform selectivity has been shown by a few compounds, this problem of identifying selective inhibitors is far from solved, and the problem is complicated by the interactions of the HDACs with each other as well as other proteins (cofactors) that can possibly alter their interaction with various inhibitors. Glaser, K. B., Li, J., Pease, L. J., Staver, M. J., Marcotte, P. A., Guo, J., Frey, R. R., Garland, R. B., Heyman, H. R., Wada, C. K., Vasudevan, A., Michaelides, M. R., Davidson, S. K., Curtin, M. L. Differential protein acetylation induced by novel histone deacetylase inhibitors. *Biochem Biophys Res Commun*, 325, 683-690, (2004). However, experimental evidence shows that the different HDACs may have intrinsic differences in substrate specificity. Hildmann, C., Wegener, D., Riester, D., Hempel, R., Schober, A., Merana, J., Giurato, L., Guccione, S., Nielsen, T. K., Ficner, R., Schwienhorst, A. Substrate and inhibitor specificity of class 1 and class 2 histone deacetylases. *J Biotechnol*, 124, 258-70, (2006).

In addition to the need for HDAC inhibitors in the treatment of cancer and neurological disorders (see for example US Patent Applications 2005/0014839 and 2005/0032831; both of which are hereby incorporated by reference) there is a significant need in the art for novel compounds which show HDAC isoform selectivity.

SUMMARY OF THE INVENTION

Aspects of the present invention relate to HDAC inhibitors, pharmaceutical compositions comprising an HDAC inhibitor, and methods for treating disease (e.g., malaria, cancer or a neurological disease) comprising administering an HDAC inhibitor to a subject in need thereof. In certain embodiments the inhibitors show selectivity for certain HDAC isoforms.

One aspect of the invention relates to compounds represented by X-Y-L, or a pharmaceutically acceptable salt, solvate, derivative or prodrug thereof, wherein X is

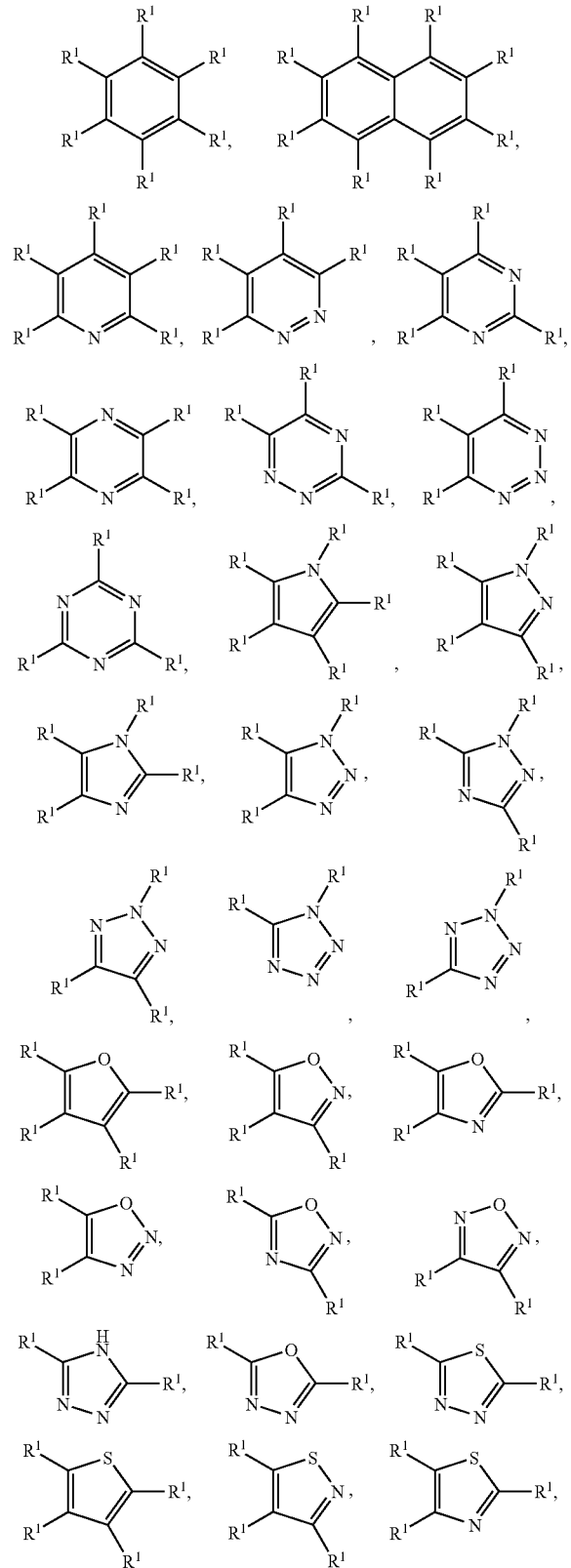

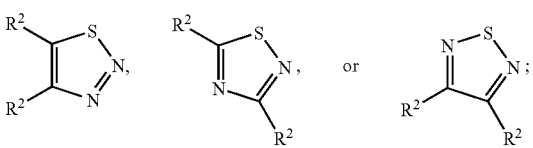

$R^1$ is, independently for each occurrence, a bond to W, a bond to Y, hydrogen, halo, azido, alkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano, or —$(CR_2)_pR$; or any two vicinal $R^1$ taken, together are a bidentate substituent which form, in addition to the atoms to which they are bound, a five-, six- or seven-membered, carbocyclic or heterocyclic, aromatic or non-aromatic, ring, which is optionally substituted with one to four R; provided that one $R^1$ is a bond to W and one $R^1$ is a bond to Y; R is, independently for each occurrence, hydrogen, halo, azido, alkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, or isocyano; p is, independently for each occurrence, 0-10 inclusive; W is —$(CH_2)_qT$, —$(CH_2)_qOT$, —$(CH_2)_qN(H)T$, —$(CH_2)_qST$, —$(CH_2)_qC(=O)T$, —$(CH_2)_qC(=NH)T$, —$(CH_2)_qC(=S)T$, —$(CH_2)_qOC(=O)T$, —$(CH_2)_qOC(=NH)T$, —$(CH_2)_qOC(=S)T$, —$(CH_2)_qC(=O)OT$, —$(CH_2)_qC(=NH)OT$, —$(CH_2)_qC(=S)OT$, —$(CH_2)_qN(H)C(=O)T$, —$(CH_2)_qN(H)C(=NH)T$, —$(CH_2)_qN(H)C(=S)T$, —$(CH_2)_qC(=O)N(H)T$, —$(CH_2)_qC(=NH)N(H)T$, —$(CH_2)_qC(=S)N(H)T$, —$(CH_2)_qSC(=O)T$, —$(CH_2)_qSC(=NH)T$, —$(CH_2)_qSC(=S)T$, —$(CH_2)_qC(=O)ST$, —$(CH_2)_qC(=NH)ST$, —$(CH_2)_qC(=S)ST$, —$(CH_2)_qC(=O)CH(NH_2)T$, —$(CH_2)_qN(H)C(=O)CH(NH_2)T$, —$(CH_2)_qOC(=O)CH(NH_2)T$, or —$(CH_2)_qSC(=O)CH(NH_2)T$; T is hydrogen, alkyl, fluoroalkyl, perfluoroalkyl, aralkyl, alkenyl, alkynyl, cycloalkyl, heterocyclyl, aryl, heteroaryl, aralkyl, heteroaralkyl, or —$(CR_2)_pR$; q is 0-3 inclusive; Y is a bond between X and L, or

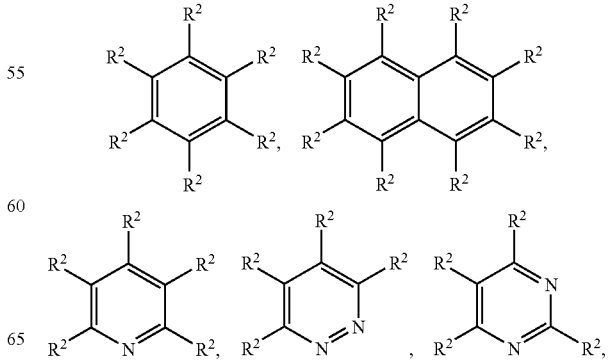

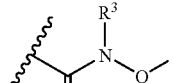

R² is, independently for each occurrence, a bond to X, a bond to L, hydrogen, halo, azido, alkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfa, sulfonate, sulfonyl, sulfonamido, formyl, cyano, isocyano, or —(CR₂)ₚR; or any two vicinal R² taken together are a bidentate substituent which form, in addition to the atoms to which they are bound, a five-, six- or seven-membered, carbocyclic or heterocyclic, aromatic or non-aromatic, ring, which is optionally substituted with one to four R; provided that one R² is a bond to X and one R² is a bond to L; L is -(Q¹)-CH₂-(Q²)-Z, -(Q¹)ₘ-O-(Q²)-Z, -(Q¹)-N(H)-(Q²)-Z, -(Q²)-S-(Q²)-Z, -(Q¹)-C(=O)-(Q²)-Z, -(Q¹)-C(=NH)-(Q²)-Z, -(Q¹)-C(=S)-(Q²)-Z, -(Q¹)-OC(=O)-(Q²)-Z, -(Q¹)-OC(=NH)-(Q²)-Z, -(Q¹)-OC(=S)-(Q²)-Z, -(Q¹)-N(H)C(=O)-(Q²)-Z, -(Q¹)-N(H)C(=NH)-(Q²)-Z, -(Q¹)-N(H)C(=S)-(Q²)-Z, -(Q¹)-SC(=O)-(Q²)-Z, -(Q¹)-SC(=NH)-(Q²)-Z, -(Q¹)-SC(=S)-(Q²)-Z, -(Q¹)-C(=O)O-(Q²)-Z, -(Q¹)-C(=NH)O-(Q²)-Z, -(Q¹)-C(=S)O-(Q²)-Z, -(Q¹)-C(=O)N(H)-(Q²)-Z, -(Q¹)-C(=NH)N(H)-(Q²)-Z, -(Q¹)-C(=S)N(H)-(Q²)-Z, -(Q¹)-OC(=O)O-(Q²)-Z, -(Q¹)-OC(=NH)O-(Q²)-Z, -(Q¹)-OC(=S)O-(Q²)-Z, -(Q¹)-N(H)C(=O)N(H)-(Q²)-Z, -(Q¹)-N(H)C(=NH)N(H)-(Q²)-Z, -(Q¹)-N(H)C(=S)N(H)-(Q²)-Z, -(Q¹)-OC(=O)N(H)-(Q²)-Z, -(Q¹)-OC(=NH)N(H)-(Q²)-Z, -(Q¹)-OC(=S)N(H)-(Q²)-Z, -(Q¹)-N(H)C(=O)-(Q²)-Z, -(Q¹)-N(H)C(=NH)O-(Q²)-Z, or -(Q¹)-N(H)C(=S)O-(Q²)-Z; Q¹ is C₁₋₁₀alkylene or a bond; Q² is C₁₋₁₀alkylene; Z is

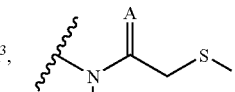

A is, independently for each occurrence, O, S, NR³ or absent; R³ is, independently for each occurrence, hydrogen, alkyl, aryl, aralkyl, or acyl; and R⁴ is, independently for each occurrence, hydrogen, halo, azido, alkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano, or —(CR$_2$)$_p$R; or any two vicinal R⁴ taken together are a bidentate substituent which form, in addition to the atoms to which they are bound, a five-, six- or seven-membered, carbocyclic or heterocyclic, aromatic or non-aromatic, ring, which is optionally substituted with one to four R. The present invention also relates to a pharmaceutical composition, comprising any of the aforementioned compounds; and a pharmaceutically acceptable excipient.

Another aspect of the present invention relates to a method for increasing the sensitivity of a cancer cell to the cytotoxic effects of radiotherapy, comprising contacting said cell with an effective amount of a compound of the invention. In certain embodiments, the cell is an in vivo cell. Another aspect of the present invention relates to a method for treating cancer, comprising administering to a subject in need thereof a therapeutically effective amount of a compound of the invention. In certain embodiments, said subject is a human.

Another aspect of the present invention relates to a method of treating Non-Hodgkin's lymphoma, Hodgkin's disease, Ewing's sarcoma, testicular cancer, prostate cancer, larynx cancer, cervical cancer, nasopharynx cancer, breast cancer, colon cancer, pancreatic cancer, head and neck cancer, esophageal cancer, rectal cancer, small-cell lung cancer, non-small cell lung cancer, brain cancer, or a CNS neoplasm, comprising administering to a subject in need thereof a therapeutically effective amount of a compound of the invention. In certain embodiments, said subject is a human.

In certain embodiments, any of the aforementioned methods further comprises administering to said subject a therapeutically effective amount of radiotherapy. In certain embodiments, said subject is a human.

The present invention also relates to a method for treating a neurological disease, comprising administering to a subject in need thereof a therapeutically effective amount of a compound of the invention. In certain embodiments, said subject is a human. The present invention also relates to a method for treating Huntington's disease, lupus, or schizophrenia, comprising administering to a subject in need thereof a therapeutically effective amount of a compound of the invention. In certain embodiments, said subject is a human.

The present invention also relates to a method for treating malaria, comprising administering to a subject in need thereof a therapeutically effective amount of an HDAC inhibitor of the invention. In certain embodiments, said subject is a human. In certain embodiments, said method further comprises co-administering an antimalarial compound (e.g., chloroquine).

BRIEF DESCRIPTION OF THE FIGURES

FIGS. 9a and 9b depict antiproliferation activities of suberoylanilide hydroxamic acid (SAHA), and various hydroxamates and mercaptoamides of the present invention. Note: ND is an abbreviation for "Not Determined."

FIG. 10 depicts the effect of HDAC inhibitors, including selected compounds of the invention, on Class I HDAC isoform activities. Note that (a) denotes that HeLa nuclear extracts were used for immunoprecipitation (IP) with antibodies against HDAC 1-3; and (b) denotes that recombinant protein was used for HDAC 8. Note: TSA is trichostatin A.

FIG. 11 further depicts (middle) the binding areas (BA) and grooves (G) formed by the BAs that are available for interaction with the HDACIs. (middle left) Ribbon model; (middle right) Solvent accessible surface of HDAC8 in complex with SAHA (PDB: 1T69). FIG. 11 also depicts (bottom) ligands 7a-e and SAHA docked to the binding site of HDAC8 (PDB:1T67): 7a—rose, 7b—green, 7c—blue, 7d—yellow, 7e—cyan, SAHA—magenta. The Zn atom is rendered as a sphere (magenta). The amino acids of HDAC8 interacting with the CAP groups of the ligands are shown as ball-and-stick models (grey).

FIG. 18 depicts [A] a table of the strains of *Plasmodium falciparum* (Pf) defined by chloroquine (CQ) resistance; and [B] a summary of the $IC_{50}$ values of selected compounds of the invention against these strains. Note that Verapamil has been reported to reverse chloroquine resistance in the human malaria parasite *Plasmodium falciparum* (Martin, S. K., Oduola, A. M. J., and Milhous, W. K. *Science* 1987, 235, 899-901).

FIG. 20 depicts [A] chloroquine (CQ) and K2 $IC_{50}$ values for geographically representative strains of *Plasmodium falciparum* (Pf); and [B] the observed $IC_{50}$ values of combinations of K2 and CQ.

DETAILED DESCRIPTION OF THE INVENTION

Selected Compounds of the Invention

Figure 1:
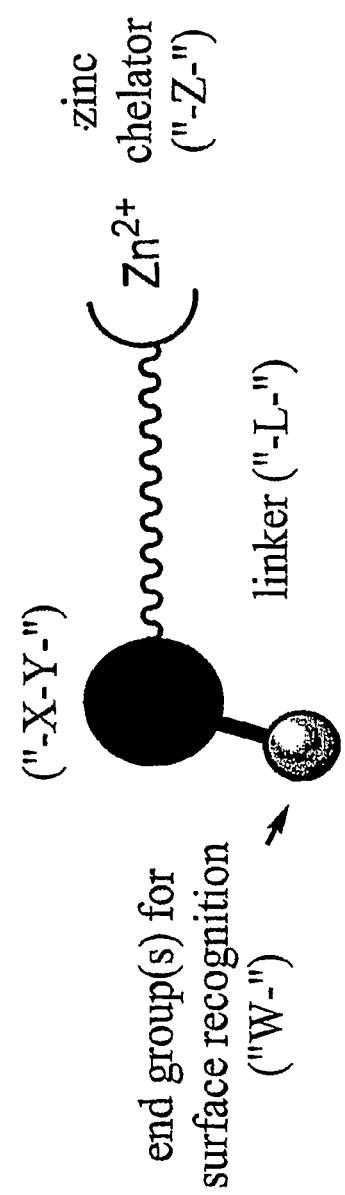
FIG. 1 depicts one embodiment of the histone deacetylase (HDAC) inhibitors of the invention, highlighting that these inhibitors are specifically designed for surface recognition.

One aspect of the invention relates to structurally unique histone deacetylases (HDAC) inhibitors in which an aryl or biaryl moiety (e.g., 2,4'-diaminobiphenyl or 3-phenylthiazole group), appropriately decorated with an amino acid residue, serves as a potential isoform differentiating, surface recognition element. The surface recognition group is connected through a linker to a zinc chelating moiety (e.g., a hydroxamate or a mercaptoacetamide group). In certain embodiments, different amino acids, as well as other structural motifs (e.g., carbohydrates) can be attached to the aryl or biaryl moiety in order to achieve discrimination among different HDAC isoforms. In some instances, a compound of the invention has one or more chiral centers. In these instances, it is to be understood that the invention encompasses all possible stereoisomers of these compounds.

One aspect of the present invention relates to a compound represented by X-Y-L, or a pharmaceutically acceptable salt, solvate, derivative or prodrug thereof, wherein:

X is 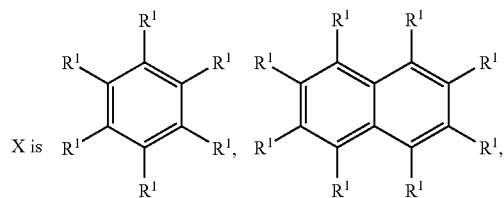

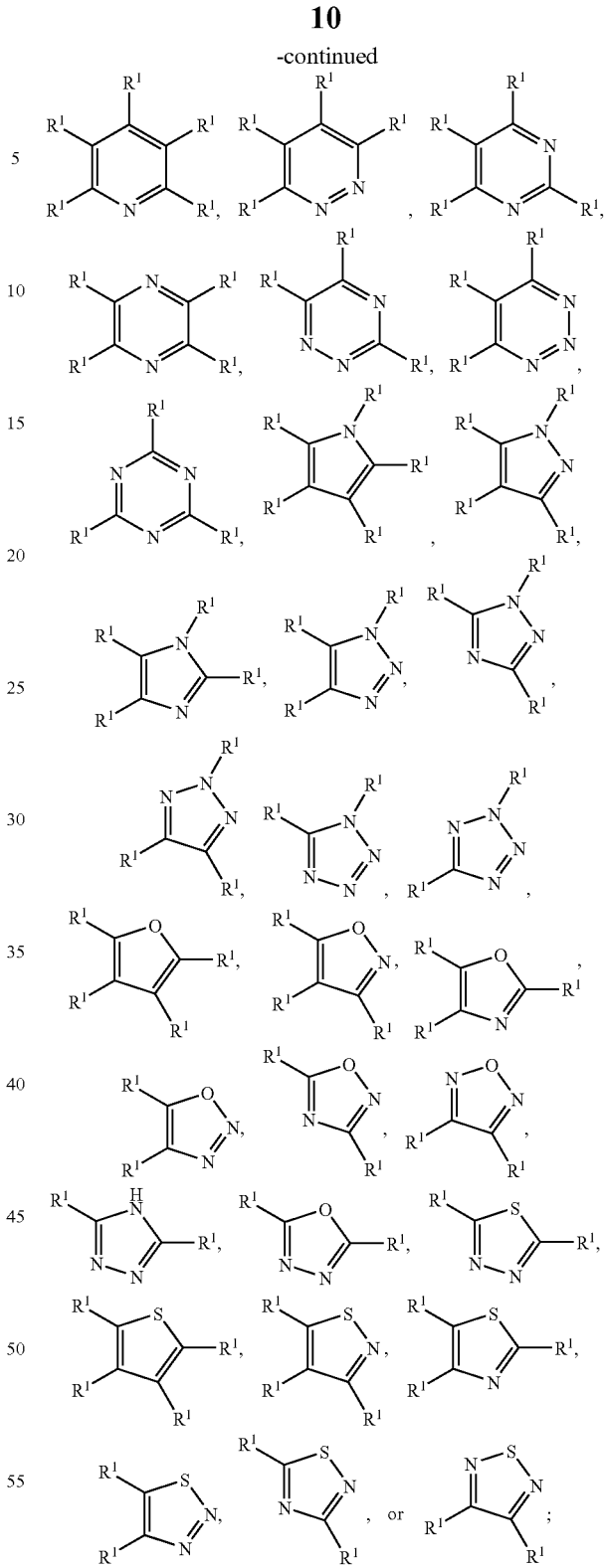

$R^1$ is, independently for each occurrence, a bond to W, a bond to Y, hydrogen, halo, azido, alkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano, or —$(CR_2)_pR$; or any two vicinal $R^1$ taken together are a bidentate substituent which form, in addition to the atoms to which they are bound, a five-, six- or seven-Membered, carbocyclic or heterocyclic, aromatic or non-aromatic, ring, which is optionally substituted with one to four R; provided that one $R^1$ is a bond to W and one $R^1$ is a bond to Y;

R is, independently for each occurrence, hydrogen, halo, azido, alkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, or isocyano;

p is, independently for each occurrence, 0-10 inclusive;

W is —$(CH_2)_qT$, —$(CH_2)_qOT$, —$(CH_2)_qN(H)T$, —$(CH_2)_qST$, —$(CH_2)_qC(=O)T$, —$(CH_2)_qC(=NH)T$, —$(CH_2)_qC(=S)T$, —$(CH_2)_qOC(=O)T$, —$(CH_2)_qC(=O)OT$, —$(CH_2)_qC(=NH)OT$, —$(CH_2)_qOC(=S)T$, —$(CH_2)_qC(=O)OT$, —$(CH_2)_qC(=NH)OT$, —$(CH_2)_qC(=S)OT$, —$(CH_2)_qN(H)C(=O)T$, —$(CH_2)_qN(H)C(=NH)T$, —$(CH_2)_qN(H)C(=S)T$, —$(CH_2)_qC(=O)N(H)T$, —$(CH_2)_qC(=NH)N(H)T$, —$(CH_2)_qC(=S)N(H)T$, —$(CH_2)_qSC(=O)T$, —$(CH_2)_qSC(=NH)T$, —$(CH_2)_qSC(=S)T$, —$(CH_2)_qC(=O)ST$, —$(CH_2)_qC(=NH)ST$, —$(CH_2)_qC(=S)ST$, —$(CH_2)_qC(=O)CH(NH_2)T$, —$(CH_2)_qN(H)C(=O)CH(NH_2)T$, —$(CH_2)_qOC(=O)CH(NH_2)T$, or —$(CH_2)_qSC(=O)CH(NH_2)T$;

T is hydrogen, alkyl, fluoroalkyl, perfluoroalkyl, aralkyl, alkenyl, alkynyl, cycloalkyl, heterocyclyl, aryl, heteroaryl, aralkyl, heteroaralkyl, or —$(CR_2)_pR$;

q is 0-3 inclusive;

Y is a bond between X and L, or

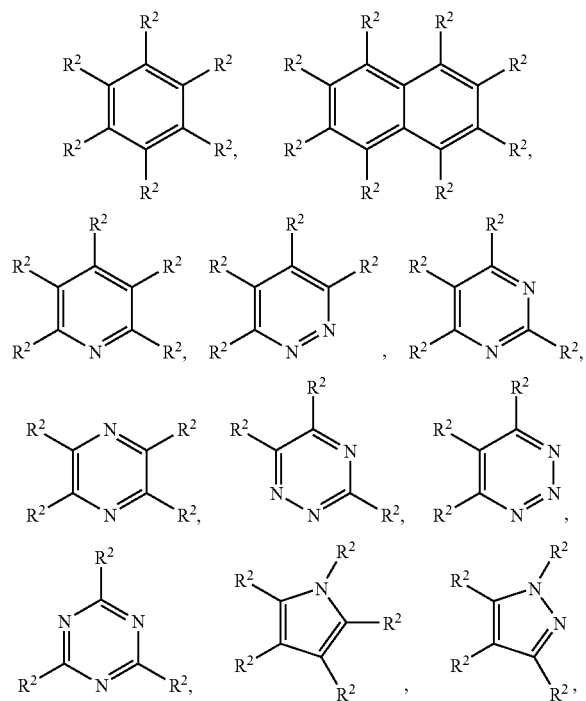

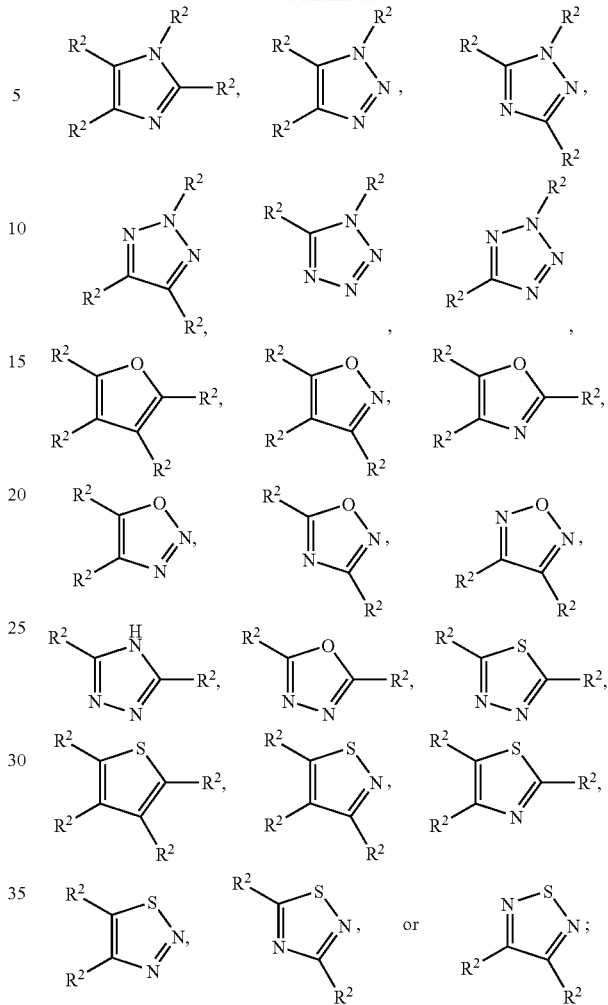

$R^2$ is, independently for each occurrence, a bond to X, a bond to L, hydrogen, halo, azido, alkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano, or —$(CR_2)_pR$; or any two vicinal $R^2$ taken together are a bidentate substituent which form, in addition to the atoms to which they are bound, a five-, six- or seven-membered, carbocyclic or heterocyclic, aromatic or non-aromatic, ring, which is optionally substituted with one to four R; provided that one $R^2$ is a bond to X and one $R^2$ is a bond to L;

L is -$(Q^1)$-$CH_2$-$(Q^2)$-Z, -$(Q^1)_m$-O-$(Q^2)$-Z, -$(Q^1)$—N(H)-$(Q^2)$-Z, -$(Q^1)$-S-$(Q^2)$-Z, -$(Q^1)$-C(=O)-$(Q^2)$-Z, -$(Q^1)$-C(=NH)-$(Q^2)$-Z, -$(Q^1)$-C(=S)-$(Q^2)$-Z, -$(Q^1)$-OC(=O)-$(Q^2)$-Z, -$(Q^1)$-OC(=NH)-$(Q^2)$-Z, -$(Q^1)$-OC(=S)-$(Q^2)$-Z, -$(Q^1)$-N(H)C(=O)-$(Q^2)$-Z, -$(Q^1)$-N(H)C(=NH)-$(Q^2)$-Z, -$(Q^1)$-N(H)C(=S)-$(Q^2)$-Z, -$(Q^1)$-SC(=O)-$(Q^2)$-Z, -$(Q^1)$-SC(=NH)-$(Q^2)$-Z, -$(Q^1)$-SC(=S)-$(Q^2)$-Z, -$(Q^1)$—C(=O)O-$(Q^2)$-Z, -$(Q^1)$-C(=NH)O-$(Q^2)$-Z, -$(Q^1)$-C(=S)O-$(Q^2)$-Z, -$(Q^1)$-C(=O)N(H)-$(Q^2)$-Z, -$(Q^1)$-C(=NH)N(H)-$(Q^2)$-Z, -$(Q^1)$-C(=S)N(H)-$(Q^2)$-Z, -$(Q^1)$-OC(=O)O-$(Q^2)$-Z, -$(Q^1)$-OC(=NH)O-$(Q^2)$-Z, -$(Q^1)$-OC(=S)O-$(Q^2)$-Z, -$(Q^1)$-N(H)

C(=O)N(H)-(Q²)-Z, -(Q¹)-N(H)C(=NH)N(H)-(Q²)-Z, -(O)-N(H)C(=S)N(H)-(Q²)-Z, -(Q¹)-OC(=O)N(H)-(Q²)-Z, -(Q¹)-OC(=NH)N(H)-(Q²)-Z, -(Q¹)-OC(=S)N(H)-(Q²)-Z, -(Q¹)-N(H)C(=O)O-(Q²)-Z, —(O—N(H)C(=NH)O-(Q²)-Z, or -(Q¹)-N(H)C(=S)O-(Q²)-Z;

Q¹ is $C_{1-10}$alkylene or a bond;
Q² is $C_{1-10}$alkylene;
Z is

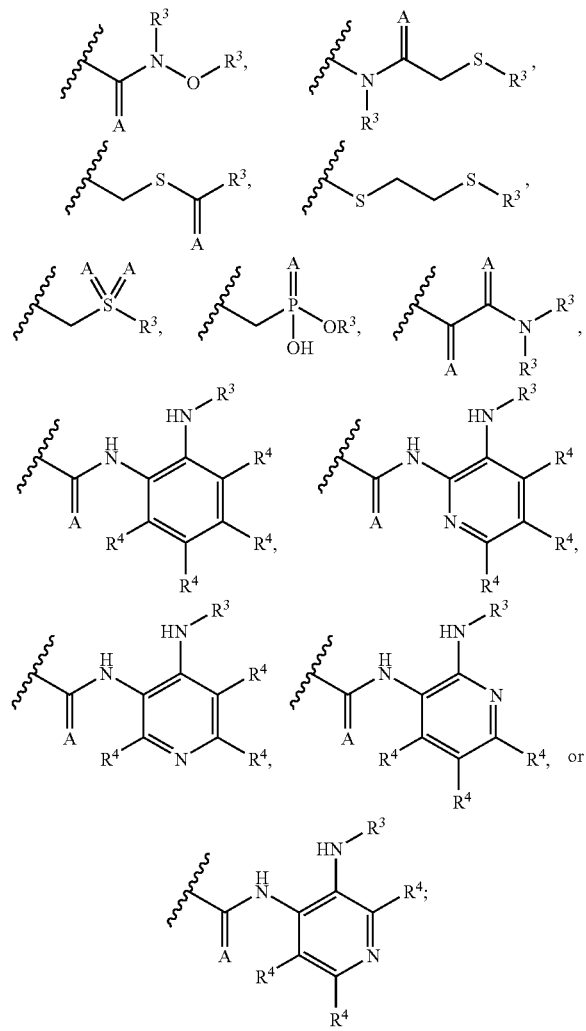

A is, independently for each occurrence, O, S, NR³ or absent;

R³ is, independently for each occurrence, hydrogen, alkyl, aryl, aralkyl, or acyl;

R⁴ is, independently for each occurrence, hydrogen, halo, azido, alkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano, or —(CR₂)$_p$R⁴; or any two vicinal R⁴ taken together are a bidentate substituent which form, in addition to the atoms to which they are bound, a five-, six- or seven-membered, carbocyclic or heterocyclic, aromatic or non-aromatic, ring, which is optionally substituted with one to four R; and the stereochemical configuration at any stereocenter is R, S, or a mixture of these configurations.

In certain embodiments, the present invention relates to the aforementioned compound, wherein X is

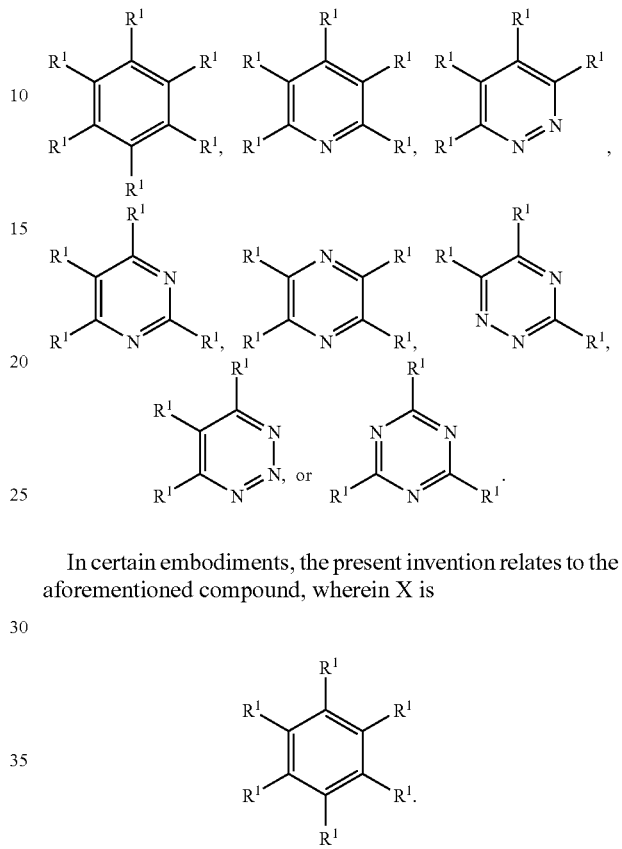

In certain embodiments, the present invention relates to the aforementioned compound, wherein X is In certain embodiments, the present invention relates to the aforementioned compound, wherein R¹ is, independently for each occurrence, a bond to W, a bond to Y, hydrogen, halo, azido, alkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano, or —(CR₂)$_p$R.

In certain embodiments, the present invention relates to the aforementioned compound, wherein R¹ is, independently for each occurrence, a bond to W, a bond to Y, hydrogen, halo, hydroxy, alkoxy, amino, alkylamino, or acylamino.

In certain embodiments, the present invention relates to the aforementioned compound, wherein R¹ is independently for each occurrence, a bond to W, a bond to Y, or hydrogen.

In certain embodiments, the present invention relates to the aforementioned compound, wherein provided that only one R¹ is a bond to W; and only one R¹ is a bond to Y.

In certain embodiments, the present invention relates to the aforementioned compound, wherein, wherein p is 0-3.

In certain embodiments, the present invention relates to the aforementioned compound, wherein p is 0.

In certain embodiments, the present invention relates to the aforementioned compound, wherein p is 1.

In certain embodiments, the present invention relates to the aforementioned compound, wherein p is 2.

In certain embodiments, the present invention relates to the aforementioned compound, wherein W is —(CH$_2$)$_q$T, —(CH$_2$)$_q$OT, —(CH$_2$)$_q$N(H)T, —(CH$_2$)$_q$ST, —(CH$_2$)$_q$C(=O)T, —(CH$_2$)$_q$OC(=O)T, —(CH$_2$)$_q$C(=O)OT, —(CH$_2$)$_q$N(H)C(=O)T, —(CH$_2$)$_q$C(=O)N(H)T, —(CH$_2$)$_q$C(=O)CH(NH$_2$)T, —(CH$_2$)$_q$N(H)C(=O)CH(NH$_2$)T, or —(CH$_2$)$_q$C(=O)CH(NH$_2$)T.

In certain embodiments, the present invention relates to the aforementioned compound, wherein W is —(CH$_2$)$_q$N(H)C(=O)CH(NH$_2$)T.

In certain embodiments, the present invention relates to the aforementioned compound, wherein q is 0.

In certain embodiments, the present invention relates to the aforementioned compound, wherein q is 1.

In certain embodiments, the present invention relates to the aforementioned compound, wherein Y is

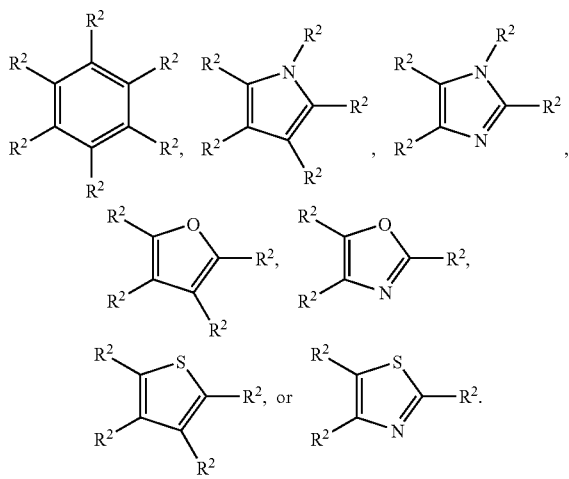

In certain embodiments, the present invention relates to the aforementioned compound, wherein Y is

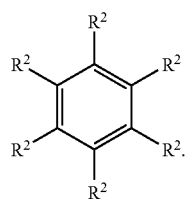

In certain embodiments, the present invention relates to the aforementioned compound, wherein Y is

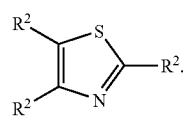

In certain embodiments, the present invention relates to the aforementioned compound, wherein R$^2$ is, independently for each occurrence, a bond to X, a bond to L, hydrogen, halo, azido, alkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano, or —(CR$_2$)$_p$R.

In certain embodiments, the present invention relates to the aforementioned compound, wherein R$^2$ is, independently for each occurrence, a bond to W, a bond to Y, hydrogen, halo, hydroxy, alkoxy, amino, alkylamino, or acylamino.

In certain embodiments, the present invention relates to the aforementioned compound, wherein R$^2$ is independently for each occurrence, a bond to W, a bond to Y, or hydrogen.

In certain embodiments, the present invention relates to the aforementioned compound, wherein provided that only one R$^2$ is a bond to X; and only one R$^2$ is a bond to Y.

In certain embodiments, the present invention relates to the aforementioned compound, wherein L is -(Q$^1$)-CH$_2$-(Q$^2$)-Z, -(Q$^1$)$_m$-O-(Q$^2$)-Z, -(Q$^1$)-N(H)-(Q$^2$)-Z, -(Q$^1$)-S-(Q$^2$)-Z, -(Q$^1$)-C(=O)-(Q$^2$)-Z, -(Q$^1$)-OC(=O)-(Q$^2$)-Z, -(Q$^1$)-N(H)C(=O)-(Q$^2$)-Z, -(Q$^1$)—C(=O)O-(Q$^2$)-Z, -(Q$^1$)-C(=O)N(H)-(Q$^2$)-Z, -(Q$^1$)-OC(=O)O-(Q$^2$)-Z, -(Q$^1$)-N(H)C(=O)N(H)-(Q$^2$)-Z, -(Q$^1$)-OC(=O)N(H)-(Q$^2$)-Z, or -(Q$^1$)-N(H)C(=O)O-(Q$^2$)-Z.

In certain embodiments, the present invention relates to the aforementioned compound, wherein Q$^1$ is a bond, —CH$_2$—, —CH$_2$CH$_2$—, or —CH$_2$CH$_2$CH$_2$—.

In certain embodiments, the present invention relates to the aforementioned compound, wherein, Q$^2$ is C$_{3-6}$alkylene.

In certain embodiments, the present invention relates to the aforementioned compound, wherein Q$^2$ is —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, or —CH$_2$CH$_2$CH$_2$CH$_2$H$_2$CH$_2$CH$_2$—.

In certain embodiments, the present invention relates to the aforementioned compound, wherein Z is

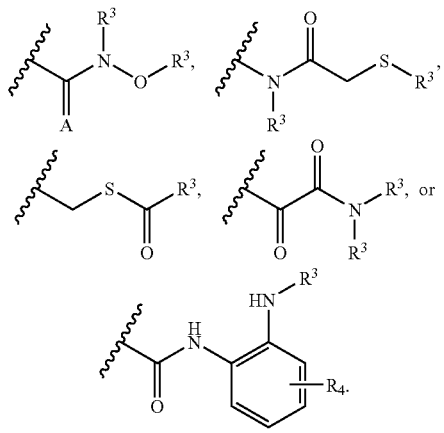

In certain embodiments, the present invention relates to the aforementioned compound, wherein Z is

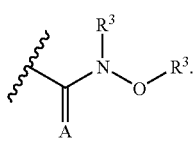

In certain embodiments, the present invention relates to the aforementioned compound, wherein Z is

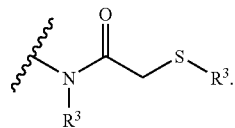

In certain embodiments, the present invention relates to the aforementioned compound, wherein A is O.

In certain embodiments, the present invention relates to the aforementioned compound, wherein $R^3$ is hydrogen.

In certain embodiments, the present invention relates to the aforementioned compound, wherein $R^4$ is independently for each occurrence, hydrogen, halo, azido, alkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano, or —$(CR_2)_pR$.

In certain embodiments, the present invention relates to the aforementioned compound, wherein $R^4$ is hydrogen.

In certain embodiments, the present invention relates to the aforementioned compound, wherein $R^3$ is hydrogen; and $R^4$ is hydrogen.

In another embodiment the invention relates to a compound, or a pharmaceutically acceptable salt, solvate, derivative or prodrug thereof, selected from the group consisting of

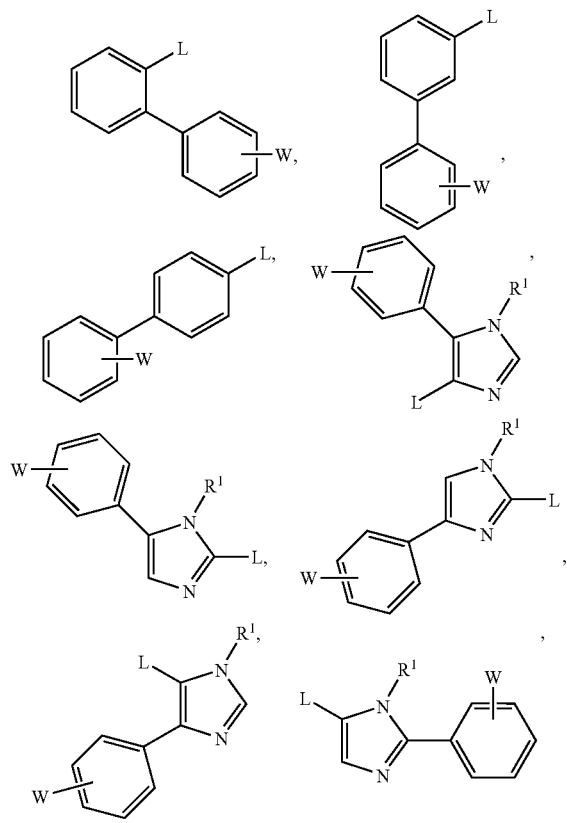

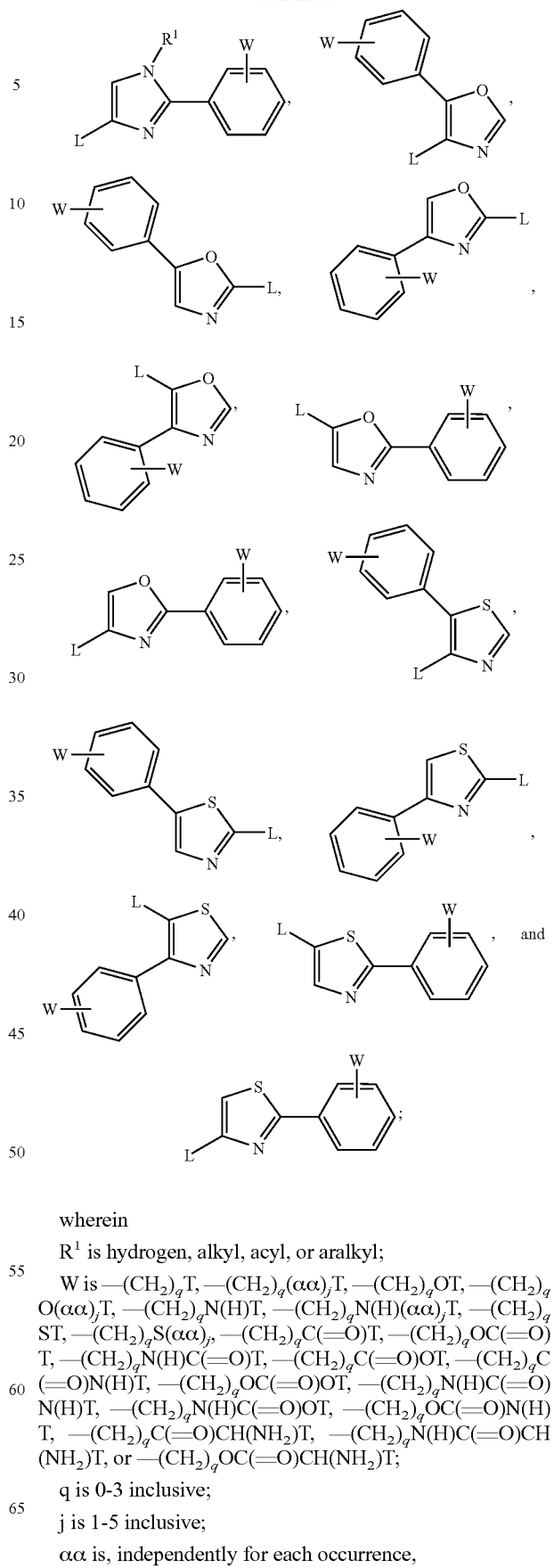

wherein $R^1$ is hydrogen, alkyl, acyl, or aralkyl;

W is —$(CH_2)_qT$, —$(CH_2)_q(\alpha\alpha)_jT$, —$(CH_2)_qOT$, —$(CH_2)_qO(\alpha\alpha)_jT$, —$(CH_2)_qN(H)T$, —$(CH_2)_qN(H)(\alpha\alpha)_jT$, —$(CH_2)_qST$, —$(CH_2)_qS(\alpha\alpha)_j$, —$(CH_2)_qC(=O)T$, —$(CH_2)_qOC(=O)T$, —$(CH_2)_qN(H)C(=O)T$, —$(CH_2)_qC(=O)OT$, —$(CH_2)_qC(=O)N(H)T$, —$(CH_2)_qOC(=O)OT$, —$(CH_2)_qN(H)C(=O)N(H)T$, —$(CH_2)_qN(H)C(=O)OT$, —$(CH_2)_qOC(=O)N(H)T$, —$(CH_2)_qC(=O)CH(NH_2)T$, —$(CH_2)_qN(H)C(=O)CH(NH_2)T$, or —$(CH_2)_qOC(=O)CH(NH_2)T$;

q is 0-3 inclusive;

j is 1-5 inclusive;

αα is, independently for each occurrence,

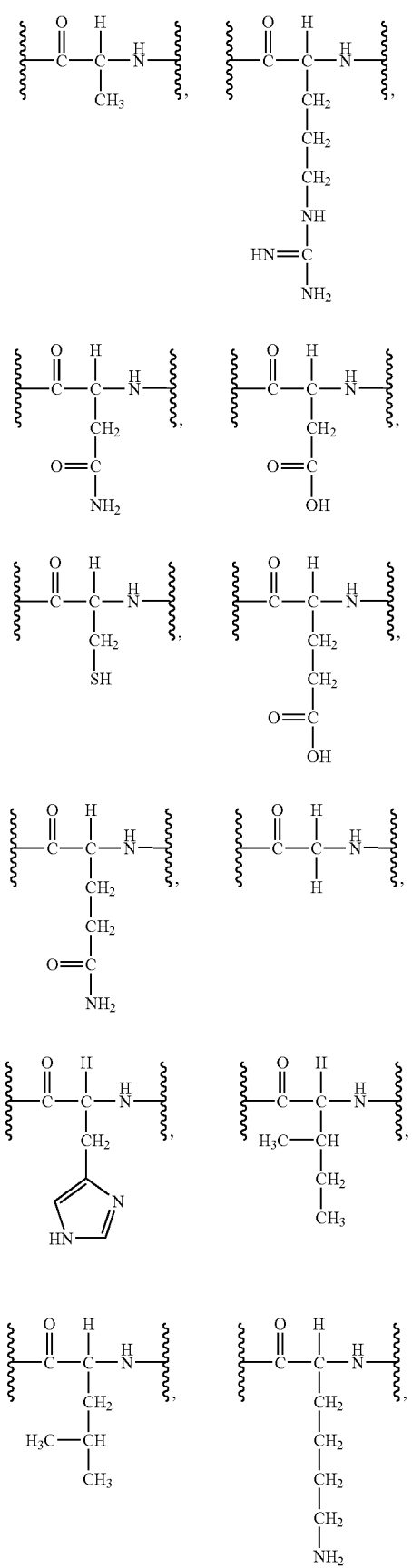

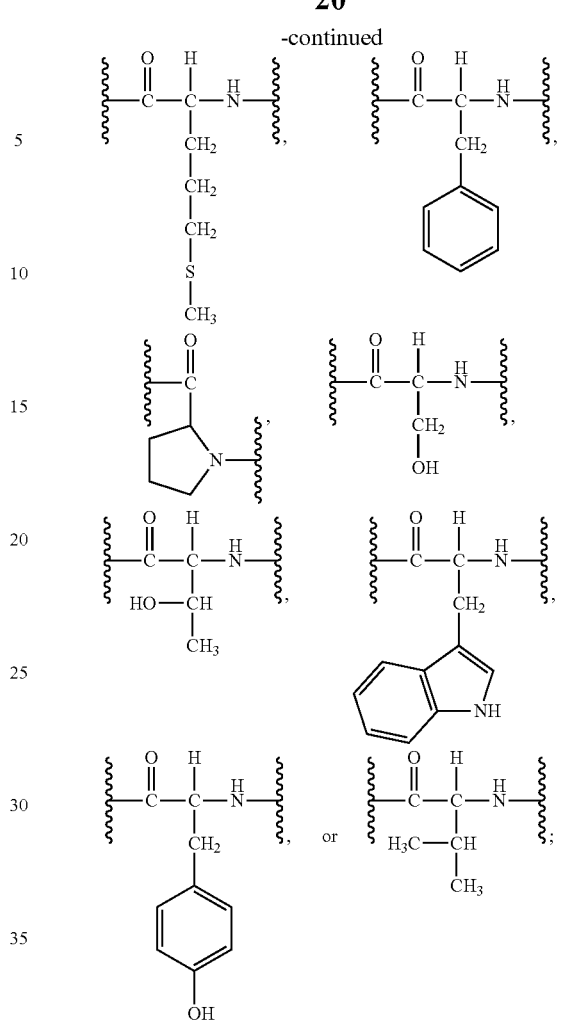

T is hydrogen, alkyl, fluoroalkyl, perfluoroalkyl, aralkyl, alkenyl, alkynyl, cycloalkyl, heterocyclyl, aryl, heteroaryl, aralkyl, heteroaralkyl, or —$(CR_2)_pR$;

R is, independently for each occurrence, hydrogen, halo, azido, alkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, or isocyano;

p is, independently for each occurrence, 0-5 inclusive;

L is -$(Q^1)$-$CH_2$-$(Q^2)$-Z, -$(Q^1)_m$-O-$(Q^2)$-Z, -$(Q^1)$-N(H)-$(Q^2)$-Z, -$(Q^1)$-C(=O)-$(Q^2)$-Z, -$(Q^1)$-OC(=O)-$(Q^2)$-Z, -$(Q^1)$-N(H)C(=O)-$(Q^2)$-Z, -$(Q^1)$-C(=O)O-$(Q^2)$-Z, or -$(Q^1)$-C(=O)N(H)-$(Q^2)$-Z;

$Q^1$ is $C_{1-3}$alkylene or a bond;
$Q^2$ is $C_{1-10}$alkylene;
Z is

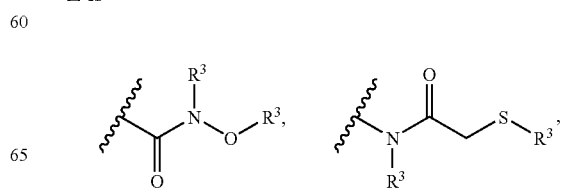

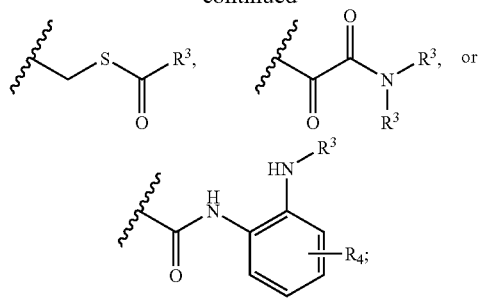

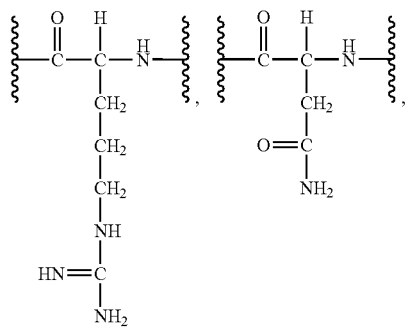

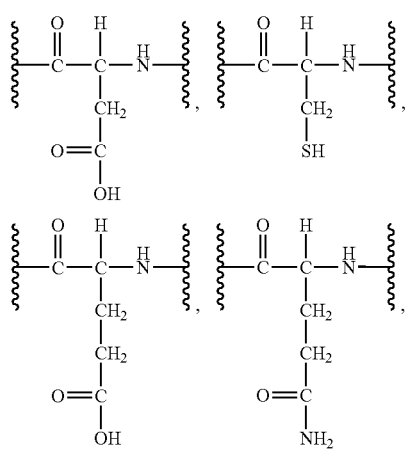

R³ is, independently for each occurrence, hydrogen, alkyl, aryl, aralkyl, or acyl;

R⁴ is hydrogen, halo, azido, alkyl, fluoroalkyl, perfluoroalkyl, aralkyl, alkynyl, cycloalkyl, heterocyclyl, aryl, heteroaryl, aralkyl, heteroaralkyl, hydroxy, alkoxy, aryloxy, heteroaryloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano, or —(CR₂)$_p$R; and the stereochemical configuration at any stereocenter is R, S, or a mixture of these configurations.

In certain embodiments, the present invention relates to the aforementioned compound, wherein said compound, or a pharmaceutically acceptable salt, solvate, derivative or prodrug thereof, is selected from the group consisting of

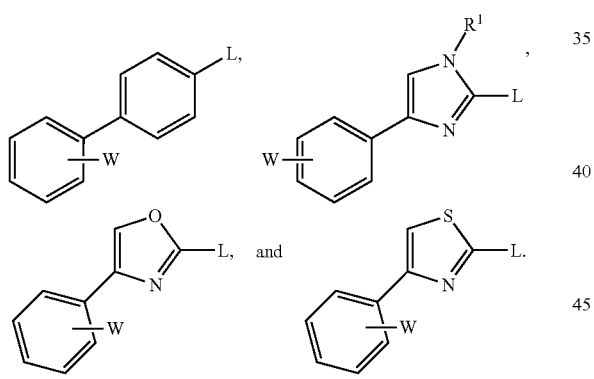

In certain embodiments, the present invention relates to the aforementioned compound, wherein R¹ is hydrogen.

In certain embodiments, the present invention relates to the aforementioned compound, wherein W is —(CH₂)$_q$N(H)T, —(CH₂)$_q$N(H)(αα)$_j$T, —(CH₂)$_q$N(H)C(=O)T, or —(CH₂)$_q$N(H)C(=O)CH(NH₂)T.

In certain embodiments, the present invention relates to the aforementioned compound, wherein q is 0.

In certain embodiments, the present invention relates to the aforementioned compound, wherein q is 1.

In certain embodiments, the present invention relates to the aforementioned compound, wherein j is 1.

In certain embodiments, the present invention relates to the aforementioned compound, wherein j is 2.

In certain embodiments, the present invention relates to the aforementioned compound, wherein αα is

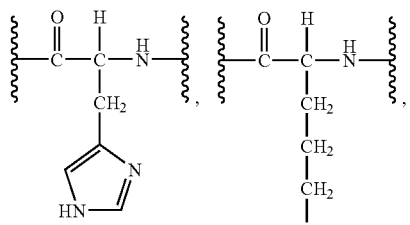

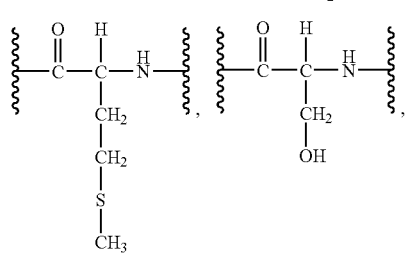

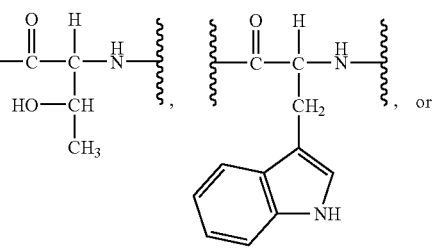

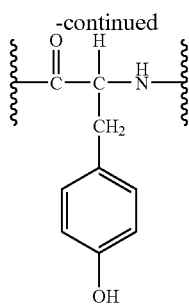

In certain embodiments, the present invention relates to the aforementioned compound, wherein αα is

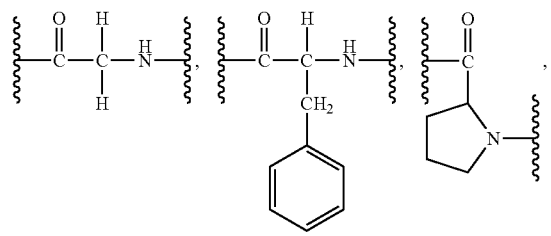

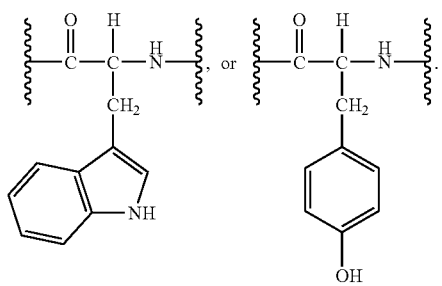

In certain embodiments, the present invention relates to the aforementioned compound, wherein T is hydrogen or alkyl.

In certain embodiments, the present invention relates to the aforementioned compound, wherein L is -(Q$^1$)-CH$_2$-(Q$^2$)-Z, -(Q$^1$)$_m$-O-(Q$^2$)-Z, -(Q$^1$)-N(H)-(Q$^2$)-Z, -(Q$^1$)-S-(Q$^2$)-Z, -(Q$^1$)-C(=O)-(Q$^2$)-Z, -(Q$^1$)-OC(=O)-(Q$^2$)-Z, -(Q$^1$)-N(H)C(=O)-(Q$^2$)-Z, -(Q$^1$)-C(=O)O-(Q$^2$)-Z, -(Q$^1$)-C(=O)N(H)-(Q$^2$)-Z, -(Q$^1$)-OC(=O)O-(Q$^2$)-Z, -(Q$^1$)-N(H)C(=O)N(H)-(Q$^2$)-Z, -(Q$^1$)-OC(=O)N(H)-(Q$^2$)-Z, or -(Q$^1$)-N(H)C(=O)O-(Q$^2$)-Z.

In certain embodiments, the present invention relates to the aforementioned compound, wherein Q$^1$ is a bond, —CH$_2$—, —CH$_2$CH$_2$—, or —CH$_2$CH$_2$CH$_2$—.

In certain embodiments, the present invention relates to the aforementioned compound, wherein Q$^2$ is C$_{3-6}$alkylene.

In certain embodiments, the present invention relates to the aforementioned compound, wherein Q$^2$ is —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, or —CH$_2$CH$_2$CH$_2$CH$_2$H$_2$CH$_2$CH$_2$—.

In certain embodiments, the present invention relates to the aforementioned compound, wherein Z is

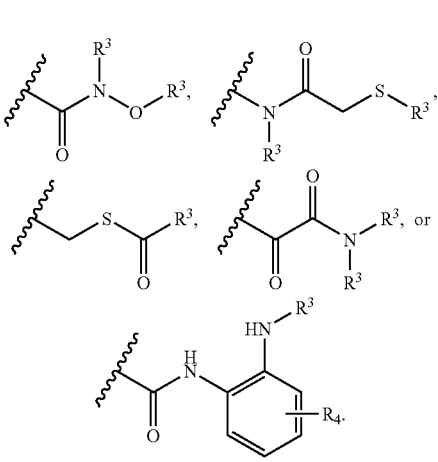

In certain embodiments, the present invention relates to the aforementioned compound, wherein Z is

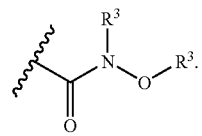

In certain embodiments, the present invention relates to the aforementioned compound, wherein Z is

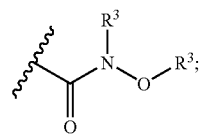

and R$^3$ is hydrogen.

In certain embodiments, the present invention relates to the aforementioned compound, wherein Z is

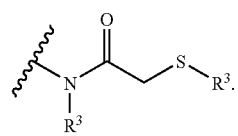

In certain embodiments, the present invention relates to the aforementioned compound, wherein Z is

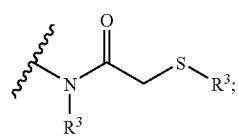

and R$^3$ is hydrogen.

In certain embodiments, the present invention relates to the aforementioned compound, wherein R$^3$ is hydrogen.

In certain embodiments, the present invention relates to the aforementioned compound, wherein R$^4$ is independently for each occurrence, hydrogen, halo, azido, alkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano, or —(CR$_2$)$_p$R.

In certain embodiments, the present invention relates to the aforementioned compound, wherein R$^4$ is hydrogen.

In certain embodiments, the present invention relates to the aforementioned compound, wherein R$^3$ is hydrogen; and R$^4$ is hydrogen.

Another aspect of the invention relates to a compound, or a pharmaceutically acceptable salt, solvate, derivative or prodrug thereof, selected from the group consisting of

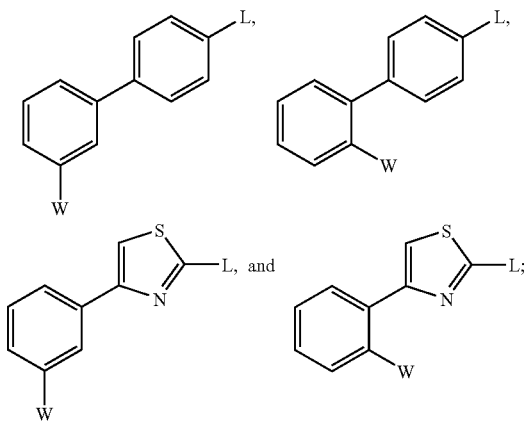

wherein

W is -T, -(αα)$_j$T, —OT, —O(αα)$_j$T, —N(H)T, —N(H)(αα)$_j$T, —ST, —S(αα)$_j$T, —C(=O)T, —OC(=O)T, —N(H)C(=O)T, —C(=O)OT, or —C(=O)N(H)T, —N(H)C(=O)CH(NH$_2$)T, —OC(=O)CH(NH$_2$)T;

j is 1-3 inclusive;

αα is, independently for each occurrence,

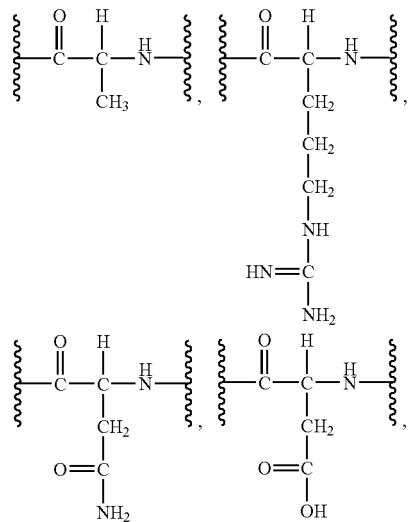

-continued

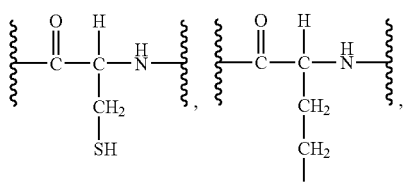

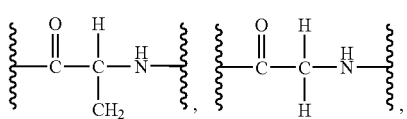

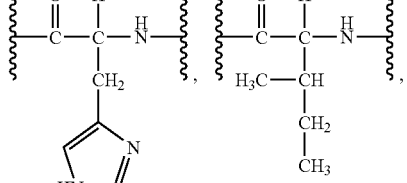

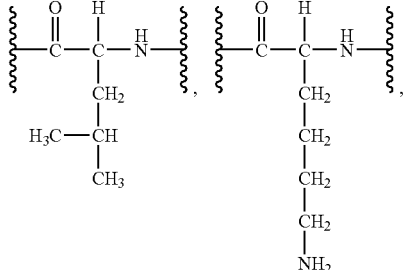

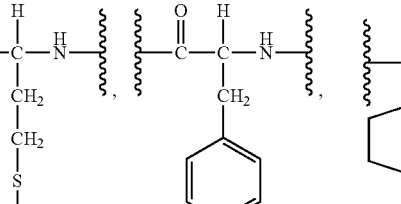

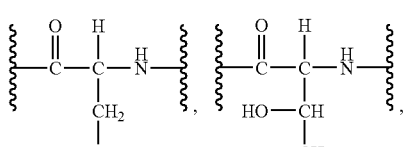

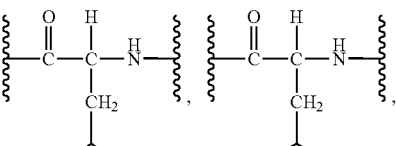

or

-continued

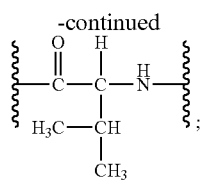

T is hydrogen, alkyl, fluoroalkyl, perfluoroalkyl, aralkyl, alkenyl, alkynyl, cycloalkyl, heterocyclyl, aryl, heteroaryl, aralkyl, heteroaralkyl, or —$(CR_2)_pR$;

R is, independently for each occurrence, hydrogen, halo, azido, alkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, or isocyano;

p is, independently for each occurrence, 0-5 inclusive;

L is -$(Q^1)$-$CH_2$-$(Q^2)$-Z, -$(Q^1)_m$-O-$(Q^2)$-Z, -$(Q^1)$-N(H)-$(Q^2)$-Z, -$(Q^1)$-C(=O)-$(Q^2)$-Z, -$(Q^1)$-OC(=O)-$(Q^2)$-Z, -(O)-N(H)C(=O)-$(Q^2)$-Z, -$(Q^1)$-C(=O)O-$(Q^2)$-Z, -$(Q^1)$-OC(=O)O-$(Q^2)$-Z, -$(Q^1)$-C(=O)N(H)-$(Q^2)$-Z, -$(Q^1)$-N(H)C(=O)N(H)-$(Q^2)$-Z, -$(Q^1)$-OC(=O)N(H)-$(Q^2)$-Z, or -$(Q^1)$-N(H)C(=O)O-$(Q^2)$-Z;

$Q^1$ is $C_{1-3}$alkylene or a bond;
$Q^2$ is $C_{1-10}$alkylene;
Z is

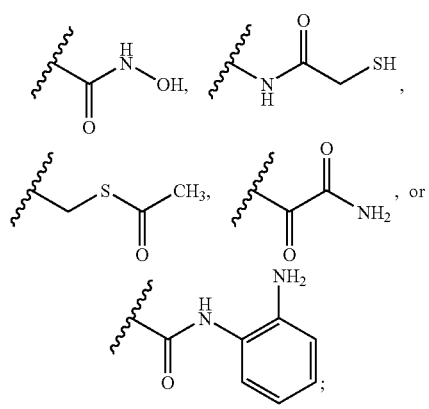

and the stereochemical configuration at any stereocenter is R, S, or a mixture of these configurations.

In certain embodiments, the present invention relates to the aforementioned compound, wherein said compound, or a pharmaceutically acceptable salt, solvate, derivative or prodrug thereof, is

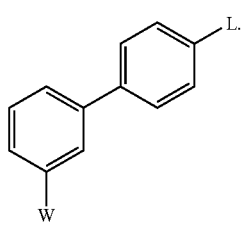

In certain embodiments, the present invention relates to the aforementioned compound, wherein said compound, or a pharmaceutically acceptable salt, solvate, derivative or prodrug thereof, is

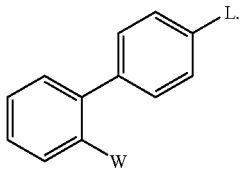

In certain embodiments, the present invention relates to the aforementioned compound, wherein said compound, or a pharmaceutically acceptable salt, solvate, derivative or prodrug thereof, is

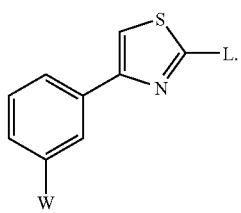

In certain embodiments, the present invention relates to the aforementioned compound, wherein said compound, or a pharmaceutically acceptable salt, solvate, derivative or prodrug thereof, is

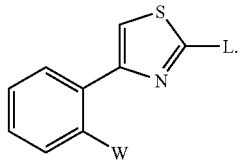

In certain embodiments, the present invention relates to the aforementioned compound, wherein W is —N(H)T, —N(H)(αα)T, —N(H)(αα)(αα)T, or —N(H)C(=O)CH(NH$_2$)T.

In certain embodiments, the present invention relates to the aforementioned compound, wherein W is

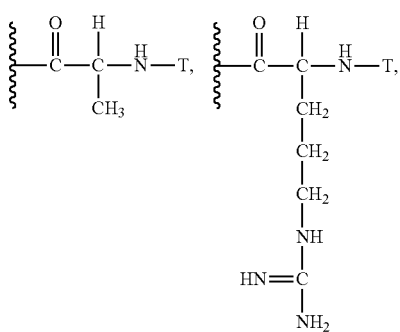

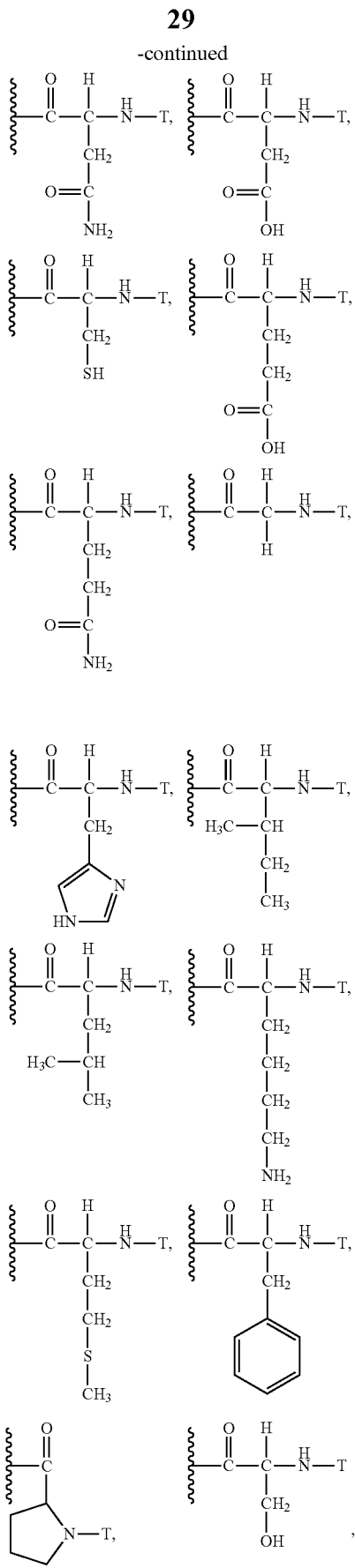
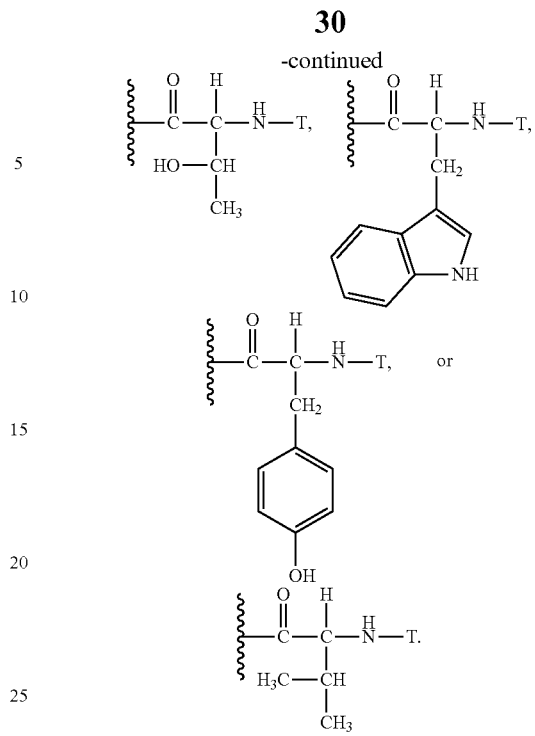

In certain embodiments, the present invention relates to the aforementioned compound, wherein j is 1.

In certain embodiments, the present invention relates to the aforementioned compound, wherein j is 2.

In certain embodiments, the present invention relates to the aforementioned compound, wherein αα is

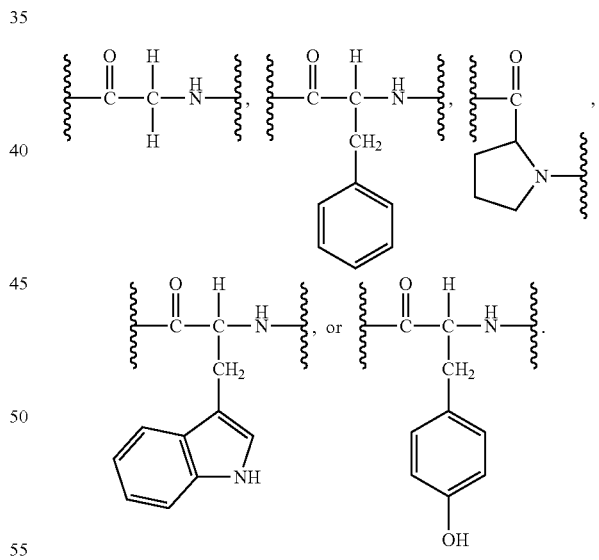

In certain embodiments, the present invention relates to the aforementioned compound, wherein T is hydrogen or alkyl.

In certain embodiments, the present invention relates to the aforementioned compound, wherein p is 0.

In certain embodiments, the present invention relates to the aforementioned compound, wherein p is 1.

In certain embodiments, the present invention relates to the aforementioned compound, wherein L is -($Q^1$)-$CH_2$-($Q^2$)-Z, -($Q^1$)$_m$-O-($Q^2$)-Z, -($Q^1$)-N(H)-($Q^2$)-Z, -($Q^1$)-S-($Q^2$)-Z, -($Q^1$)-C(=O)-($Q^2$)-Z, -($Q^1$)-OC(=O)-($Q^2$)-Z, -($Q^1$)-N(H)C(=O)-($Q^2$)-Z, -($Q^1$)-C(=O)O-($Q^2$)-Z, -($Q^1$)—C(=O)N (H)-(Q²)-Z, -(Q¹)-OC(=O)O-(Q²)-Z, -(Q¹)-N(H)C(=O)N(H)-(Q²)-Z, -(Q¹)-OC(=O)N(H)-(Q²)-Z, or -(Q¹)-N(H)C(=O)O-(Q²)-Z.

In certain embodiments, the present invention relates to the aforementioned compound, wherein L is -(Q¹)-N(H)C(=O)-(Q²)-Z.

In certain embodiments, the present invention relates to the aforementioned compound, wherein Q¹ is a bond, —CH₂—, —CH₂CH₂—, or —CH₂CH₂CH₂—.

In certain embodiments, the present invention relates to the aforementioned compound, wherein Q² is C₃₋₆alkylene.

In certain embodiments, the present invention relates to the aforementioned compound, wherein Q² is —CH₂CH₂CH₂CH₂—, —CH₂CH₂CH₂CH₂CH₂—, —CH₂CH₂CH₂CH₂CH₂CH₂—, or —CH₂CH₂CH₂CH₂H₂CH₂CH₂—.

In certain embodiments, the present invention relates to the aforementioned compound, wherein Z is

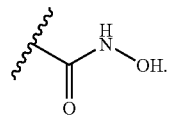 [SMILES: *C(=O)NO]

In certain embodiments, the present invention relates to the aforementioned compound, wherein Z is

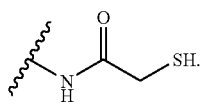 [SMILES: *NC(=O)CS]

Another aspect of the invention relates to a compound or a pharmaceutically acceptable salt, solvate, derivative or prodrug thereof, selected from the group consisting of

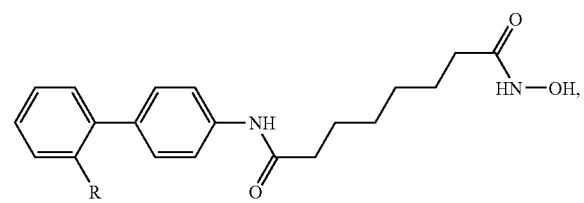

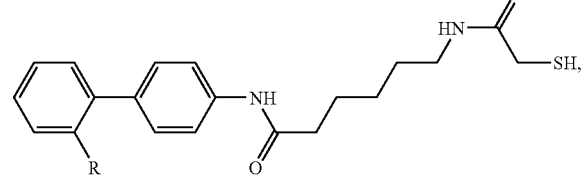

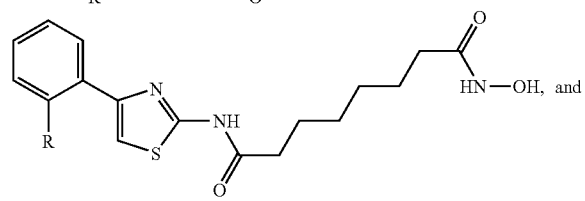

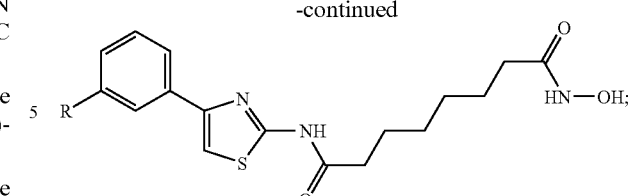

wherein R is

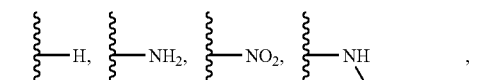

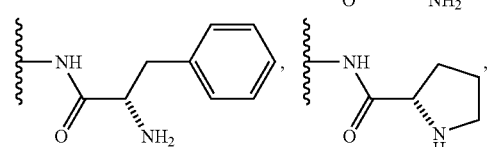

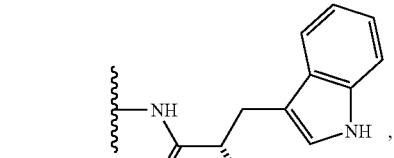

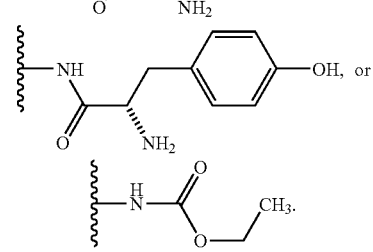

In certain embodiments, the present invention relates to the aforementioned compound, wherein L contains at least three carbon atoms and is composed of a Q¹ moiety and a Q² moiety connected by a —CH₂—, —O—, —N(H)—, —S—, —C(=O), —C(=NH)—, —C(=S)—, —OC(=O)—, —OC(=NH)—, —OC(=S)—, —N(H)C(=O)—, —N(H)C(=NH)—, —N(H)C(=S)—, —SC(=O)—, —SC(=NH)—, —SC(=S)—, —C(=O)O—, —C(=NH)O—, —C(=S)O—, —C(=O)N(H)—, —C(=NH)N(H)—, —C(=S)N(H)—, —C(=O)S—, —C(=NH)S—, —C(=S)S—, —OC(=O)O—, —OC(=NH)O—, —OC(=S)O—, —N(H)C(=O)N(H)—, —N(H)C(=NH)N(H)—, —N(H)C(=S)N(H)—, —OC(=O)N(H)—, —OC(=NH)N(H)—, —OC(=S)N(H)—, —N(H)C(=O)O—, —N(H)C(=NH)O—, or —N(H)C(=S)O— moiety.

In certain embodiments, the present invention relates to the aforementioned compound, wherein Q¹ and Q² are alkylene.

In certain embodiments, the present invention relates to the aforementioned compound, wherein Q¹ is absent. In certain embodiments, the present invention relates to the aforementioned compound, wherein Q² is absent.

In certain embodiments, the present invention relates to the aforementioned compound, wherein Q¹ has a backbone of: at least 1 carbon atom; at least 2 carbon atoms; at least 3 carbon atoms; at least 4 carbon atoms; or, at least 5 carbon atoms. In certain embodiments, the present invention relates to the aforementioned compound, wherein $Q^2$ has a backbone of: at least 5 carbon atom; at least 6 carbon atoms; at least 7 carbon atoms; at least 8 carbon atoms; or, at least 9 carbon atoms.

In certain embodiments, the present invention relates to the aforementioned compound, wherein $Q^1$ has a backbone of: from 0 to 5 carbon atoms; from 1 to 4 carbon atoms; or from 1 to 3 carbon atoms. In certain embodiments, the present invention relates to the aforementioned compound, wherein $Q^2$ has a backbone of: from 1 to 10 carbon atoms; from 2 to 9 carbon atoms; from 3 to 8 carbon atoms; from 4 to 8 carbon atoms; from 5 to 8 carbon atoms; or from 5 to 7 carbon atoms.

In certain embodiments, the present invention relates to the aforementioned compound, wherein $Q^1$ has a backbone of: 1 carbon atom; 2 carbon atoms; 3 carbon atoms; 4 carbon atoms; 5 carbon atoms; 6 carbon atom; 7 carbon atoms; 8 carbon atoms; 9 carbon atoms; or, 10 carbon atoms. In certain embodiments, the present invention relates to the aforementioned compound, wherein $Q^2$ has a backbone of 1 carbon atom; 2 carbon atoms; 3 carbon atoms; 4 carbon atoms; 5 carbon atoms; 6 carbon atom; 7 carbon atoms; 8 carbon atoms; 9 carbon atoms; or, 10 carbon atoms.

In certain embodiments, the present invention relates to the aforementioned compound, wherein $Q^1$ is an alkylene group, and has a backbone of at least 2 carbon atoms. In certain embodiments, the present invention relates to the aforementioned compound, wherein $Q^1$ has a backbone of at least 2 carbon atoms, and is a $C_{2-7}$alkylene group. In certain embodiments, the present invention relates to the aforementioned compound, wherein $Q^1$ has a backbone of at least 3 carbon atoms, and is a $C_{3-7}$alkylene group. In certain embodiments, the present invention relates to the aforementioned compound, wherein $Q^2$ is an alkylene group, and has a backbone of at least 2 carbon atoms. In certain embodiments, the present invention relates to the aforementioned compound, wherein $Q^2$ has a backbone of at least 2 carbon atoms, and is a $C_{2-7}$alkylene group. In certain embodiments, the present invention relates to the aforementioned compound, wherein $Q^2$ has a backbone of at least 3 carbon atoms, and is a $C_{3-7}$alkylene group.

In certain embodiments, the present invention relates to the aforementioned compound, wherein $Q^1$ has a backbone of at least 2 carbon atoms, and is a saturated $C_{2-7}$alkylene group. In certain embodiments, the present invention relates to the aforementioned compound, wherein $Q^1$ has a backbone of at least 3 carbon atoms, and is a saturated $C_{3-7}$alkylene group. In certain embodiments, the present invention relates to the aforementioned compound, wherein $Q^2$ has a backbone of at least 2 carbon atoms, and is a saturated $C_{2-7}$alkylene group. In certain embodiments, the present invention relates to the aforementioned compound, wherein $Q^2$ has a backbone of at least 3 carbon atoms, and is a saturated $C_{3-7}$alkylene group.

In certain embodiments, the present invention relates to the aforementioned compound, wherein $Q^1$ has a backbone of at least 2 carbon atoms, and is a partially unsaturated $C_{2-7}$alkylene group. In certain embodiments, the present invention relates to the aforementioned compound, wherein $Q^1$ has a backbone of at least 3 carbon atoms, and is a partially unsaturated $C_{3-7}$alkylene group. In certain embodiments, the present invention relates to the aforementioned compound, wherein $Q^2$ has a backbone of at least 2 carbon atoms, and is a partially unsaturated $C_{2-7}$alkylene group. In certain embodiments, the present invention relates to the aforementioned compound, wherein $Q^2$ has a backbone of at least 3 carbon atoms, and is a partially unsaturated $C_{3-7}$alkylene group. In certain embodiments, the present invention relates to the aforementioned compound, wherein $Q^2$ has a backbone of at least 2 carbon atoms, and is an aliphatic $C_{2-7}$alkylene group. In certain embodiments, the present invention relates to the aforementioned compound, wherein $Q^2$ has a backbone of at least 3 carbon atoms, and is an aliphatic $C_{3-8}$alkylene group.

In certain embodiments, the present invention relates to the aforementioned compound, wherein $Q^1$ has a backbone of at least 2 carbon atoms, and is a linear $C_{2-7}$alkylene group. In certain embodiments, the present invention relates to the aforementioned compound, wherein $Q^1$ has a backbone of at least 3 carbon atoms, and is a linear $C_{3-7}$alkylene group. In certain embodiments, the present invention relates to the aforementioned compound, wherein $Q^2$ has it backbone of at least 2 carbon atoms, and is a linear $C_{2-7}$alkylene group. In certain embodiments, the present invention relates to the aforementioned compound, wherein $Q^2$ has a backbone of at least 3 carbon atoms, and is a linear $C_{3-7}$alkylene group.

In certain embodiments, the present invention relates to the aforementioned compound, wherein $Q^1$ has a backbone of at least 2 carbon atoms, and is a branched $C_{2-7}$alkylene group. In certain embodiments, the present invention relates to the aforementioned compound, wherein $Q^1$ has a backbone of at least 3 carbon atoms, and is a branched $C_{3-7}$alkylene group. In certain embodiments, the present invention relates to the aforementioned compound, wherein $Q^2$ has a backbone of at least 2 carbon atoms, and is a branched $C_{2-7}$alkylene group. In certain embodiments, the present invention relates to the aforementioned compound, wherein $Q^2$ has a backbone of at least 3 carbon atoms, and is a branched $C_{3-7}$alkylene group.

In certain embodiments, the present invention relates to the aforementioned compound, wherein $Q^1$ has backbone of at least 2 carbon atoms, and is an alicyclic $C_{2-7}$alkylene group. In certain embodiments, the present invention relates to the aforementioned compound, wherein $Q^1$ has a backbone of at least 3 carbon atoms, and is an alicyclic $C_{3-7}$alkylene group. In certain embodiments, the present invention relates to the aforementioned compound, wherein $Q^2$ has backbone of at least 2 carbon atoms, and is an alicyclic $C_{2-7}$alkylene group. In certain embodiments, the present invention relates to the aforementioned compound, wherein $Q^2$ has a backbone of at least 3 carbon atoms, and is an alicyclic $C_{3-7}$alkylene group.

In certain embodiments, the present invention relates to the aforementioned compound, wherein $Q^1$ has a backbone of at least 2 carbon atoms, and is a saturated aliphatic $C_{2-7}$alkylene group. In certain embodiments, the present invention relates to the aforementioned compound, wherein $Q^1$ has a backbone of at least 3 carbon atoms, and is a saturated aliphatic $C_{3-7}$alkylene group. In certain embodiments, the present invention relates to the aforementioned compound, wherein $Q^2$ has a backbone of at least 2 carbon atoms, and is a saturated aliphatic $C_{2-7}$alkylene group. In certain embodiments, the present invention relates to the aforementioned compound, wherein $Q^2$ has a backbone of at least 3 carbon atoms, and is a saturated aliphatic $C_{3-7}$alkylene group.

In certain embodiments, the present invention relates to the aforementioned compound, wherein $Q^1$ has a backbone of at least 2 carbon atoms, and is a saturated linear $C_{2-7}$alkylene group. In certain embodiments, the present invention relates to the aforementioned compound, wherein $Q^1$ has a backbone of at least 3 carbon atoms, and is a saturated linear $C_{3-7}$alkylene group. In certain embodiments, the present invention relates to the aforementioned compound, wherein $Q^2$ has a backbone of at least 2 carbon atoms, and is a saturated linear $C_{2-7}$alkylene group. In certain embodiments, the present invention relates to the aforementioned compound, wherein $Q^2$ has a backbone of at least 3 carbon atoms, and is a saturated linear $C_{3-7}$alkylene group.

In certain embodiments, the present invention relates to the aforementioned compound, wherein $Q^1$ has a backbone of at least 2 carbon atoms, and is a saturated branched $C_{2-7}$alkylene group. In certain embodiments, the present invention relates to the aforementioned compound, wherein $Q^1$ has a backbone of at least 3 carbon atoms, and is a saturated branched $C_{3-7}$alkylene group. In certain embodiments, the present invention relates to the aforementioned compound, wherein $Q^2$ has a backbone of at least 2 carbon atoms, and is a saturated branched $C_{2-7}$alkylene group. In certain embodiments, the present invention relates to the aforementioned compound, wherein $Q^2$ has a backbone of at least 3 carbon atoms, and is a saturated branched $C_{3-7}$alkylene group.

In certain embodiments, the present invention relates to the aforementioned compound, wherein $Q^1$ has a backbone of at least 2 carbon atoms, and is a saturated alicyclic $C_{2-7}$alkylene group. In certain embodiments, the present invention relates to the aforementioned compound, wherein $Q^1$ has a backbone of at least 3 carbon atoms, and is a saturated alicyclic $C_{3-7}$alkylene group. In certain embodiments, the present invention relates to the aforementioned compound, wherein $Q^2$ has a backbone of at least 2 carbon atoms, and is a saturated alicyclic $C_{2-7}$alkylene group. In certain embodiments, the present invention relates to the aforementioned compound, wherein $Q^2$ has a backbone of at least 3 carbon atoms, and is a saturated alicyclic $C_{3-7}$alkylene group.

In certain embodiments, the present invention relates to the aforementioned compound, wherein $Q^1$ has a backbone of at least 2 carbon atoms, and is a partially unsaturated aliphatic $C_{2-7}$alkylene group. In certain embodiments, the present invention relates to the aforementioned compound, wherein $Q^1$ has a backbone of at least 3 carbon atoms, and is a partially unsaturated aliphatic $C_{3-7}$alkylene group. In certain embodiments, the present invention relates to the aforementioned compound, wherein $Q^2$ has a backbone of at least 2 carbon atoms, and is a partially unsaturated aliphatic $C_{2-7}$alkylene group. In certain embodiments, the present invention relates to the aforementioned compound, wherein $Q^2$ has a backbone of at least 3 carbon atoms, and is a partially unsaturated aliphatic $C_{3-7}$alkylene group.

In certain embodiments, the present invention relates to the aforementioned compound, wherein $Q^1$ has a backbone of at least 2 carbon atoms, and is a partially unsaturated linear $C_{2-7}$alkylene group. In certain embodiments, the present invention relates to the aforementioned compound, wherein $Q^1$ has a backbone of at least 3 carbon atoms, and is a partially unsaturated linear $C_{3-7}$alkylene group. In certain embodiments, the present invention relates to the aforementioned compound, wherein $Q^2$ has a backbone of at least 2 carbon atoms, and is a partially unsaturated linear $C_{2-7}$alkylene group. In certain embodiments, the present invention relates to the aforementioned compound, wherein $Q^2$ has a backbone of at least 3 carbon atoms, and is a partially unsaturated linear $C_{3-7}$alkylene group.

In certain embodiments, the present invention relates to the aforementioned compound, wherein $Q^1$ has a backbone of at least 2 carbon atoms, and is a partially unsaturated branched $C_{2-7}$alkylene group. In certain embodiments, the present invention relates to the aforementioned compound, wherein $Q^1$ has a backbone of at least 3 carbon atoms, and is a partially unsaturated branched $C_{3-7}$alkylene group. In certain embodiments, the present invention relates to the aforementioned compound, wherein $Q^2$ has a backbone of at least 2 carbon atoms, and is a partially unsaturated branched $C_{2-7}$alkylene group. In certain embodiments, the present invention relates to the aforementioned compound, wherein $Q^2$ has a backbone of at least 3 carbon atoms, and is a partially unsaturated branched $C_{3-7}$alkylene group.

In certain embodiments, the present invention relates to the aforementioned compound, wherein $Q^1$ has a backbone of at least 2 carbon atoms, and is a partially unsaturated alicyclic $C_{2-7}$alkylene group. In certain embodiments, the present invention relates to the aforementioned compound, wherein $Q^1$ has a backbone of at least 3 carbon atoms, and is a partially unsaturated alicyclic $C_{3-7}$alkylene group. In certain embodiments, the present invention relates to the aforementioned compound, wherein $Q^2$ has a backbone of at least 2 carbon atoms, and is a partially unsaturated alicyclic $C_{2-7}$alkylene group. In certain embodiments, the present invention relates to the aforementioned compound, wherein $Q^2$ has a backbone of at least 3 carbon atoms, and is a partially unsaturated alicyclic $C_{3-7}$alkylene group.

Note that where unsaturation permits isomers (e.g., cis- and trans-, E- and Z-, etc. and combinations thereof), a reference to one isomer is to be considered a reference to all such isomers, unless otherwise specified.

In certain embodiments, the present invention relates to the aforementioned compound, wherein $Q^1$ and/or $Q^2$ is optionally substituted. In certain embodiments, the present invention relates to the aforementioned compound, wherein $Q^1$ is substituted. Examples of substituents on $Q^1$ include, but are not limited to, —F, —Cl, —Br, —I, —OH, -OMe, -OEt, -O(tBu), —OCH$_2$Ph, —SH, -SMe, -SEt, —S(tBu), —SCH$_2$Ph, —C(=O)H, —C(=O)Me, —C(=O)Et, —C(=O)(tBu), —C(=O)Ph, —C(=O)OH, —C(=O)OMe, —C(=O)OEt, —C(=O)O(tBu), —C(=O)NH$_2$, —C(=O)NHMe, —C(=O)NMe$_2$, —C(=O)NHEt, —NHC(=O)Me, —NHC(=O)Et, —NHC(=O)Ph, succinimidyl, maleimidyl, —NH$_2$, -NHMe, -NHEt, —NH(iPr), —NH(nPr), -NMe$_2$, -NEt$_2$, —N(iPr)$_2$, —N(nPr)$_2$, —N(nBu)$_2$, —N(tBu)$_2$, —CN, —NO$_2$, -Me, -Et, -nPr, -iPr, -nBu, -tBu, —CF$_3$, —CHF$_2$, —CH$_2$F, —CCl$_3$, —CBr$_3$, —CH$_2$CH$_2$F, —CH$_2$CHF$_2$, —CH$_2$CF$_3$, —OCF$_3$, —OCHF$_2$, —OCH$_2$F, —OCCl$_3$, —OCBr$_3$, —OCH$_2$CH$_2$F, —OCH$_2$CHF$_2$, —OCH$_2$CF$_3$, —CH$_2$OH, —CH$_2$CH$_2$OH, —CH(OH)CH$_2$OH, —CH$_2$NH$_2$, —CH$_2$CH$_2$NH$_2$, —CH$_2$CH$_2$NMe$_2$, and optionally substituted phenyl.

In certain embodiments, the present invention relates to the aforementioned compound, wherein $Q^1$ is alkylene. In certain embodiments, the present invention relates to the aforementioned compound, wherein $Q^2$ is alkylene.

In certain embodiments, the present invention relates to the aforementioned compound, wherein $Q^1$ and/or $Q^2$ are selected from the group consisting of —(CH$_2$)$_n$— where n is an integer from 0 to 10, —CH(CH$_3$)CH$_2$—, —CH$_2$CH(CH$_3$)—, —CH(CH$_3$)CH$_2$CH$_2$—, —CH$_2$CH(CH$_3$)CH$_2$—, —CH$_2$CH$_2$CH(CH$_3$)—; —CH(CH$_3$)CH$_2$CH$_2$CH$_2$—, —CH$_2$CH(CH$_3$)CH$_2$CH$_2$—, —CH$_2$CH$_2$CH(CH$_3$)CH$_2$—, —CH$_2$CH$_2$CH$_2$CH(CH$_3$)—, —CH(CH$_3$)CH$_2$CH$_2$CH$_2$CH$_2$—, —CH$_2$CH(CH$_3$)CH$_2$CH$_2$CH$_2$—, —CH$_2$CH$_2$CH(CH$_3$)CH$_2$CH$_2$—, —CH$_2$CH$_2$CH$_2$CH(CH$_3$)CH$_2$—, —CH$_2$CH$_2$CH$_2$CH$_2$CH(CH$_3$)—, —CH(CH$_2$CH$_3$)CH$_2$—, -CH$_2$CH(CH$_2$CH$_3$)—, —CH(CH$_2$CH$_3$)CH$_2$CH$_2$—, —CH$_2$CH(CH$_2$CH$_3$)CH$_2$—, —CH$_2$CH$_2$CH(CH$_2$CH$_3$)—, —CH(CH$_2$CH$_3$)CH$_2$CH$_2$CH$_2$—, —CH$_2$CH(CH$_2$CH$_3$)CH$_2$CH$_2$—, —CH$_2$CH$_2$CH(CH$_2$CH$_3$)CH$_2$—, —CH$_2$CH$_2$CH$_2$CH(CH$_2$CH$_3$)—, —CH(CH$_2$CH$_3$)CH$_2$CH$_2$CH$_2$CH$_2$—, —CH$_2$CH(CH$_2$CH$_3$)CH$_2$CH$_2$CH$_2$—, —CH$_2$CH$_2$CH(CH$_2$CH$_3$)CH$_2$CH$_2$—, —CH$_2$CH$_2$CH$_2$CH(CH$_2$CH$_3$)CH$_2$—, —CH$_2$CH$_2$CH$_2$CH$_2$CH(CH$_2$CH$_3$)—, —CH=CH—, —CH=CHCH₂—, —CH₂CH=CH—, —CH=CHCH₂CH₂—, —CH₂CH=CHCH₂—, —CH₂CH₂CH=CH—, —CH=CHCH₂CH₂CH₂—, —CH₂CH=CHCH₂CH₂—, —CH₂CH₂CH=CHCH₂—, —CH₂CH₂CH₂CH=CH—, —CH=CHCH₂CH₂CH₂CH₂—, —CH₂CH=CHCH₂CH₂CH₂—, —CH₂CH₂CH=CHCH₂CH₂—, —CH₂CH₂CH₂CH=CHCH₂—, —CH₂CH₂CH₂CH₂CH=CH—, —C(CH₃)=CH—, —CH=C(CH₃)—, —C(CH₃)=CHCH₂—, —CH=C(CH₃)CH₂—, —CH=CHCH(CH₃)—, —CH(CH₃)CH=CH—, —CH₂C(CH₃)=CH—, —CH₂CH=C(CH₃)—, —CH=CHCH=CH—, —CH=CHCH=CHCH₂—, —CH₂CH=CHCH=CH—, —CH=CHCH₂CH=CH—, —CH=CHCH=CHCH₂CH₂—, —CH=CHCH₂CH=CHCH₂—, —CH=CHCH₂CH₂CH=CH—, —CH₂CH=CHCH=CHCH₂—, —CH₂CH=CHCH₂CH=CH—, —CH₂CH₂CH=CHCH=CH—, —C(CH3)=CHCH=CH—, —CH=C(CH₃)CH=CH—, —CH=CHC(CH₃)=CH—, —CH=CHCH=C(CH₃)—, —C≡C—; —C≡CCH₂—, —CH₂C≡C—; —C≡CCH(CH₃)—, —CH(CH₃)C≡C—, —C≡CCH₂CH₂—, —CH₂C≡CCH₂—, —CH₂CH₂C≡C—, —C≡CCH(CH₃)CH₂—, —C≡CCH₂CH(CH₃)—, —CH(CH₃)C≡CCH₂—, —CH₂C≡CCH(CH₃)—, —CH(CH₃)CH₂C≡C—, —CH₂CH(CH₃)C≡C—, —C≡CCH=CH—, —CH=CHC≡C—, —C≡CC≡C—, —C≡CCH₂CH₂CH₂—, —CH₂CH₂CH₂C≡C—, —C≡CCH₂CH₂CH₂—, —CH₂CH₂CH₂C≡C—, —C≡CCH=CHCH=CH—, —CH=CHC≡C—CH=CH—, —CH=CHCH=CHC≡C—, —C(CH₃)=CHC≡C—, —CH=C(CH₃)C≡C—, —C≡CC(CH₃)=CH—, —C≡CCH=C(CH₃)—, cyclopentylene, cyclopentenylene, cyclohexylene, cyclohexenylene, and cyclohexadienylene.

In certain embodiments, the present invention relates to any of the aforementioned compounds, provided that W is not one or more of the following: —H, —Cl, —Br, —I, —F, —C≡N, —SH, —OH, —NH₂, —SO₃H, —NO₂, —CH₃, —CF₃, —CH₂CH₃, —CH₂CH₂CH₃, —CH(CH₃)₂, —CH₂CH₂CH₂CH₃, —CH(CH₃)CH₂CH₃, —CH₂CH(CH₃)₂, —C(CH₃)₃, —OCH₃, —OCH₂CH₃, —OCH₂CH₂CH₃, —OCH(CH₃)₂, —OCH₂CH₂CH₂CH₃, —OCH(CH₃)CH₂CH₃, —OCH₂CH(CH₃)₂, —OC(CH₃)₃, —OC₆H₅, —OCH₂C₆H₅, —N(H)CH₃, —N(H)CH₂CH₃, —N(H)CH₂CH₂CH₃, —N(H)CH(CH₃)₂, —N(H)CH₂CH₂CH₂CH₃, —N(H)CH(CH₃)CH₂CH₃, —N(H)CH₂CH(CH₃)₂, —N(H)C(CH₃)₃, —N(H)C₆H₅, —N(H)CH₂C₆H₅, —N(CH₃)₂, —N(CH₂CH₃)₂, —N(CH₂CH₂CH₃)₂, —N(CH(CH₃)₂)₂, —N(CH₂CH₂CH₂CH₃)₂, —N(CH(CH₃)CH₂CH₃)₂, —N(CH₂CH(CH₃)₂)₂, —N(C(CH₃)₃)₂, —N(C₆H₅)₂, —N(CH₂C₆H₅)₂, —SCH₃, —SCH₂CH₃, —SCH₂CH₂CH₃, —SCH(CH₃)₂, —SCH₂CH₂CH₂CH₃, —SCH(CH₃)CH₂CH₃, —SCH₂CH(CH₃)₂, —SC(CH₃)₃, —SC₆H₅, —C(=O)CH₃, —C(=O)CF₃, —C(=O)CH₂CH₃, —C(=O)CH₂CH₂CH₃, —C(=O)CH(CH₃)₂, —C(=O)CH₂CH₂CH₂CH₃, —C(=O)CH(CH₃)CH₂CH₃, —C(=O)CH₂CH(CH₃)₂, —C(=O)C(CH₃)₃, —C(=O)OCH₃, —C(=O)OCH₂CH₃, —C(=O)OCH₂CH₂CH₃, —C(=O)OCH(CH₃)₂, —C(=O)OCH₂CH₂CH₂CH₃, —C(=O)OCH(CH₃)CH₂CH₃, —C(=O)OCH₂CH(CH₃)₂, —C(=O)OC(CH₃)₃, —C(=O)OC₆H₅, —C(=O)OCH₂C₆H₅, —C(=O)N(H)CH₃, —C(=O)N(H)CH₂CH₃, —C(=O)N(H)CH₂CH₂CH₃, —C(=O)N(H)CH(CH₃)₂, —C(=O)N(H)CH₂CH₂CH₂CH₃, —C(=O)N(H)CH(CH₃)CH₂CH₃, —C(=O)N(H)CH₂CH(CH₃)₂, —C(=O)N(H)C(CH₃)₃, —C(=O)N(H)C₆H₅, —C(=O)N(H)CH₂C₆H₅, —C(=O)N(CH₃)₂, —C(=O)N(CH₂CH₃)₂, —C(=O)N(CH₂CH₂CH₃)₂, —C(=O)N(CH(CH₃)₂)₂, —C(=O)N(CH₂CH₂CH₂CH₃)₂, —C(=O)N(CH(CH₃)CH₂CH₃)₂, —C(=O)N(CH₂CH(CH₃)₂)₂, —C(=O)N(C(CH₃)₃)₂, —C(=O)N(C₆H₅)₂, —C(=O)N(CH₂C₆H₅)₂, —C(=O)SCH₃, —C(=O)SCH₂CH₃, —C(=O)SCH₂CH₂CH₃, —C(=O)SCH(CH₃)₂, —C(=O)SCH₂CH₂CH₂CH₃, —C(=O)SCH(CH₃)CH₂CH₃, —C(=O)SCH₂CH(CH₃)₂, —C(=O)SC(CH₃)₃, —C(=O)SC₆H₅, —OC(=O)CH₃, —OC(=O)CH₂CH₃, —OC(=O)CH₂CH₂CH₃, —OC(=O)CH(CH₃)₂, —OC(=O)CH₂CH₂CH₂CH₃, —OC(=O)CH(CH₃)CH₂CH₃, —OC(=O)CH₂CH(CH₃)₂, —OC(=O)C(CH₃)₃, —OC(=O)C₆H₅, —OC(=O)CH₂C₆H₅, —N(H)C(=O)CH₃, —N(H)C(=O)CH₂CH₃, —N(H)C(=O)CH₂CH₂CH₃, —N(H)C(=O)CH(CH₃)₂, —N(H)C(=O)CH₂CH₂CH₂CH₃, —N(H)C(=O)CH(CH₃)CH₂CH₃, —N(H)C(=O)CH₂CH(CH₃)₂, —N(H)C(=O)C(CH₃)₃, —N(H)C(=O)C₆H₅, —N(H)C(=O)CH₂C₆H₅, —SC(=O)CH₃, —SC(=O)CH₂CH₃, —SC(=O)CH₂CH₂CH₃, —SC(=O)CH(CH₃)₂, —SC(=O)CH₂CH₂CH₂CH₃, —SC(=O)CH(CH₃)CH₂CH₃, —SC(=O)CH₂CH(CH₃)₂, —SC(=O)C(CH₃)₃, —SC(=O)C₆H₅, —CH=CH₂, —C≡CH, —C(CH₃)=CH₂, —CH=CH(CH₃), and —C≡C(CH₃).

In any of the forgoing embodiments

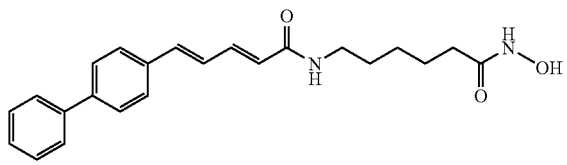 [SMILES: O=C(/C=C/C=C/c1ccc(-c2ccccc2)cc1)NCCCCCC(=O)NO]

may be specifically excluded.

In any of the forgoing embodiments

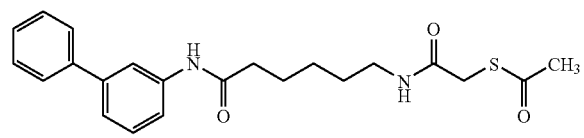 [SMILES: CC(=O)SCC(=O)NCCCCCC(=O)Nc1cccc(-c2ccccc2)c1]

may be specifically excluded.

In any of the forgoing embodiments

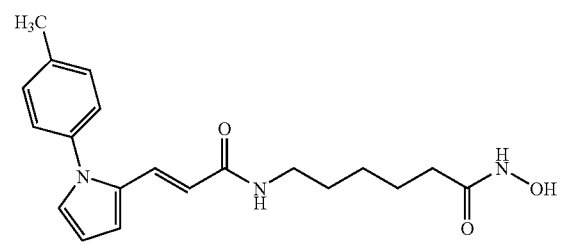 [SMILES: Cc1ccc(-n2cccc2/C=C/C(=O)NCCCCCC(=O)NO)cc1]

may be specifically excluded.

In any of the forgoing embodiments

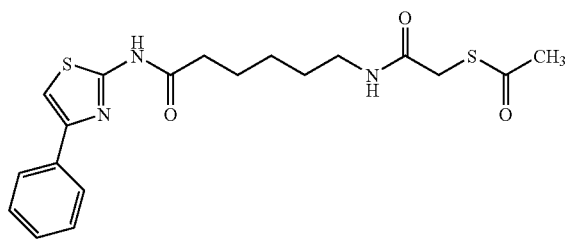 [SMILES: CC(=O)SCC(=O)NCCCCCC(=O)Nc1nc(-c2ccccc2)cs1]

may be specifically excluded.
In any of the forgoing embodiments

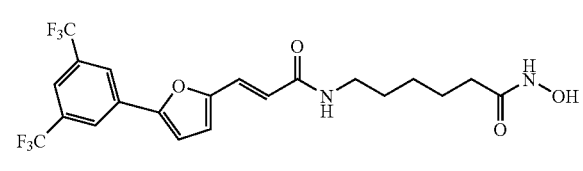 [SMILES: O=C(/C=C/c1ccc(-c2cc(C(F)(F)F)cc(C(F)(F)F)c2)o1)NCCCCCC(=O)NO]

may be specifically excluded.
In any of the forgoing embodiments

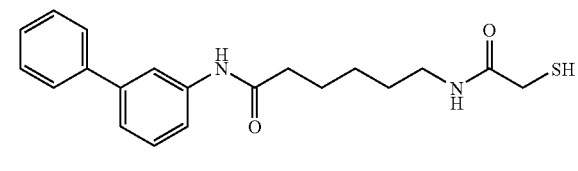 [SMILES: O=C(CS)NCCCCCC(=O)Nc1cccc(-c2ccccc2)c1]

may be specifically excluded.
In any of the forgoing embodiments

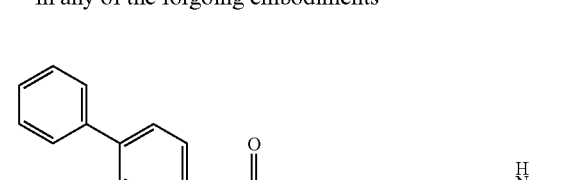

may be specifically excluded.
In any of the forgoing embodiments may be specifically excluded.

In any of the forgoing embodiments

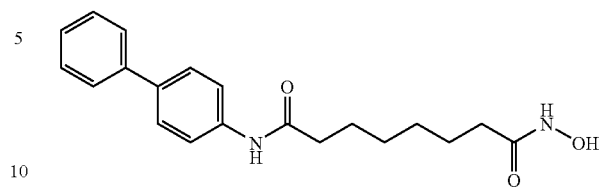

may be specifically excluded.
In any of the forgoing embodiments

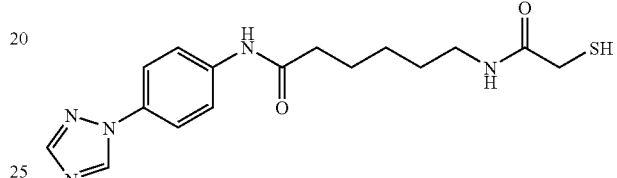

may be specifically excluded.
In any of the forgoing embodiments may be specifically excluded.
In any of the forgoing embodiments may be specifically excluded.

In any of the forgoing embodiments

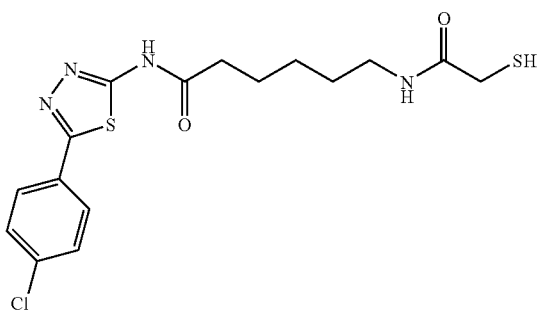 [SMILES: O=C(CS)NCCCCCC(=O)Nc1nnc(-c2ccc(Cl)cc2)s1]

may be specifically excluded.
In any of the forgoing embodiments

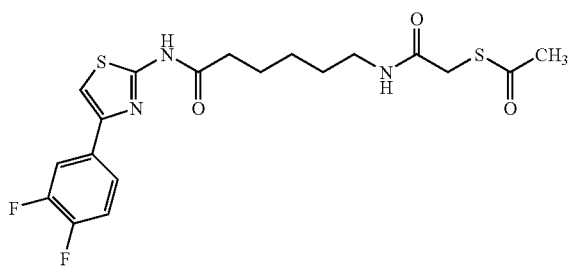 [SMILES: CC(=O)SCC(=O)NCCCCCC(=O)Nc1nc(-c2ccc(F)c(F)c2)cs1]

may be specifically excluded.
In any of the forgoing embodiments

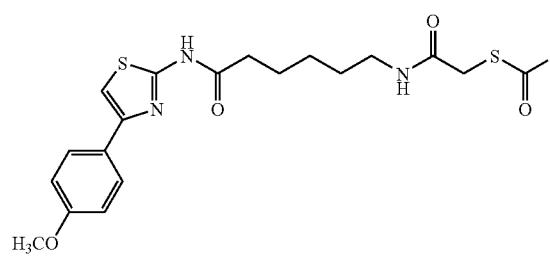

may be specifically excluded.
In any of the forgoing embodiments

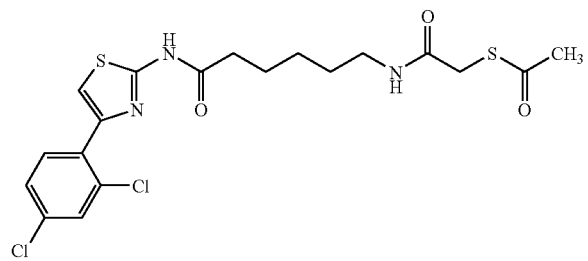 [SMILES: CC(=O)SCC(=O)NCCCCCC(=O)Nc1nc(-c2ccc(Cl)cc2Cl)cs1]

may be specifically excluded.

In any of the forgoing embodiments

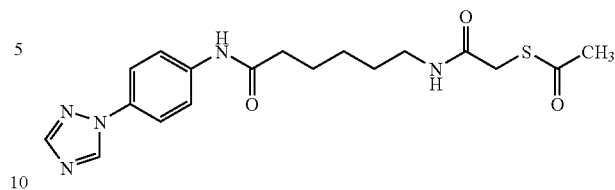

may be specifically excluded.
In any of the forgoing embodiments

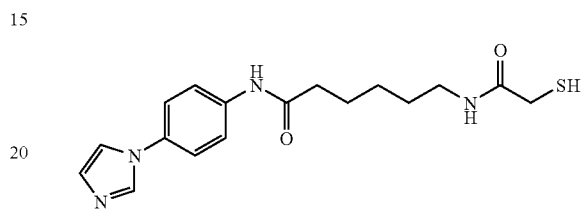

may be specifically excluded.
In any of the forgoing embodiments

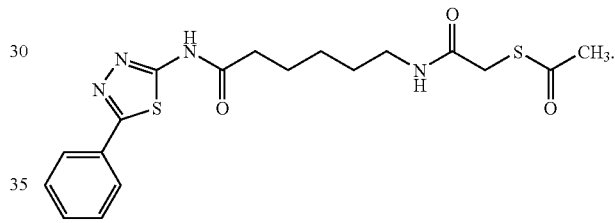

may be specifically excluded.
In any of the forgoing embodiments

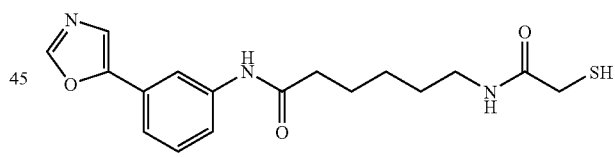

may be specifically excluded.
In any of the forgoing embodiments

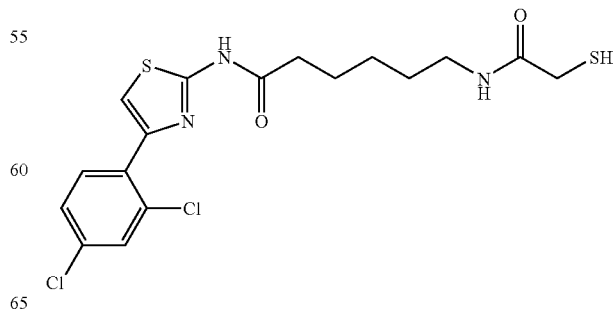

may be specifically excluded.

In any of the forgoing embodiments

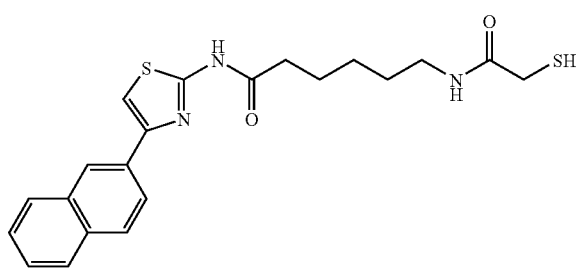 [SMILES: O=C(CS)NCCCCCC(=O)Nc1nc(-c2ccc3ccccc3c2)cs1]

may be specifically excluded.

In any of the forgoing embodiments

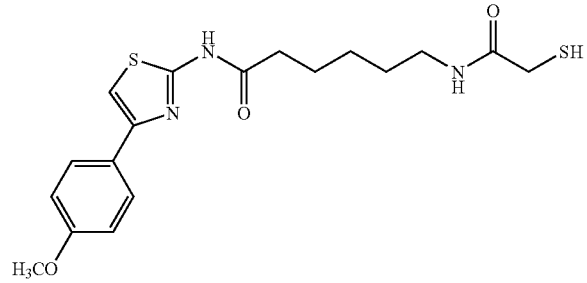 [SMILES: COc1ccc(-c2csc(NC(=O)CCCCCNC(=O)CS)n2)cc1]

may be specifically excluded.

In any of the forgoing embodiments

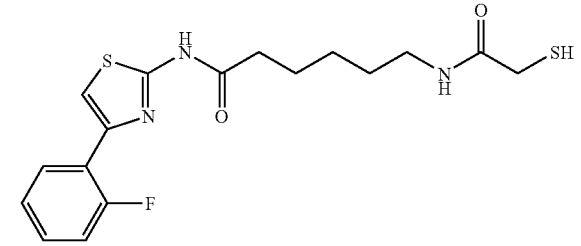 [SMILES: O=C(CS)NCCCCCC(=O)Nc1nc(-c2ccccc2F)cs1]

may be specifically excluded.

In any of the forgoing embodiments

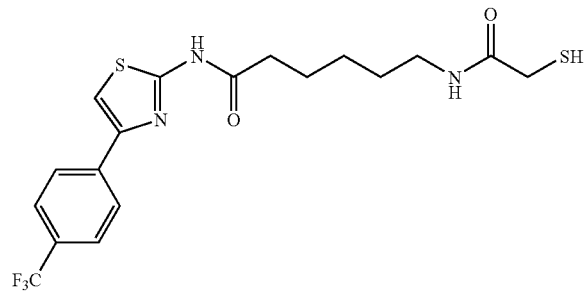 [SMILES: O=C(CS)NCCCCCC(=O)Nc1nc(-c2ccc(C(F)(F)F)cc2)cs1]

may be specifically excluded.

In any of the forgoing embodiments may

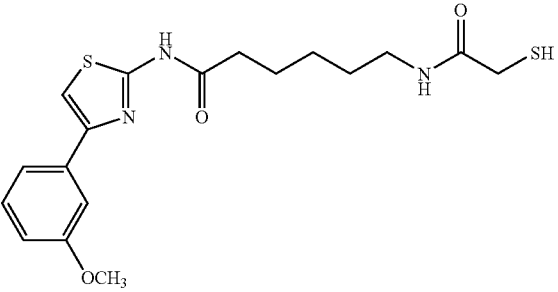 [SMILES: COc1cccc(-c2csc(NC(=O)CCCCCNC(=O)CS)n2)c1]

may be specifically excluded.

In any of the forgoing embodiments

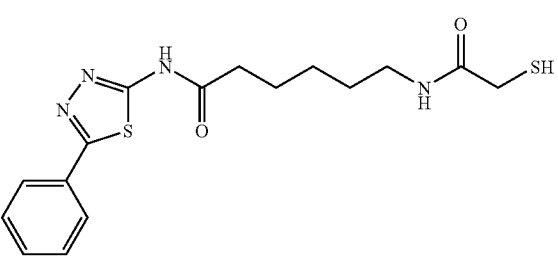 [SMILES: O=C(CS)NCCCCCC(=O)Nc1nnc(-c2ccccc2)s1]

may be specifically excluded.

In any of the forgoing embodiments

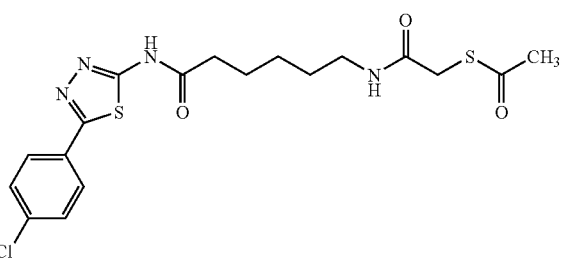

may be specifically excluded.

In addition, any compound cited in the references incorporated herein may also be specifically excluded from any of the forgoing embodiments.

As mentioned above, the compounds of the invention can be formulated as pharmaceutically acceptable salts. The phrase "pharmaceutically acceptable salt," as used herein, refers to a pharmaceutically acceptable organic or inorganic acid or base salt of an organic chemical compound. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p toluenesulfonate, salicylate, stearate, subacetate, succinate, sulfate, sulfosaliculate, suramate, tannate, tartrate, teoclate, tosylate, triethiodide, and valerate salts. The counterion may be any organic or inorganic moiety that stabilizes the charge on the parent compound. Furthermore, a pharmaceutically acceptable salt may have more than one charged atom in its structure. In this instance the pharmaceutically acceptable salt can have multiple counterions. Hence, a pharmaceutically acceptable salt can have one or more charged atoms and/or one or more counterions. Further examples of pharmaceutically acceptable salts are discussed in Berge et al. "Pharmaceutically Acceptable Salts," *J. Pharm. Sci.* 1977, 66, 1-19, hereby incorporated by reference in its entirety.

Selected Methods of the Invention

The invention further provides a method for increasing the sensitivity of a cancer cell to the cytotoxic effects of radiotherapy, comprising contacting said cell with an effective amount of a compound of any one of compounds of the invention in an amount sufficient to increase the sensitivity of said cell to the cytotoxic effects of radiotherapy.

In certain embodiments, the present invention relates to the aforementioned method, wherein said cell is an in vivo cell.

The invention also provides a method for treating cancer, said method comprising the steps of: administering to a subject in need thereof a therapeutically effective amount of a compound of the invention, or a pharmaceutically acceptable salt, solvate, derivative or prodrug thereof.

The invention also provides a method for treating Non-Hodgkin's lymphoma, Hodgkin's disease, Ewing's sarcoma, testicular cancer, prostate cancer, larynx cancer, cervical cancer, nasopharynx cancer, breast cancer, colon cancer, pancreatic cancer, head and neck cancer, esophageal cancer, rectal cancer, small-cell lung cancer, non-small cell lung cancer, brain cancer, or a CNS neoplasm, comprising administering to a subject in need thereof a compounds of the invention, or a pharmaceutically acceptable salt, solvate, derivative or prodrug thereof.

The invention also provides a method for treating a neurological disease, comprising administering to a subject in need thereof a therapeutically effective amount of a compound of the invention, or a pharmaceutically acceptable salt, solvate, derivative or prodrug thereof.

The invention also provides a method for treating Huntington's disease, lupus, or schizophrenia, comprising administering to a subject in need thereof a therapeutically effective amount of a compound of the invention, or a pharmaceutically acceptable salt, solvate, derivative or prodrug thereof.

In certain embodiments, the present invention relates to the aforementioned method, wherein said subject is a human.

In certain embodiments, the present invention relates to the aforementioned method, further comprising administering to said subject a therapeutically effective amount of radiotherapy.

The invention also provides a method for treating malaria, comprising the step of: administering to a subject in need thereof a therapeutically effective amount of a compound of the invention, or a pharmaceutically acceptable salt, solvate, derivative or prodrug thereof.

In certain embodiments, the present invention relates to the aforementioned method, wherein said subject is a human.

In certain embodiments, the present invention relates to the aforementioned method, further comprising co-administering to said subject an antimalarial compound selected from the group consisting of aryl amino alcohols, cinchona alkaloids, 4-aminoquinolines, type 1 or type 2 folate synthesis inhibitors, 8-aminoquinolines, antimicrobials, peroxides, naphthoquinones and iron chelating agents.

In certain embodiments the present invention relates to the aforementioned method, further comprising co-administering to said subject an antimalarial compound selected from the group consisting of quinine, quinidine, mefloquine, halofantrine, chloroquine, amodiaquine, proguanil, chloroproguanil, pyrimethamine, primaquine, 8-[(4-amino-1-methylbutyl)amino]-2,6-dimethoxy-4-methyl-5-[(3-trifluoromethyl)phenoxy]quinoline succinate (WR238,605), tetracycline, doxycycline, clindamycin, azithromycin, fluoroquinolones, artemether, arteether, artesunate, artelinic acid, atovaquone, and desferrioxamine.

In certain embodiments, the present invention relates to the aforementioned method, wherein said antimalarial compound is chloroquine.

In certain embodiments, the present invention relates to the aforementioned method, wherein said antimalarial compound is chloroquine; and said HDAC inhibitor is

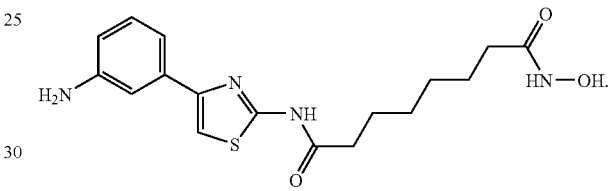

Preparation of Selected Compounds of the Invention

Figure 2:
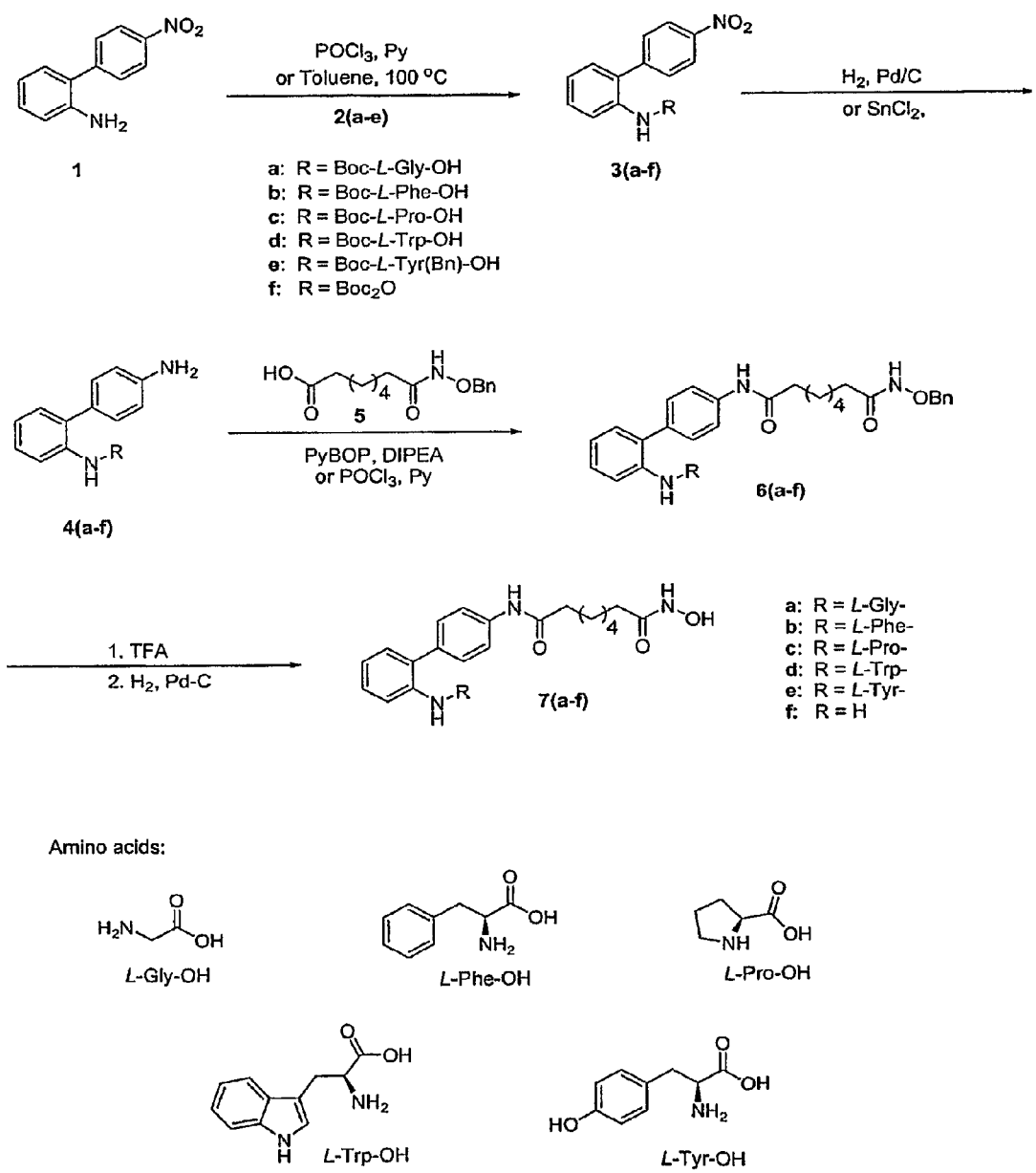
FIG. 2 depicts the synthesis of selected biphenyl hydroxamic acid compounds of the invention.
Figure 5:
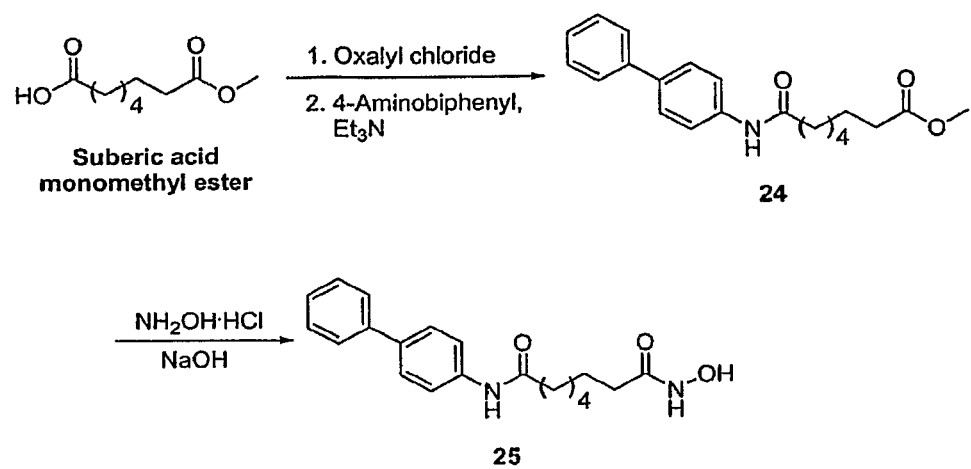
FIG. 5 depicts the synthesis of biphenyl bearing hydroxamate 25.

Synthesis of the biphenyl hydroxamic acid series outlined in FIG. 2 started from 4'-nitro-bipheny-2-ylamine (1) prepared from commercially available biphenyl-2-ylamine according to known procedure, then coupled with the protected amino acids 2(a-e) using POCl$_3$ in dry pyridine to give corresponding amides 3(a-e). G. D. Mendenhall, D. L. Smith, *Organic Synthesis* 1966, 46, 85. The reaction of compound 1 with di-tert-butyl dicarbonate in toluene at 100° C. led to the compound 3f. Reduction of the nitro group was achieved by Pd(OH)$_2$ catalyzed hydrogenation or in case of the intermediate 3e, by using tin(II) chloride to avoid undesirable O-benzyl group cleavage. The resulting biphenylamines 4a-f were treated with 7-benzyloxycarbamoyl heptanoic acid (5) under standard coupling conditions to afford the corresponding amides 6a-f. Acid deprotection followed by hydrogenation led to the hydroxamates 7a-f. S. Wittich, H. Scherf, C. Xie, G. Brosch, P. Loidl, C. Gerhauser, M. Jung, *J. Med. Chem.* 2002, 45, 3296; and D. T. S. Rijkers, H. P. H. M. Adams, H. C. Hemker, G. I. Tesser, *Tetrahedron* 1995, 51, 11235. The synthesis of related biphenyl bearing hydroxamate 25 lacking the ortho-substituent on the terminal ring was carried out as shown in FIG. 5. This known compound was prepared in order to better gauge the contribution that the ortho-substituent makes to HDAC inhibitory activity.

Figure 3:
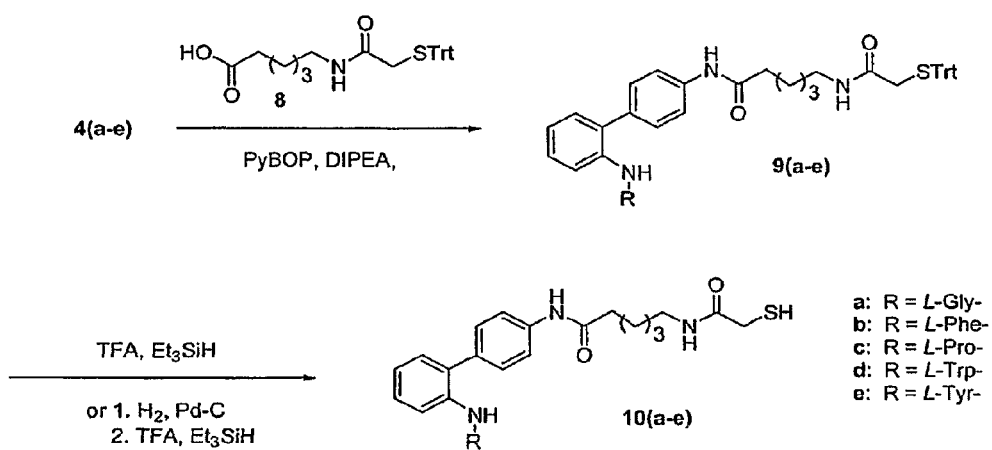
FIG. 3 depicts the synthesis of selected biphenyl mercaptoacetamide compounds of the invention.

The biphenyl mercaptoacetamides were prepared according to FIG. 3. The protected biphenyl amines 4a-e were coupled with the known 7-(2-tritylsulfanylacetylamino)heptanoic acid (8) in the presence of PyBOP and DIPEA. B. Chen, P. A. Petukhov, M. Jung, A. Velena, E. Eliseeva, A. Dritschilo, A. P. Kozikowski, *Bioorg. Med. Chem. Lett.* 2005, 15, 1389. One pot deprotection of both the trityl and Boc groups from the intermediates 9a-d using TFA/triethylsilane afforded the desired mercaptoacetamides 10a-d. Hydrogenolysis of the benzyl group from 9e, followed by treatment with TFA/triethylsilane gave the desired mercaptoacetamide 10e.

Figure 4:
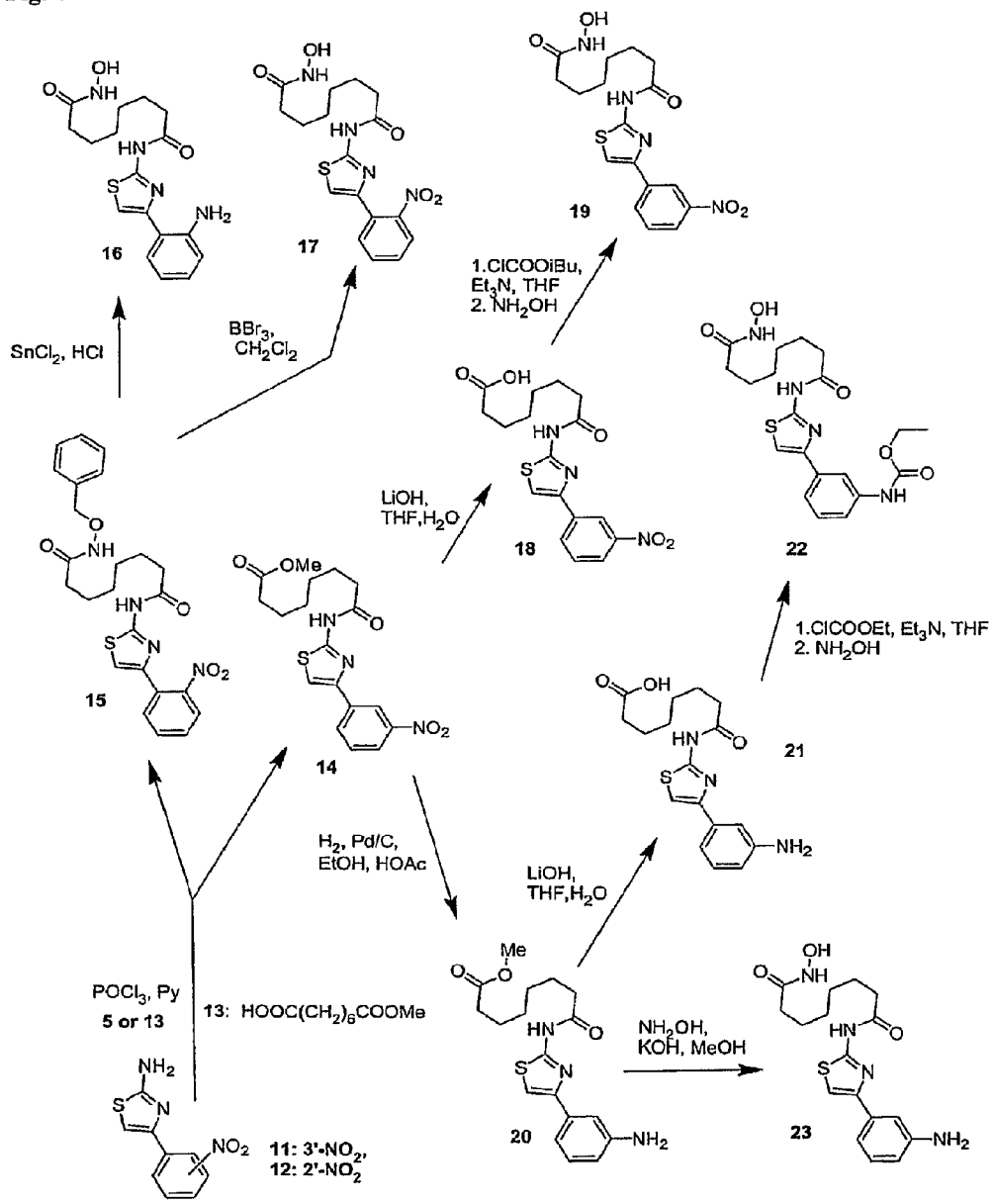
FIG. 4 depicts the synthesis of selected phenylthiazole hydroxamic acid compounds of the invention.

The preparation of several 2- and 3-substituted phenylthiazoles is detailed in FIG. 4. Details of the synthetic reaction for the phenylthazoles, along with the other compounds mentioned above, is provided in the Exemplification below.

Selected Biological Assays

Figure 6:
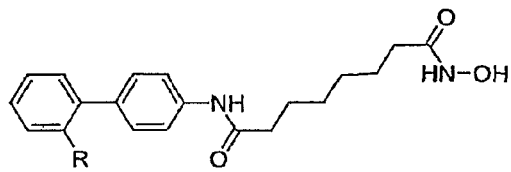
FIG. 6 depicts in vitro HDAC inhibitory activity of various biphenyl and phenylthiazole bearing hydroxamates, or mecaptoacetamides. For comparison, the IC$_{50}$ of suberoylanilide hydroxamic acid (SAHA) is 80 nM.
Figure 7:
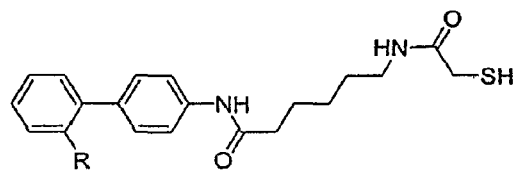
FIG. 7 depicts in vitro HDAC inhibitory activity of various biphenyl and phenylthiazole bearing hydroxamates, or mecaptoacetamides. For comparison, the IC$_{50}$ of suberoylanilide hydroxamic acid (SAHA) is 80 nM.
Figure 8:
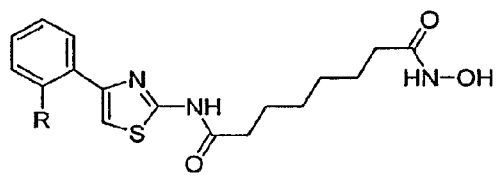
FIG. 8 depicts in vitro HDAC inhibitory activity of various biphenyl and phenylthiazole bearing hydroxamates, or mecaptoacetamides. For comparison, the IC$_{50}$ of suberoylanilide hydroxamic acid (SAHA) is 80 nM.
Figure 8:
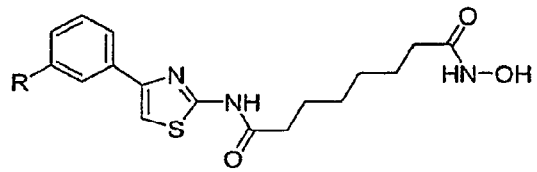

The in vitro HDAC inhibitory activity of the synthesized compounds was determined by using HDAC Fluor-Lys as the substrate (BIOMOL). (Additional assays for HDAC activity are given in US Patent Application 2002/0177594; hereby incorporated by reference). In FIGS. 6-8, the data are displayed as the concentration that is required to achieve 50% inhibition of HDAC activity ($IC_{50}$). SAHA was used as a positive control. Interestingly, all five of the amino acid bearing biphenyl hydroxamates turned out to be relatively potent HDAC inhibitors. Among them, the tryptophan and tyrosine derivatives showed $IC_{50}$ values of 30 nM and 50 nM respectively. Both of these compounds are more potent than SAHA, which gave an $IC_{50}$ value of 80 nM in the same assay.

However, it is to be noted that the unsubstituted biphenyl analog 25 has an $IC_{50}$ of 55 nM. The phenylalanine and proline derivatives were found to be approximately equipotent in their activity to SAHA, while the glycine derivative is weaker, with an $IC_{50}$ value of 200 nM. These data reveal that the hydroxamates linked to an amino acid bearing biphenyl cap residue are able to act as reasonably potent HDAC inhibitors, however, the amino acid substitutents do not have a pronounced effect on enzyme inhibitory activity as revealed by the activity of compound 25. The data presented herein indicate that the HDAC enzyme is able to tolerate varying appendages (e.g., amino acids) attached to the biphenyl scaffold. Other modifications along these lines including the use of unnatural amino acids may lead to further improvements in HDAC inhibitory activity. In addition, this appendage can be used to control isozyme selectivity, and maybe tissue distribution.

Compared to the corresponding hydroxamates 7a-e, the mercaptoacetamide derivatives 10a-e showed only weak or no inhibitory activity toward the HDAC enzyme. The best mercaptoacetamide was the proline containing derivative 10c, with an $IC_{50}$ value of 1.5 µM, while the phenylalanine and glycine derivatives exhibited weaker inhibitory activities of 3 µM and 7 µM, respectively. The tyrosine and tryptophan derivatives were inactive at concentrations of 1 µM. See related studies in: B. Chen, P. A. Petukhov, M. Jung, A. Velena, E. Eliseeva, A. Dritschilo, A. P. Kozikowski, *Bioorg. Med. Chem. Lett.* 2005, 15, 1389; and M. Jung, A. Velena, B. Chen, P. A. Petukhov, A. P. Kozikowski, A. Dritschilo, *Radiat. Res.* 2005, 163, 488; both of which are hereby incorporated by reference.

The use of a phenylthiazole as the CAP for HDAC inhibitors has previously been reported by Glazer et al. (Glaser, K. B. et al. "Differential protein acetylation induced by novel histone deacetylase inhibitors," *Biochem. Biophys, Research Comm.* 2004, 325, 683-690; which is hereby incorporated by reference) using an α-ketoamide as the zinc chelating group. As is readily apparent from FIG. 8, the amine bearing phenylthiazole 16 is poorly active, a finding that may relate to the inability of the two rings in these structures to adopt an approximately coplanar arrangement, as suggested by modeling studies (data not shown). Its nitro containing counterpart compound 17 is reasonably potent with an $IC_{50}$ of 50 nM. On the other hand, the other three phenylthiazoles possessing a nitrogen substitutent at the meta position of the phenyl ring are the most potent compounds in this series, with the carbamate derivative 22 exhibiting an $IC_{50}$ value of 5 nM. This relatively simple hydroxamate is thus approximately two-fold more potent than the natural product trichostatin A that has a reported $IC_{50}$ of 12 nM. The non-acylated 3-aminophenylthiazole is also potent, with and $IC_{50}$ of 8 nM.

Antiproliferative Activity

One of characteristics of the HDAC inhibitors relates to their ability to inhibit the growth of transformed cells. The compounds capable of modifying histones in the cell were tested for their biological effects. The more active hydroxamate- and mercaptoacetamide-based inhibitors were evaluated in cellular assays for their antiproliferative activity against prostate cancer (PC-3), breast cancer (MCF-7), cervical cancer (HeLa), and squamous carcinoma (SQ-20B) (FIG. 9a). The $IC_{50}$s for the hydroxamates ranged from 0.1 µM to >60 µM, while the mercaptoacetamides 10a-c showed weaker inhibitory activity in all three cancer cell lines (not tested in HeLa). Among the compounds tested, the phenylalanine bearing hydroxamate 7b displayed good growth inhibitory activity against the four cancer cell lines. Its activity was comparable to the activity shown by SAHA. Interestingly, some of these compounds were also tested in normal cells, such as human normal fibroblasts (NHP-5) and human normal primary skin fibroblasts (Hs-68), and these cell lines were found to be significantly resistant to the HDACIs. Thus, 7a showed $IC_{50}$ values of >500 µM in both cell lines, 7b had $IC_{50}$s of 80 and >300 µM, respectively, and 7d had an $IC_{50}$ of 100 µM against NHP-5, thus suggesting that these compounds exhibit an important element of selectivity in inhibiting the growth of transformed cells. Of all the compounds tested, the unsubstituted biphenyl analog 25 and the three meta-substituted phenylthiazoles 19, 22 and 23 show submicromolar activity against the majority of the cancer cell lines tested. In keeping with the greater HDAC inhibitory activity of 22, this compound showed impressive antiproliferative activity.

Isoform Selectivity

To test whether the modified CAP region of the HDACIs is able to target specific HDAC isoform enzyme activity, the compounds were examined for class I HDAC isoform inhibitory activities using recombinant HDAC8 and immunoprecipitates of the other HDAC isoforms (HDAC 1, 2, 3) using nuclear extracts from HeLa cells. Overall, and as found above, the compounds bearing a hydroxamate group showed better HDAC inhibitory activity than those containing the mercaptoacetamide unit as the zinc chelator. The data shown in FIG. 10 represent the HDAC inhibitory activity remaining after addition of 0.5 µM of the test compounds. SAHA shows little selectivity for the four isozymes, while TSA is more effective for inhibiting HDACs 1 and 2. As is evident from a perusal of FIG. 10, the more interesting activity is demonstrated by the HDACIs containing the phenylthiazole CAPs. In particular, compounds 19, and 23 show a strong tendency to inhibit the activity of HDACs 1 and 2, while more than 30% activity remains at HDACs 3 and 8. This trend is also shown by the unsubstituted biphenyl analog 25.

In certain embodiments, the present invention relates to the aforementioned compound, wherein the compounds of the invention are selective HDAC class 1 inhibitors. In other embodiments, the present invention relates to the aforementioned compound, wherein the compounds of the invention are selective HDAC class 2 inhibitors.

Modeling Studies

To explore the putative binding modes of the ligands 7a-e, they were docked to the binding site of HDAC8 and scored using the FlexX and CScore modules in SYBYL7.1. Although all scoring functions were relatively successful in positioning SAHA in the correct pose in the binding site, only a combination of Chemscore and a consensus of two scoring functions FlexX and GOLD were successful in placing both the hydroxamate and the CAP group of SAHA close to their positions found in the x-ray. In the docked pose, the CAP group of SAHA adjusts its position so as to improve the geometry of the hydrogen bond between the NH of the ligand and Asp101 and shifts the position of the phenyl ring so as to bury it underneath Tyr100, thereby decreasing the loss in binding energy stemming from poor solvation of SAHA's hydrophobic phenyl group. The RMS difference between the docked conformation of SAHA and that found in x-ray is within the resolution of the x-ray structure, less than 2.91 Å, indicating that this docking protocol is acceptable for further docking studies of the ligands 7a-e. Since inhibitory data are available for a relatively small number of compounds, a quantitative comparison of the scores of these ligands is unreliable, and thus, only the description of their binding modes is presented below.

Figure 11:
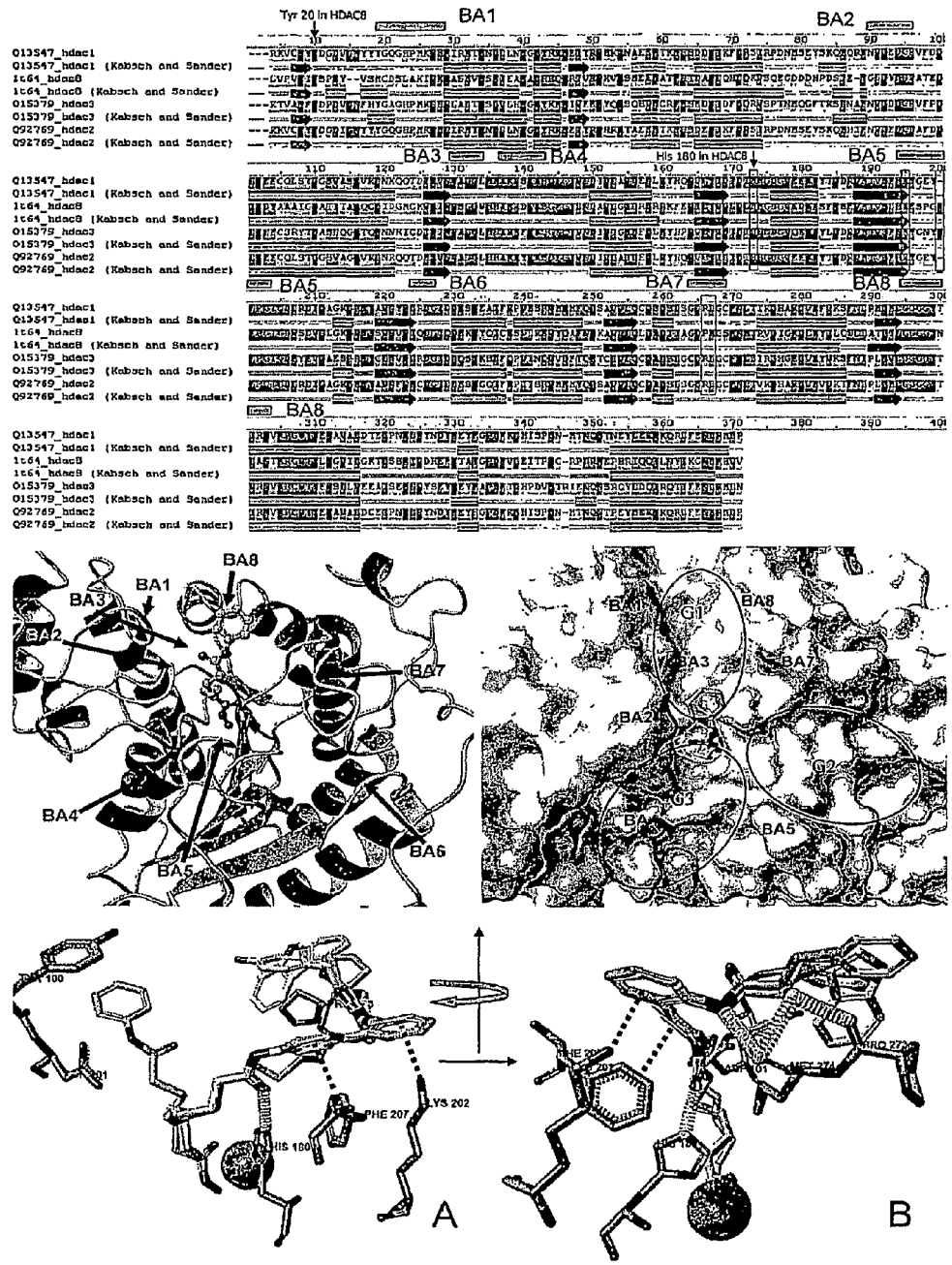
FIG. 11 depicts (top) the alignment of HDAC1-3 (only the sequences corresponding to the amino acid residues appearing in the x-ray crystal structure of HDAC8 and used in the homology modeling are shown). The sequence alignment of the full sequences can be found in J. R. Somoza, R. J. Skene, B. A. Katz, C. Mol, J. D. Ho, A. J. Jennings, C. Luong, A. Arvai, J. J. Buggy, E. Chi, J. Tang, B. C. Sang, E. Verner, R. Wynands, E. M. Leahy, D. R. Dougan, G. Snell, M. Navre, M. W. Knuth, R. V. Swanson, D. E. McRee, L. W. Tari, *Structure (Camb.)* 2004, 12, 1325; and M. S. Finnin, J. R. Donigian, A. Cohen, V. M. Richon, R. A. Rifkind, P. A. Marks, R. Breslow, N. P. Pavletich, *Nature* 1999, 401, 188). The secondary structure (Kabsch and Sander) is designated using red stripes (α-helix) and blue arrows (β-sheet). The binding areas (BAs) that are of potential interest for targeting specific HDAC class I isoforms are marked by green stripes (the numbering is shifted in comparison to that shown in the original sequences). Identical residues found in all HDAC isoforms are shown in the figure in dark blue, residues with strong similarity are in blue, residues with low similarity are in light blue, and non matching residues are grey.
Figure 12:
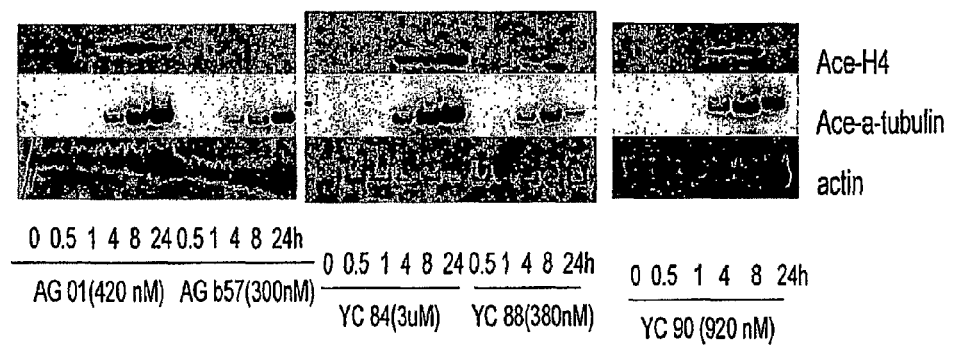
FIG. 12 depicts the effects of HDACi on the expression of p21, Ace-H4 and Ace-a-tubulin. Note that AG 01 is 26, AG b57 is 7f, YC 84 is 25, YC 88 is 23 and YC 90 is 19.
Figure 13:
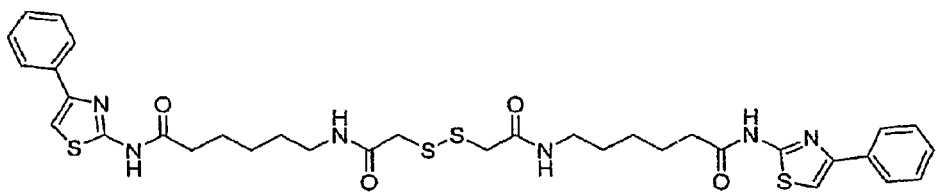
FIG. 13 depicts in vitro HDAC inhibitory activity and antiproliferation activities for 27 and 28. Note: ND is an abbreviation for "Not Determined."
Figure 13:
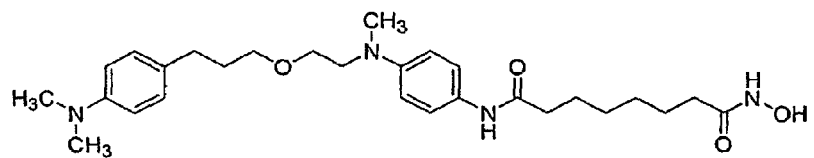
Figure 14:
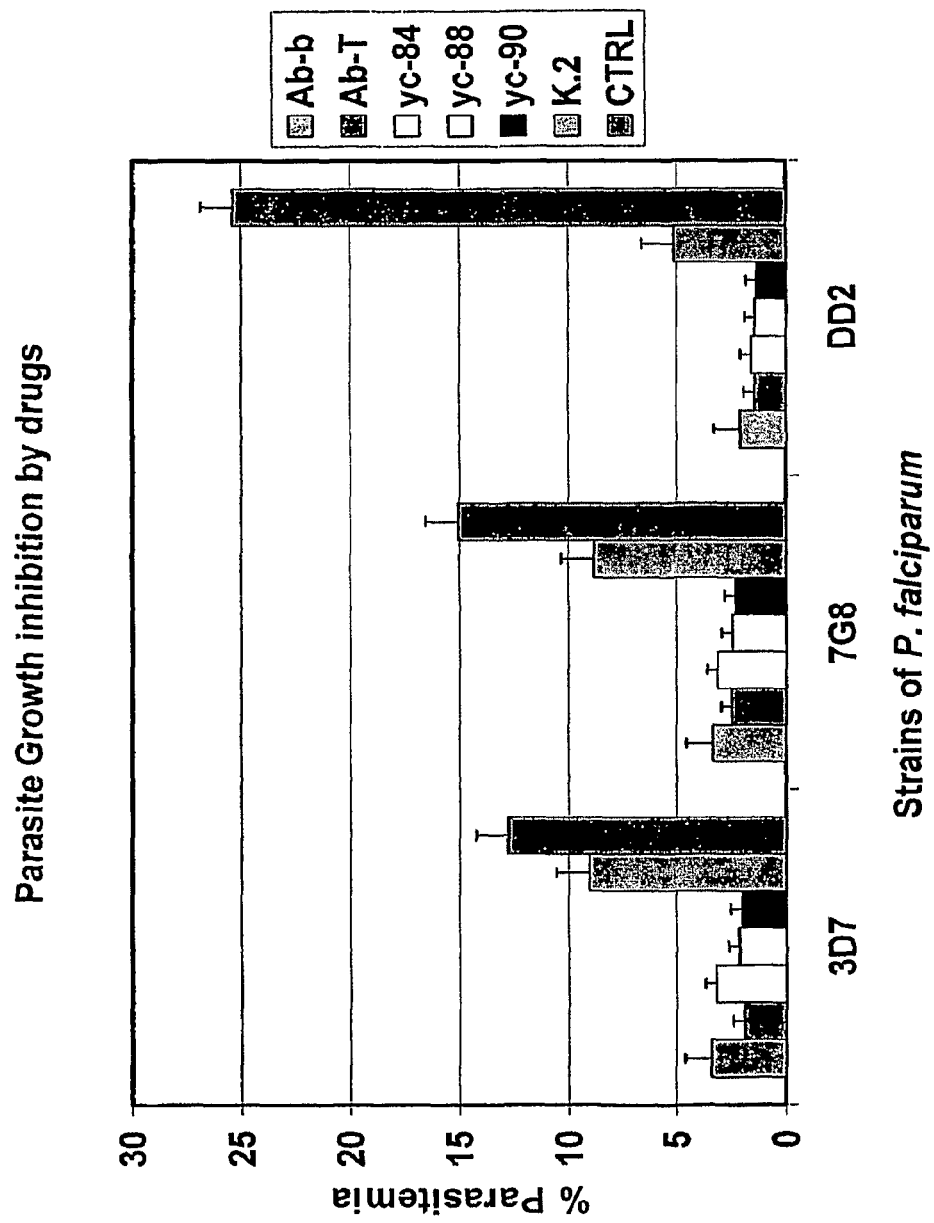
FIG. 14 depicts a graph showing percent of parasitemia present after treatment with compounds of the invention. Results for 3D7, 7G8 and DD2 are shown. Note that Ab-b is 7f, Ab-t is 26, yc-84 is 25, yc-90 is 19, and yc-88 is 23.
Figure 15:
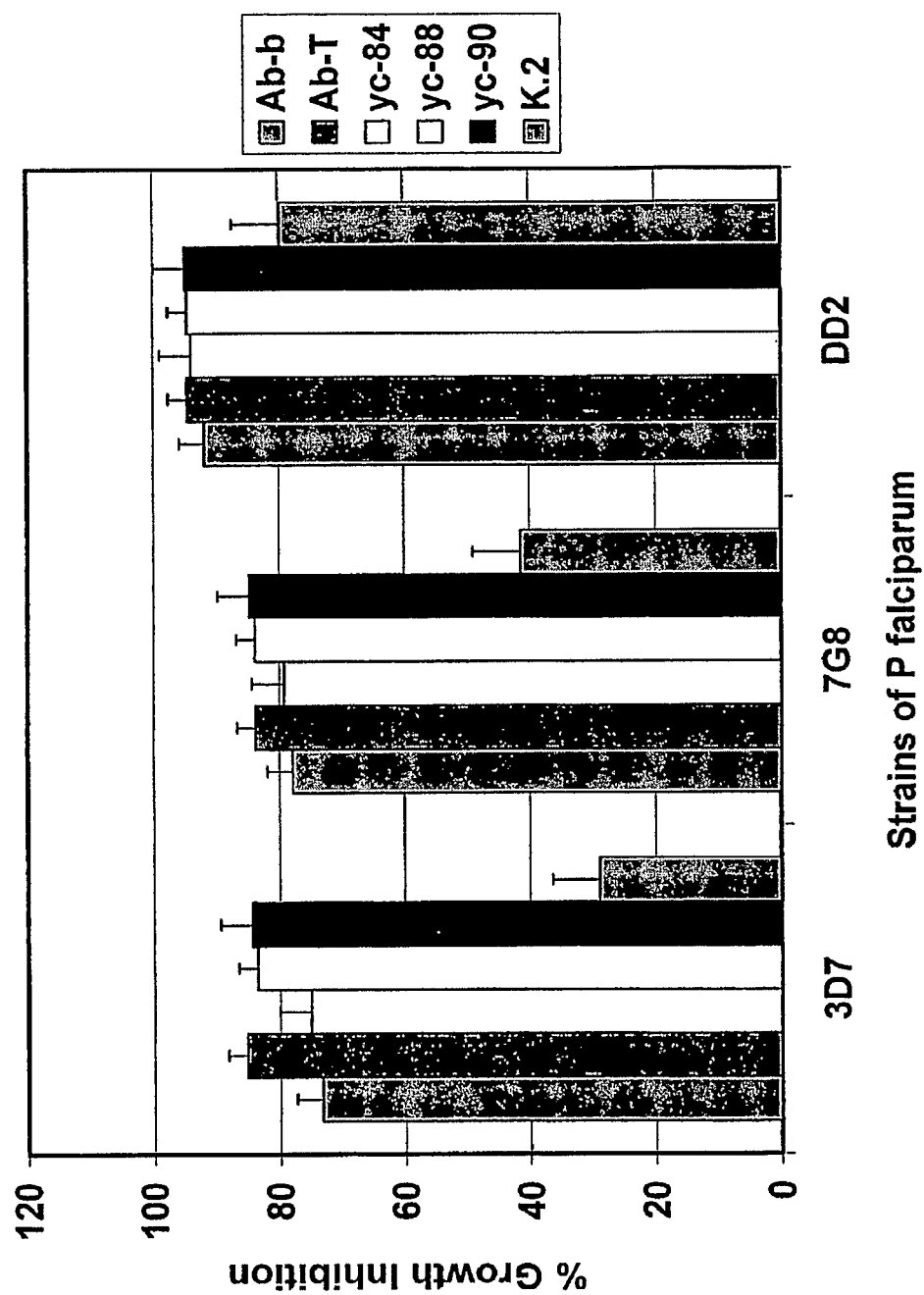
FIG. 15 depicts a graph showing parasite growth inhibition by compounds of the invention. Results for 3D7, 7G8 and DD2 are shown. Note that Ab-b is 7f, Ab-t is 26, yc-84 is 25, yc-90 is 19, and yc-88 is 23.
Figure 16:
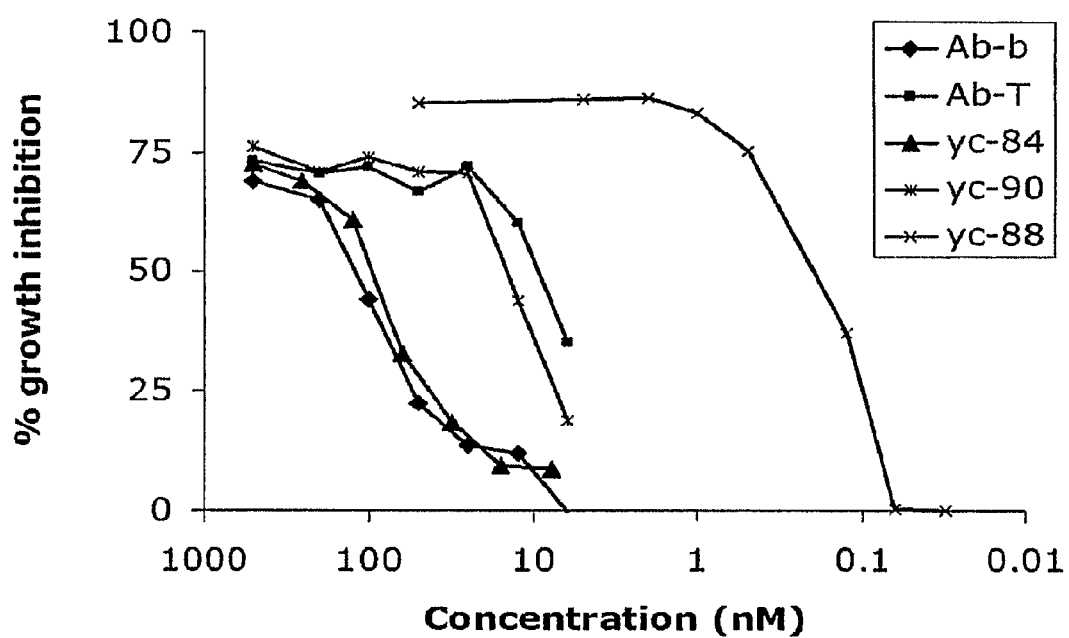
FIG. 16 depicts a graph showing the resulting percent inhibition in the growth of 7G8 parasites due to incubation, for 56 hours, with selected compounds of the invention. Note that Ab-b is 7f, Ab-t is 26, yc-84 is 25, yc-90 is 19, and yc-88 is 23.
Figure 17:
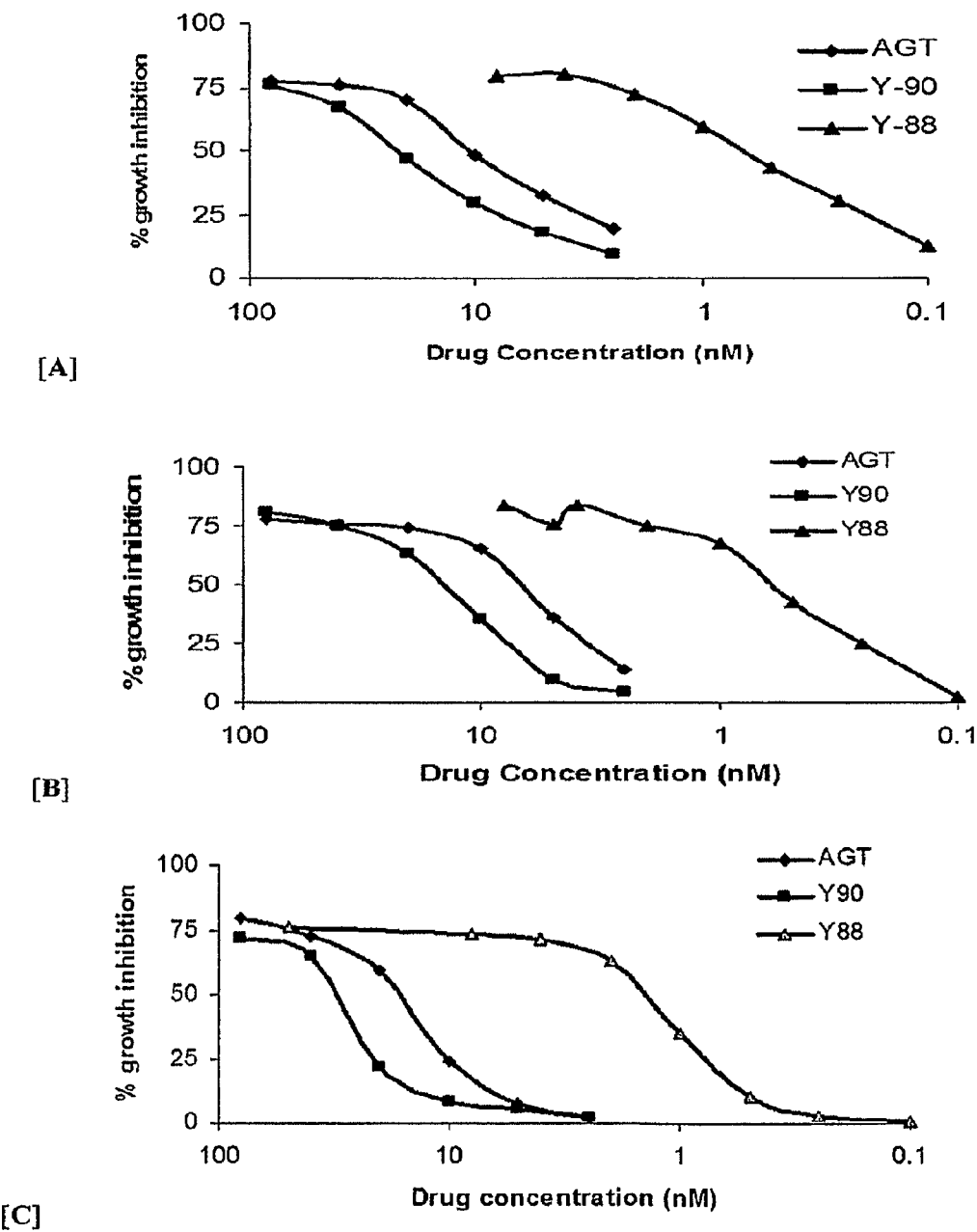
FIG. 17 depicts three graphs showing the resulting percent inhibition in the growth of FRC-3 parasites [A], DD2 parasites [B], or 3D7 parasites [C], due to incubation, for 56 hours, with selected compounds of the invention. Note that AGT is 26, yc-90 is 19, and yc-88 is 23. In all three graphs, the results shown are the average of two experiments.
Figure 19:
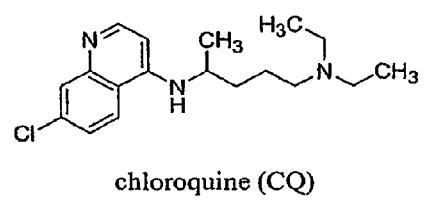
FIG. 19 depicts the structure of chloroquine (CQ), the structure of K2, and a graph showing the resulting percent inhibition in the growth of FCB-1 parasites in the presence of CQ, CQ with 40 nM of K2, and CQ with 80 nM of K2.
Figure 19:
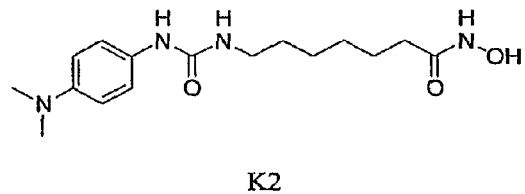
Figure 19:
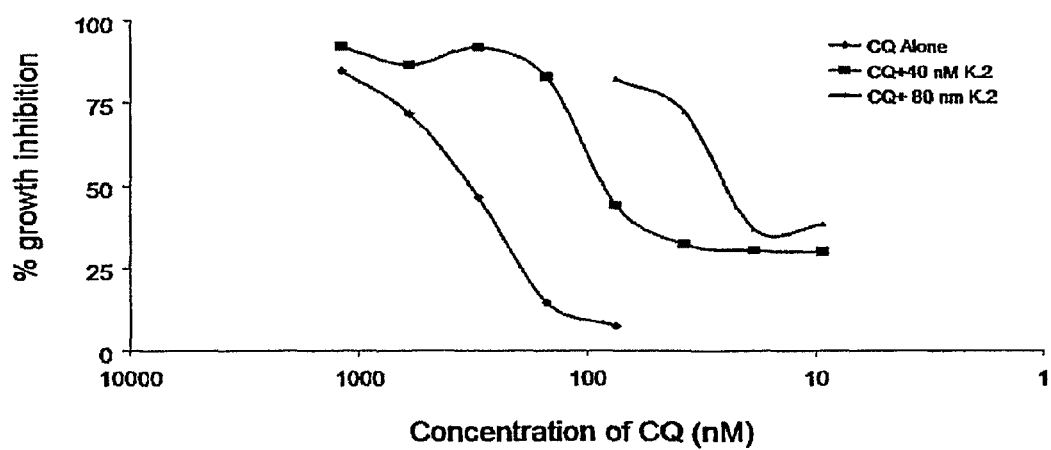
Figure 21:
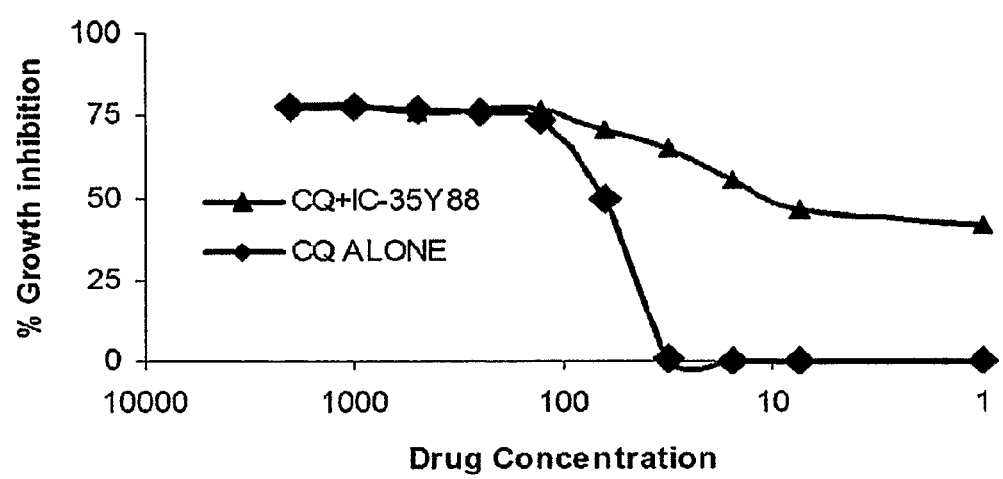
FIG. 21 depicts a graph showing the resulting percent inhibition in the growth of DD2 parasites due to incubation with chloroquine (CQ) and Y88 (23).

Visual analysis of the putative binding modes suggested by the Chemscore and a consensus of two scoring functions shows that the ligands have the same binding modes. This is hardly surprising as the only difference among 7a-e relates to the nature of the amino acid sidechain present in the CAP region. The carbonyl group of the amide bond of all ligands appears to form a hydrogen bond with His180. Unlike the phenyl ring of SAHA, which does not have any defined interactions with the binding site, the biphenyl system of 7a-e can form two interactions: the first phenyl ring of the biphenyl group forms a weak CH-$\pi$ hydrogen bond (edge-to-face interaction) with the $\pi$-electrons of Phe207 (FIG. 11), whereas the second phenyl ring forms a cation-$\pi$ interaction with the charged amino group of Lys202. Both Phe207 and Lys202 are located in the groove G2 formed by the loop/binding area BA5 (see FIG. 11) for definition of the binding areas and grooves). The amido and the amino groups of the amino acid fragment of 7a-e form two hydrogen bonds with the carbonyl groups of Pro273 and Met274; these two amino acids form the top part of BA7. The lipophilic portions of the sidechains of the amino acid groups in ligands 7b-e engage in hydrophobic contacts with the lipophilic sidechains of Pro273 and Met274. The polar portions of the Trp and Tyr sidechains of 7d and 7e, respectively, point toward the solvent and do not form any interactions with the protein. Therefore, none of the ligands has a binding mode that can be considered to be dramatically different from the other. This is consistent with the similar HDAC8 inhibitory activity found for 7a-e. Moreover, it appears that the extra groups added to the CAP region of the ligands are well tolerated, as the activity of the new ligands is similar to that of SAHA.

Pharmaceutical Compositions and Therapeutic Administration

In certain aspects, the present invention provides a pharmaceutical composition comprising an effective amount of a Compound of the Invention and a pharmaceutically acceptable carrier or vehicle. The pharmaceutical compositions are suitable for veterinary or human administration.

The pharmaceutical compositions of the present invention can be in any form that allows for the composition to be administered to a subject, said subject preferably being an animal, including, but not limited to a human, mammal, or non-human animal, such as a cow, horse, sheep, pig, fowl, cat, dog, mouse, rat, rabbit, guinea pig, etc. In a preferred embodiment, the subject is a mammal, and most preferably a human.

The compositions of the invention can be in the form of a solid, liquid or gas (aerosol). Typical routes of administration may include, without limitation, oral, topical, parenteral, sublingual, rectal, vaginal, ocular, and intranasal. Parenteral administration includes subcutaneous injections, intravenous, intramuscular, intraperitoneal, intrapleural, intrasternal injection or infusion techniques. The compositions may be administered parenterally. The compositions may be administered intravenously. Pharmaceutical compositions of the invention can be formulated so as to allow a Compound of the Invention to be bioavailable upon administration of the composition to a subject. Compositions can take the form of one or more dosage units, where, for example, a tablet can be a single dosage unit, and a container of a Compound of the Invention in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the overall health of the subject, the type of cancer the subject is in need of treatment of, the use of the composition as part of a multi-drug regimen, the particular form of the Compound of the Invention, the manner of administration, and the composition employed.

The pharmaceutically acceptable carrier or vehicle may be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, e.g., inhalatory administration.

The composition may be intended for oral administration, and if so, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as ethyl cellulose, carboxymethylcellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the pharmaceutical composition is in the form of a capsule, e.g., a gelatin capsule, it can contain, in addition to materials of the above type, a liquid carrier such as polyethylene glycol, cyclodextrin or a fatty oil.

The pharmaceutical composition can be in the form of a liquid, e.g., an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in ampoule, a disposable syringe or a multiple-dose vial made of glass, plastic or other material. Physiological saline is a preferred adjuvant. An injectable composition is preferably sterile.

The amount of the Compound of the Invention that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The pharmaceutical compositions comprise an effective amount of a Compound of the Invention such that a suitable dosage will be obtained. Typically, this amount is at least 0.01% of a Compound of the Invention by weight of the composition. When intended for oral administration, this amount can be varied to be between 0.1% and 80% by weight of the composition. Preferred oral compositions can comprise from between 4% and 50% of the Compound of the Invention by weight of the composition. Preferred compositions of the present invention are prepared so that a parenteral dosage unit contains from between 0.01% and 2% by weight of the Compound of the Invention.

Generally, the dosage of a Compound of the Invention administered to a subject is typically between 0.1 mg/kg and 100 mg/kg of the subject's body weight. In one embodiment, the dosage administered to a subject is between 0.5 mg/kg and 50 mg/kg of the subject's body weight, more preferably between 1 mg/kg and 25 mg/kg of the subject's body weight.

In a specific embodiment, when the Compounds of the Invention are used in combination with radiotherapy, a Compound of the Invention can be administered in amounts that result in concentrations in the fluid of a target tissue that are less than about twice the $IC_{50}$ concentration for the particular compound, more preferably about equal to the $IC_{50}$ concentration. The $IC_{50}$ concentration is defined as the concentration of the Compound of the Invention that kills 50% of cells following treatment with the Compound of the Invention.

In another embodiment, the Compounds of the Invention may be administered at amounts lower than the $IC_{50}$ concentration, such as about 50% of the $IC_{50}$ concentration, about 40% of the $IC_{50}$ concentration, about 30% of the $IC_{50}$ concentration, about 20% of the $IC_{50}$ concentration, about 10% or about 5% of the $IC_{50}$ concentration, at the target tissue.

In still another embodiment; the Compounds of the Invention may be administered locally so that the concentration at the target tissue is in the effective range and the concentration in non-target tissue is minimized.

In another embodiment, the dosage of the Compound of the Invention results in a concentration at a target tissue that does not promote apoptosis of cells in culture yet is effective in increasing cell death in neoplastic cells exposed to radiation or recognized chemotherapeutic chemical agents. Concentrations that produce these effects can be determined for a Compound of the Invention by one of skill in the art using markers of apoptosis, including, but not limited to, the apoptotic index and caspase activities.

The Compounds of the Invention can be administered by any convenient route, for example by infusion or bolus injection, by absorption through epithelial or mucocutaneous linings (e.g., oral mucosa, rectal and intestinal mucosa, etc.). Administration can be systemic or local. Various delivery systems are known, e.g., microparticles, microcapsules, capsules, etc., and may be useful for administering a Compound of the Invention. In certain embodiments, more than one Compound of the Invention is administered to a subject. Methods of administration may include, but are not limited to, oral administration and parenteral administration; parenteral administration including, but not limited to, intradermal, intramuscular, intraperitoneal, intravenous, subcutaneous; intranasal, epidural, sublingual, intranasal, intracerebral, intraventricular, intrathecal, intravaginal, transdermal, rectally, by inhalation, or topically to the ears, nose, eyes, or skin. The preferred mode of administration is left to the discretion of the practitioner, and will depend in-part upon the site of the medical condition (such as the site of cancer, a cancerous tumor or a pre-cancerous condition).

In one embodiment, the Compounds of the Invention are administered orally.

In another embodiment, the Compounds of the Invention are administered parenterally.

In still another embodiment, the Compounds of the Invention are administered intravenously.

In specific embodiments, it can be desirable to administer one or more Compounds of the Invention locally to the area in need of treatment. This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as sialastic membranes, or fibers. In one embodiment, administration can be by direct injection at the site (or former site) of a cancer, tumor, or precancerous tissue. In certain embodiments, it can be desirable to introduce one or more Compounds of the Invention into the central nervous system by any suitable route, including intraventricular and intrathecal injection. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Compounds of the Invention can be formulated as a suppository, with traditional binders and carriers such as triglycerides.

In one embodiment, the Compounds of the Invention can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the Compounds of the Invention can be delivered in a controlled release system. In one embodiment, a pump can be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)). In yet another embodiment, a controlled-release system can be placed in proximity of the target of the Compounds of the Invention, e.g., the brain, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

The term "carrier" refers to a diluent, adjuvant or excipient, with which a Compound of the Invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a subject, the Compounds of the Invention and pharmaceutically acceptable carriers are sterile. Water is a preferred carrier when the Compound of the Invention is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable carrier is a capsule (see e.g., U.S. Pat. No. 5,698,155; hereby incorporated by reference). Other examples of suitable pharmaceutical carriers are described in "Remington's Pharmaceutical Sciences" by E. W. Martin, hereby incorporated by reference.

Sustained or directed release compositions that may be formulated include, but are not limited to liposomes or other formulations wherein the active component is protected with differentially degradable coatings, e.g., by microencapsulation, multiple coatings, etc. It is also possible to freeze-dry the new compositions and use the lyophilizates obtained, for example, for the preparation of products for injection.

In a preferred embodiment, the Compounds of the Invention are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a Compound of the Invention is to be administered by infusion, it can be dispensed, for example, with an infusion bottle containing sterile pharmaceutical grade water or saline. Where the Compound of the Invention is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving complex are also suitable for orally administered compositions of the invention. In these later platforms, fluid from the environment surrounding the capsule is imbibed by the driving complex, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard carriers such as mannitol, lactose, starch, magnesium stearate, sodium saccharine, cellulose, magnesium carbonate, etc. Such carriers are preferably of pharmaceutical grade.

The pharmaceutical compositions of the invention can be intended for topical administration, in which case the carrier can be in the form of a solution, emulsion, ointment or gel base. The base, for example, can comprise one or more of the following: petrolatum, lanolin, polyethylene glycols, beeswax, mineral oil, diluents such as water and alcohol, and emulsifiers and stabilizers. Thickening agents can be present in a composition for topical administration. If intended for transdermal administration, the composition can be in the form of a transdermal patch or an iontophoresis device. Topical formulations can comprise a concentration of a Compound of the Invention of from between 0.01% and 10% w/v (weight per unit volume of composition).

The compositions can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

The compositions can consist of gaseous dosage units, e.g., it can be in the form of an aerosol. The term aerosol is used to denote a variety of systems ranging from those of colloidal nature to systems consisting of pressurized packages. Delivery can be by a liquefied or compressed gas or by a suitable pump system that dispenses the active ingredients. Aerosols of the compositions can be delivered in single phase, bi-phasic, or tri-phasic systems in order to deliver the composition. Delivery of the aerosol includes the necessary container, activators, valves, subcontainers, Spacers and the like, which together can form a kit. Preferred aerosols can be determined by one skilled in the art, without undue experimentation.

Whether in solid, liquid or gaseous form, the compositions of the present invention can comprise an additional therapeutically active agent selected from among those including, but not limited to, an additional anticancer agent, an antiemetic agent, a hematopoietic colony stimulating factor, an antidepressant and an analgesic agent.

The pharmaceutical compositions can be prepared using methodology well known in the pharmaceutical art. For example, a composition intended to be administered by injection can be prepared by combining a Compound of the Invention with water so as to form a solution. A surfactant can be added to facilitate the formation of a homogeneous solution or suspension. Surfactants are complexes that can non-covalently interact with a Compound of the Invention so as to facilitate dissolution or homogeneous suspension of the Compound of the Invention in the aqueous delivery system.

In one embodiment, the pharmaceutical compositions of the present invention may comprise one or more additional anticancer agents.

In another embodiment, the pharmaceutical compositions of the present invention can be administered prior to, at the same time as, or after an additional anticancer agent, or on the same day, or within 1 hour, 2 hours, 12 hours, 24 hours, 48 hours, 72 hours, 1 week, 2 weeks, 3 weeks or 4 weeks of each other.

In one embodiment, the pharmaceutical compositions of the present invention may comprise one or more known therapeutically active agents.

In another embodiment, the pharmaceutical compositions of the present invention can be administered prior to, at the same time as, or after an antiemetic agent, or on the same day, or within 1 hour, 2 hours, 12 hours, 24 hours, 48 hours or 72 hours of each other.

In another embodiment, the pharmaceutical compositions of the present invention can be administered prior to, at the same time as, or after a hematopoietic colony stimulating factor, or on the same day, or within 1 hour, 2 hours, 12 hours, 24 hours, 48 hours, 72 hours, 1 week, 2 weeks, 3 weeks or 4 weeks of each other.

In another embodiment, the pharmaceutical compositions of the present invention can be administered prior to, at the same time as, or after an opioid or non-opioid analgesic agent, or on the same day, or within 1 hour, 2 hours, 12 hours, 24 hours, 48 hours or 72 hours of each other.

In another embodiment, the pharmaceutical compositions of the present invention can be administered prior to, at the same time as, or after an anti-depressant agent, or on the same day, or within 1 hour, 2 hours, 12 hours, 24 hours, 48 hours or 72 hours of each other.

Selected Kits of the Invention

The invention encompasses kits that can simplify the administration of the Compounds of the Invention or composition of the invention to a subject.

A typical kit of the invention comprises unit dosages of the Compounds of the Invention. In one embodiment, the unit dosage form is in a container, which can be sterile, containing an effective amount of one of the Compounds of the Invention and a pharmaceutically acceptable carrier or vehicle. In another embodiment, the unit dosage form is in a container containing an effective amount of one of the Compounds of the Invention as a lyophilate. In this instance, the kit can further comprise another container which contains a solution useful for the reconstitution of the lyophilate. The kit can also comprise a label or printed instructions for use of the Compounds of the Invention. In one embodiment, the kit comprises multiple containers: (a) a first container containing an unit dosage form of Compound of the Invention, and (b) one or more additional containers each containing a unit dosage form of one or more additional anticancer agents or pharmaceutically acceptable salts thereof. In another embodiment the kit comprises a container containing a therapeutically active agent such as an antiemetic agent, a hematopoietic colony-stimulating factor, an analgesic agent or an anxiolytic agent.

In a further embodiment, the kit comprises a unit dosage form of a pharmaceutical composition of the invention.

Kits of the invention can further comprise one or more devices that are useful for administering the unit dosage forms of the Compounds of the Invention or a pharmaceutical composition of the invention. Examples of such devices include, but are not limited to, a syringe, a drip bag, a patch or an enema, which optionally contain the unit dosage forms.

Anti-HDAC Applications

The present invention also provides active compounds which are anti-HDAC agents, and which treat a condition mediated by HDAC. The term "a condition mediated by HDAC," as used herein pertains to a condition in which HDAC and/or the action of HDAC is important or necessary, e.g., for the onset, progress, expression, etc. of that condition, or a condition which is known to be treated by HDAC inhibitors (such as, e.g., trichostatin (TSA), pivalolyloxymethylbutane (AN-9; Pivanex), FK-228 (Depsipeptide), PXD-101, NVP-LAQ824, suberoylohydroxamin acid (SAHA), MS-275, and or MGCD0103). Examples of such conditions include, but are not limited to, the following: cancer, psoriasis, fibroproliferative disorders (e.g., liver fibrosis), smooth muscle proliferative disorders (e.g., atherosclerosis, restenosis), neurodegenerative diseases (e.g., Alzheimer's, Parkinson's, Huntington's chorea, amyotropic lateral sclerosis, spino-cerebellar degeneration), inflammatory diseases (e.g., osteoarthritis, rheumatoid arthritis), diseases involving angiogenesis (e.g., cancer, rheumatoid arthritis, psoriasis, diabetic retinopathy), haematopoietic disorders (e.g., anaemia, sickle cell anaemia, thalassaeimia), fungal infections, parasitic infections (e.g., malaria, trypanosomiasis, helminthiasis, protozoal infections), bacterial infections, viral infections, and conditions treatable by immune modulation (e.g., multiple sclerosis, autoimmune diabetes, lupus, atopic dermatitis, allergies, asthma, allergic rhinitis, inflammatory bowel disease; and for improving grafting of transplants).

One of ordinary skill in the art is readily able to determine whether or not a candidate compound treats a condition mediated by HDAC for any particular cell type. For example, assays which may conveniently be used to assess the activity offered by a particular compound are described in the examples herein.

Treatment of Cancer

The Compounds of the Invention are useful for treating cancer. The Compounds of the Invention are also useful for increasing the sensitivity of a cancer cell to the cytotoxic effects of radiotherapy.

Cancer can be treated or prevented by administration of amounts of the Compounds of the invention that are effective to treat cancer or by administration of a pharmaceutical composition comprising amounts of the Compounds of the invention that are effective to treat cancer.

In a preferred embodiment, the present invention provides methods for treating cancer, including but not limited to: killing a cancer cell or neoplastic cell; inhibiting the growth of a cancer cell or neoplastic cell; inhibiting the replication of a cancer cell or neoplastic cell; or ameliorating a symptom thereof, said methods comprising administering to a subject in need thereof an amount of the Compounds of the invention effective to treat cancer.

In one embodiment, the invention provides a method for treating cancer, said method comprising administering to a subject in need thereof an amount of a Compound of the Invention or a pharmaceutically acceptable salt thereof, said amount sufficient to treat said cancer.

In another embodiment, the invention provides a method for increasing the sensitivity of a cancer cell to the cytotoxic effects of radiotherapy, said method comprising contacting said cell with a Compound of the Invention or a pharmaceutically acceptable salt thereof, in an amount sufficient to increase the sensitivity of said cell to the cytotoxic effects of radiotherapy.

In a further embodiment, the present invention provides a method for treating cancer, said method comprising: (a) administering to a subject in need thereof an amount of a Compound of the Invention; and (b) administering to said subject an amount of radiotherapy. In one embodiment, the amounts administered are each effective to treat cancer. In another specific embodiment, the amounts are together effective to treat cancer. The Compound of the Invention and radiotherapy can act additively or synergistically.

In another embodiment, the invention provides a method for treating cancer, said method comprising administering to a subject in need thereof a pharmaceutical composition comprising an amount of a Compound of the Invention effective to treat cancer.

The combination therapy of the invention can be used accordingly in a variety of settings for the treatment of various cancers.

In a specific embodiment, the subject in need of treatment has previously undergone treatment for cancer. Such previous treatments include, but are not limited to, prior chemotherapy, radiotherapy, surgery, or immunotherapy, such as cancer vaccines.

In another embodiment, the cancer being treated is a cancer which has demonstrated sensitivity to radiotherapy or is known to be responsive to radiotherapy. Such cancers include, but are not limited to, Non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophageal cancer, rectal cancer, small-cell lung cancer, non-small cell lung cancer, brain tumors, or other CNS neoplasms.

In still another embodiment, the cancer being treated is a cancer which has demonstrated resistance to radiotherapy or is known to be refractory to radiotherapy. A cancer may be determined to be refractory to a therapy when at least some significant portion of the cancer cells are not killed or their cell division are not arrested in response to therapy. Such a determination can be made either in vivo or in vitro by any method known in the art for assaying the effectiveness of treatment on cancer cells, using the art-accepted meanings of "refractory" in such a context. In a specific embodiment, a cancer is refractory where the number of cancer cells has not been significantly reduced, or has increased.

Other cancers that can be treated with the Compounds and methods of the Invention include, but are not limited to, cancers and metastases selected from the group consisting of solid tumors, including but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma; blood-borne cancers, including but not limited to: acute lymphoblastic leukemia ("ALL"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia ("CML"), chronic lymphocytic leukemia ("CLL"), hairy cell leukemia, and multiple myeloma; acute and chronic leukemias: lymphoblastic, myelogenous lymphocytic, and myelocytic leukemias; lymphomas: Hodgkin's disease and non-Hodgkin's lymphoma; multiple myeloma; Waldenström's macroglobulinemia; heavy chain disease; and polycythemia vera.

In one embodiment, the cancer is selected from the group consisting of Non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophageal cancer, rectal cancer, small-cell lung cancer, non-small cell lung cancer, brain tumors, and other CNS neoplasms.

The Compounds of the Invention can also be administered to prevent progression to a neoplastic or malignant state, including but not limited to the cancers listed in Table 1. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68-79). Hyperplasia is a form of controlled cell proliferation involving an increase in cell number in a tissue or organ, without significant alteration in structure or function. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a subject, can indicate the desirability of prophylactic/therapeutic administration of the composition of the invention. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

The prophylactic use of the compounds and methods of the present invention are also indicated in some viral infections that may lead to cancer. For example, human papilloma virus can lead to cervical cancer (see, e.g., Hernandez-Avila et al., Archives of Medical Research (1997) 28:265-271), Epstein-Barr virus (EBV) can lead to lymphoma (see, e.g., Herrmann et al., J Pathol (2003) 199(2):140-5), hepatitis B or C virus can lead to liver carcinoma (see, e.g., El-Serag, J Clin Gastroenterol (2002) 35(5 Suppl 2):S72-8), human T cell leukemia virus (HTLV)-I can lead to T-cell leukemia (see e.g., Mortreux et al., Leukemia (2003) 17(1):26-38), human herpesvirus-8 infection can lead to Kaposi's sarcoma (see, e.g., Kadow et al., Curr Opin Investig Drugs (2002) 3(11):1574-9), and Human Immune deficiency Virus (HIV) infection contribute to cancer development as a consequence of immunodeficiency (see, e.g., Dal Maso et al., Lancet Oncol (2003) 4(2):110-9).

In other embodiments, a subject which exhibits one or more of the following predisposing factors for malignancy can treated by administration of the compounds or methods of the invention: a chromosomal translocation associated with a malignancy (e.g., the Philadelphia chromosome for chronic myelogenous leukemia, t(14; 18) for follicular lymphoma, etc.), familial polyposis or Gardner's syndrome (possible forerunners of colon cancer), benign monoclonal gammopathy (a possible forerunner of multiple myeloma), a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W.B. Saunders Co., Philadelphia, pp. 112-113) etc.), and exposure to carcinogens (e.g., smoking, and inhalation of or contacting with certain chemicals).

In another specific embodiment, the compounds and methods of the invention are administered to a human subject to prevent progression to breast, colon, ovarian, or cervical cancer.

The Compounds of the Invention can be administered to a subject that has undergone or is currently undergoing one or more additional anticancer treatment modalities including, but not limited to, chemotherapy, radiotherapy, surgery or immunotherapy, such as cancer vaccines.

In one embodiment, the invention provides methods for treating cancer comprising (a) administering to a subject in need thereof an amount of a combination therapy of the invention; and (b) administering to said subject one or more additional anticancer treatment modalities including, but not limited to, radiotherapy, chemotherapy, surgery or immunotherapy, such as a cancer vaccine. In one embodiment, the administering of step (a) is done prior to the administering of step (b). In another embodiment, the administering of step (a) is done subsequent to the administering of step (b). In still another embodiment, the administering of step (a) is done concurrently with the administering of step (b).

In one embodiment, the additional anticancer treatment modality is chemotherapy.

In another embodiment, the additional anticancer treatment modality is surgery.

In still another embodiment, the additional anticancer treatment modality is immunotherapy, such as cancer vaccines.

In one embodiment, the Compound of the Invention or a pharmaceutically acceptable salt thereof is administered adjunctively with the additional anticancer treatment modality.

In another embodiment, the Compound of the Invention or a pharmaceutically acceptable salt thereof acts synergistically with radiotherapy.

In a preferred embodiment, the additional anticancer treatment modality is radiotherapy. In the methods of the present invention, any radiotherapy protocol can be used depending upon the type of cancer to be treated. For example, but not by way of limitation, X-ray radiation can be administered; in particular, high-energy megavoltage (radiation of greater that 1 MeV energy) can be used for deep tumors, and electron beam and orthovoltage X-ray radiation can be used for skin cancers. Gamma-ray emitting radioisotopes, such as radioactive isotopes of radium, cobalt and other elements, can also be administered. Illustrative radiotherapy protocols useful in the present invention include, but are not limited to, stereotactic methods where multiple sources of low dose radiation are simultaneously focused into a tissue volume from multiple angles; "internal radiotherapy," such as brachytherapy, interstitial irradiation, and intracavitary irradiation, which involves the placement of radioactive implants directly in a tumor or other target tissue; intraoperative irradiation, in which a large dose of external radiation is directed at the target tissue which is exposed during surgery; and particle beam radiotherapy, which involves the use of fast-moving subatomic particles to treat localized cancers.

In a preferred embodiment, the Compound of the Invention or a pharmaceutically acceptable salt thereof is administered prior to the administration of radiotherapy.

In another preferred embodiment, the Compound of the Invention or a pharmaceutically acceptable salt thereof is administered adjunctively with radiotherapy.

The Compound of the Invention and the additional treatment modalities of the combination therapies of the invention can act additively or synergistically (i.e., the combination of an Compound of the Invention or a pharmaceutically acceptable salt thereof, and an additional anticancer treatment modality is more effective than their additive effects when each are administered alone). A synergistic combination permits the use of lower dosages of the Compound of the Invention and/or the additional treatment modality and/or less frequent administration of the Compound of the Invention and/or additional treatment modality to a subject with cancer. The ability to utilize lower dosages of a Compound of the Invention and/or an additional treatment modality and/or to administer a Compound of the Invention and said additional treatment modality less frequently can reduce the toxicity associated with the administration of a Compound of the Invention and/or the additional treatment modality to a subject without reducing the efficacy of a Compound of the Invention and/or the additional treatment modality in the treatment of cancer. In addition, a synergistic effect can result in the improved efficacy of the treatment of cancer and/or the reduction of adverse or unwanted side effects associated with the administration of a Compound of the Invention and/or an additional anticancer treatment modality as monotherapy.

In one embodiment, the Compounds of the Invention may act synergistically with radiotherapy when administered in doses typically employed when such agents are used alone for the treatment of cancer. In another embodiment, the Compounds of the Invention may act synergistically with radiotherapy when administered in doses that are less than doses typically employed when such agents are used as monotherapy for the treatment of cancer.

In one embodiment, radiotherapy may act synergistically with a Compound of the Invention when administered in doses typically employed when radiotherapy is used as monotherapy for the treatment of cancer. In another embodiment, radiotherapy may act synergistically with a Compound of the Invention when administered in doses that are less than doses typically employed when radiotherapy is used as monotherapy for the treatment of cancer.

In a specific embodiment, the Compounds of the Invention act as HDAC inhibitors.

The effectiveness of the use of the Compounds of the Invention as HDAC inhibitors for sensitizing cancer cells to the effect of radiotherapy can be determined by the in vitro and/or in vivo determination of post-treatment survival using techniques known in the art. In one embodiment, for in vitro determinations, exponentially growing cells can be exposed to known doses of radiation and the survival of the cells monitored. Irradiated cells are plated and cultured for about 14- about 21 days, and the colonies are stained. The surviving fraction is the number of colonies divided by the plating efficiency of unirradiated cells. Graphing the surviving fraction on a log scale versus the absorbed dose on a linear scale generates a survival curve. Survival curves generally show an exponential decrease in the fraction of surviving cells at higher radiation doses after an initial shoulder region in which the dose is sublethal. A similar protocol can be used for chemical agents when used in the combination therapies of the invention.

Inherent radiosensitivity of tumor cells and environmental influences, such as hypoxia and host immunity, can be further assessed by in vivo studies. The growth delay assay is commonly used. This assay measures the time interval required for a tumor exposed to radiation to regrow to a specified volume. The dose required to control about 50% of tumors is determined by the TCD50 assay.

In vivo assay systems typically use transplantable solid tumor systems in experimental subjects. Radiation survival parameters for normal tissues as well as for tumors can be assayed using in vivo methods known in the art.

Two mathematical models are commonly employed to analyze radiation survival data. A first model is the multi-target model. In this analysis, the reciprocal of the slope of the survival curve is defined as Do, the radiosensitivity of the cell population or tissue under investigation. Do is the dose required to reduce the surviving fraction to about 37% in the exponential portion of the survival curve. The extrapolation of the linear portion of the curve to the y-intercept is denoted n. The width of the shoulder region is represented by drawing a line from the 100% survival point to the extrapolation line, this width is denoted Dq. Dq is the quasi-threshold dose, or the point at which the reduction in surviving fraction as a function of radiation dosage becomes exponential. The Dq value can also provide an estimate of an additional total dose required for each division of a single dose therapy into fractional doses. The additional dose is required to overcome the effect of sublethal damage repair that occurs when two sublethal doses are separated in time.

When the Compound of the Invention and additional anticancer treatment modality are administered to a subject concurrently, the term "concurrently" is not limited to the administration of a Compound of the Invention and an additional anticancer treatment modality at exactly the same time, but rather it is meant that they are administered to a subject in a sequence and within a time interval such that they can act synergistically to provide an increased benefit than if they were administered otherwise. For example, the Compounds of the Invention may be administered at the same time or sequentially in any order at different points in time as an additional anticancer treatment modality; however, if not administered at the same time, they should be administered sufficiently close in time so as to provide the desired therapeutic effect, preferably in a synergistic fashion. The Compound of the Invention and the additional anticancer treatment modality can be administered separately, in any appropriate form and by any suitable route. When the Compound of the Invention and the additional anticancer treatment modality are not administered concurrently, it is understood that they can be administered in any order to a subject in need thereof. For example, a Compound of the Invention can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional anticancer treatment modality (e.g., radiotherapy), to a subject in need thereof. In various embodiments the Compound of the Invention and the additional anticancer treatment modality are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies of the invention are administered within the same office or hospital visit. In another embodiment, the Compound of the Invention and the additional anticancer treatment modality are administered at 1 minute to 24 hours apart.

In one embodiment, a Compound of the Invention is administered prior or subsequent to an additional anticancer treatment modality, preferably at least an hour, five hours, 12 hours, a day, a week, a month, more preferably several months (e.g., up to three months), prior or subsequent to administration of an additional anticancer treatment modality.

The present invention provides methods of treating cancers comprising the administration of an effective amount of a Compound of the Invention in conjunction with recognized methods of surgery, radiotherapy and chemotherapies, including, for example, chemical-based mimics of radiotherapy whereby a synergistic enhancement of the effectiveness of the recognized therapy is achieved. The effectiveness of a treatment may be measured in clinical studies or in model systems, such as a tumor model in mice, or cell culture sensitivity assays.

The present invention provides combination therapies that result in improved effectiveness and/or reduced toxicity. Accordingly, in one aspect, the invention relates to the use of the Compounds of the Invention as radiosensitizers in conjunction with radiotherapy.

When the combination therapy of the invention comprises administering a Compound of the Invention are with one or more additional anticancer agents, the Compound of the Invention and the additional anticancer agents can be administered concurrently or sequentially to a subject. The agents can also be cyclically administered. Cycling therapy involves the administration of one or more anticancer agents for a period of time, followed by the administration of one or more different anticancer agents for a period of time and repeating this sequential administration, i.e., the cycle, in order to reduce the development of resistance to one or more of the anticancer agents of being administered, to avoid or reduce the side effects of one or more of the anticancer agents being administered, and/or to improve the efficacy of the treatment.

An additional anticancer agent may be administered over a series of sessions; any one or a combination of the additional anticancer agents listed below may be administered.

The present invention includes methods for treating cancer, comprising administering to a subject in need thereof a Compound of the Invention, and one or more additional anticancer agents or pharmaceutically acceptable salts thereof. The Compound of the Invention and the additional anticancer agent(s) can act additively or synergistically. Suitable anticancer agents include, but are not limited to, gemcitabine, capecitabine, methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epirubicin, 5-fluorouracil (5-FU), taxanes such as docetaxel and paclitaxel, leucovorin, levamisole, irinotecan, estramustine, etoposide, nitrogen mustards, BCNU, nitrosoureas such as carmustine and lomustine, vinca alkaloids such as vinblastine, vincristine and vinorelbine, platinum complexes such as cisplatin, carboplatin and oxaliplatin, imatinib mesylate, hexamethylmelamine, topotecan, tyrosine kinase inhibitors, tyrphostins herbimycin A, genistein, erbstatin, and lavendustin A.

In one embodiment, the anti-cancer agent can be, but is not limited to, a drug selected from the group consisting of alkylating agents, nitrogen mustards, cyclophosphamide, ifosfamide, trofosfamide, chlorambucil, nitrosoureas, carmustine (BCNU), lomustine (CCNU), alkylsulphonates, busulfan, treosulfan, triazenes, dacarbazine, platinum complexes, cisplatin, carboplatin, oxaliplatin, plant alkaloids, vinca alkaloids, vincristine, vinblastine, vindesine, vinorelbine), taxoids, paclitaxel, docetaxel, DNA topoisomerase inhibitors, epipodophyllins, etoposide, teniposide, topotecan, 9-aminocamptothecin, camptothecin, crisnatol, mitomycins, mitomycin C, anti-metabolites, anti-folates, DHFR inhibitors, methotrexate, trimetrexate, IMP dehydrogenase inhibitors, mycophenolic acid, tiazofurin, ribavirin, EICAR, ribonucleotide reductase inhibitors, hydroxyurea, deferoxamine, pyrimidine analogs, uracil analogs, 5-fluorouracil, floxuridine, doxifluridine, ratitrexed, cytosine analogs, cytarabine (ara C), cytosine arabinoside, fludarabine, gemcitabine, capecitabine, purine analogs, mercaptopurine, thioguanine, DNA antimetabolites, 3-HP, 2'-deoxy-5-fluorouridine, 5-HP, alpha-TGDR, aphidicolin glycinate, ara-C, 5-aza-2'-deoxycytidine, beta-TGDR, cyclocytidine, guanazole (inosine glycodialdehyde), macebecin II, pyrazoloimidazole, hormonal therapies, receptor antagonists, anti-estrogen, tamoxifen, raloxifene, megestrol, LHRH agonists, goserelin, leuprolide acetate, anti-androgens, flutamide, bicalutamide, retinoids/deltoids, cis-retinoic acid, vitamin A derivative, all-trans retinoic acid (ATRA-IV), vitamin D3 analogs, EB 1089, CB 1093, KH 1060, photodynamic therapies, vertoporfin, BPD-MA, phthalocyanine, photosensitizer Pc4, demethoxy-hypocrellin A (2BA-2-DMHA), cytokines, interferon-α, interferon-β, interferon-γ, tumor necrosis factor, angiogenesis inhibitors, angiostatin (plasminogen fragment), antiangiogenic antithrombin III, angiozyme, ABT-627, Bay 12-9566, benefin, bevacizumab, BMS-275291, cartilage-derived inhibitor (CDI), CAI, CD59 complement fragment, CEP-7055, Col 3, combretastatin A-4, endostatin (collagen XVIII fragment), fibronectin fragment, Gro-beta, halofuginone, heparinases, heparin hexasaccharide fragment, HMV833, human chorionic gonadotropin (hCG), IM-862, interferon inducible protein (IP-10), interleukin-12, kringle 5 (plasminogen fragment), marimastat, metalloproteinase inhibitors (TIMPs), 2-methoxyestradiol, MMI 270 (CGS 27023A), MoAb IMC-1C11, neovastat, NM-3, panzem, PI-88, placental ribonuclease inhibitor, plasminogen activator inhibitor, platelet factor-4 (PF4), prinomastat, prolactin 16 kD fragment, proliferin-related protein (PRP), PTK 787/ZK 222594, retinoids, solimastat, squalamine, SS 3304, SU 5416, SU 6668, SU 11248, tetrahydrocortisol-S, tetrathiomolybdate, thalidomide, thrombospondin-1 (TSP-1), TNP-470, transforming growth factor-beta (TGF-β), vasculostatin, vasostatin (calreticulin fragment), ZD 6126, ZD 6474, farnesyl transferase inhibitors (FTI), bisphosphonates, antimitotic agents, allocolchicine, halichondrin B, colchicine, colchicine derivative, dolstatin 10, maytansine, rhizoxin, thiocolchicine, trityl cysteine, isoprenylation inhibitors, dopaminergic neurotoxins, 1-methyl-4-phenylpyridinium ion, cell cycle inhibitors, staurosporine, actinomycins, actinomycin D, dactinomycin, bleomycins, bleomycin A2, bleomycin B2, peplomycin, anthracycline, daunorubicin, doxorubicin (adriamycin), idarubicin, epirubicin, pirarubicin, zorubicin, mitoxantrone, MDR inhibitors, verapamil, $Ca^{2+}$ ATPase inhibitors, and thapsigargin.

Other anti-cancer agents that may be used in the present invention include, but are not limited to, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide;

floxuridine; fludarabine phosphate; fluorouracil; fluorocitabine; fosquidone; fostriecin sodium; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-Ia; interferon gamma-Ib; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Further anti-cancer drugs that can be used in the present invention include, but are not limited to: 20-epi-1,25-dihydroxyvitamin D3; 5-ethynyluracil; abiraterone; aclarubicin; acylfulvene; adecypenol; adozelesin; aldesleukin; ALL TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein 1; antiandrogen, prostatic carcinoma; antiestrogen; antineoplaston; antisense oligonucleotides; aphidicolin glycinate; apoptosis gene modulators; apoptosis regulators; apurinic acid; ara CDP DL PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; carboxamide amino triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro 5 azacytidine; dihydrotaxol, 9; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin like growth factor 1 receptor inhibitor; interferon agonists; interferons; interleukins; iobenguane; iododoxorubicin; ipomeanol, 4; iroplact; irsogladine; isobengazole; isohomohalicondrin B; itasetron; jasplakinolide; kahalalide F; lamellarin N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum complexes; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1 based therapy; mustard anti-cancer agent; mycaperoxide B; mycobacterial cell wall extract; myriaporone; N acetyldinaline; N substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6 benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum complexes; platinum triamine complex; porfimer sodium; porfiromycin; prednisone; propyl bis acridone; prostaglandin J2; proteasome inhibitors; protein A based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

It is a further aspect of the invention the Compounds of the Invention can be administered in conjunction with chemical agents that are understood to mimic the effects of radiotherapy and/or that function by direct contact with DNA. Preferred agents for use in combination with the Compounds of the Invention for treating cancer include, but are not limited to cis-diamminedichloro platinum (II) (cisplatin), doxorubicin, 5-fluorouracil, taxol, and topoisomerase inhibitors such as etoposide, teniposide, irinotecan and topotecan.

Additionally, the invention provides methods of treatment of cancer using the Compounds of the Invention as an alternative to chemotherapy alone or radiotherapy alone where the chemotherapy or the radiotherapy has proven or can prove too toxic, e.g., results in unacceptable or unbearable side effects, for the subject being treated. The subject being treated can, optionally, be treated with another anticancer treatment modality such as chemotherapy, surgery, or immunotherapy, depending on which treatment is found to be acceptable or bearable.

The Compounds of the Invention can also be used in an in vitro or ex vivo fashion, such as for the treatment of certain cancers, including, but not limited to leukemias and lymphomas, such treatment involving autologous stem cell transplants. This can involve a multi-step process in which the subject's autologous hematopoietic stem cells are harvested and purged of all cancer cells, the subject is then administered an amount of a Compound of the Invention effective to eradicate the subject's remaining bone-marrow cell population, then the stem cell graft is infused back into the subject. Supportive care is then provided while bone marrow function is restored and the subject recovers.

The present methods for treating cancer can further comprise the administration of a Compound of the Invention and an additional therapeutic agent or pharmaceutically acceptable salts, solvates or hydrates thereof. In one embodiment, a composition comprising a Compound of the Invention is administered concurrently with the administration of one or more additional therapeutic agent(s), which may be part of the same composition or in a different composition from that comprising the Compound of the Invention. In another embodiment, a Compound of the Invention is administered prior to or subsequent to administration of another therapeutic agent(s).

In the present methods for treating cancer the other therapeutic agent may be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron.

In a preferred embodiment, the anti-emetic agent is granisetron or ondansetron.

In another embodiment, the other therapeutic agent may be an hematopoietic colony stimulating factor. Suitable hematopoietic colony stimulating factors include, but are not limited to, filgrastim, sargramostim, molgramostim and epoietin alfa.

In still another embodiment, the other therapeutic agent may be an opioid or non-opioid analgesic agent. Suitable opioid analgesic agents include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofenac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

In still another embodiment, the other therapeutic agent may be an anxiolytic agent. Suitable anxiolytic agents include, but are not limited to, buspirone, and benzodiazepines such as diazepam, lorazepam, oxazapam, chlorazepate, clonazepam, chlordiazepoxide and alprazolam.

Treatment of Neurological Diseases

The Compounds of the Invention are useful for treating neurological disease. Neurological diseases can be treated or prevented by administration of amounts of the Compounds of the invention that are effective to treat the neurological disease or by administration of a pharmaceutical composition comprising amounts of the Compounds of the invention that are effective to treat the neurological disease. In one embodiment, the neurological diseases that can be treated or prevented by administering a Compound of the Invention include, but are not limited to, Huntington's disease, lupus, schizophrenia, multiple sclerosis, muscular dystrophy, drug-induced movement disorders, Creutzfeldt-Jakob disease, amyotrophic lateral sclerosis, Pick's disease, Alzheimer's disease, Lewy body dementia, cortico basal degeneration, dystonia, myoclonus, Tourette's Syndrome, tremor, chorea, restless leg syndrome, Parkinson's disease, and Parkinsonian Syndromes, such as progressive supranuclear palsy, multiple system atrophy, Wilson's disease and mult-infarct state. In a preferred embodiment, the neurological disease treated is Huntington's disease, lupus, or schizophrenia.

Treatment of Malaria

Compounds of the invention can be used to treat parasitic infections (e.g., malaria, trypanosomiasis, helminthiasis, protozoal infections (see Andrews et al. *Int. J. Parasitol.* 2000, 30(6), 761-768). In certain embodiments, the compounds of the invention can be used to treat malaria.

Definitions

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 80 or fewer carbon atoms in its backbone (e.g., $C_1$-$C_{80}$ for straight chain, $C_3$-$C_{80}$ for branched chain), and alternatively, about 30 or fewer. Likewise, cycloalkyls have from about 3 to about 10 carbon atoms in their ring structure, and alternatively about 5, 6 or 7 carbons in the ring structure. As used herein, "fluoroalkyl" denotes an alkyl where one or more hydrogens have been replaced with fluorines; "perfluoroalkyl" denotes an alkyl where all the hydrogens have been replaced with fluorines.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "alkylene," is art-recognized, and as used herein, pertains to a bidentate moiety obtained by removing two hydrogen atoms, either both from the same carbon atom, or one from each of two different carbon atoms, of a hydrocarbon compound, which may be aliphatic or alicyclic, or a combination thereof, and which may be saturated, partially unsaturated, or fully unsaturated. Examples of linear saturated $C_{1-10}$alkylene groups include, but are not limited to, —$(CH_2)_n$— where n is an integer from 1 to 10, for example, —$CH_2$— (methylene), —$CH_2CH_2$— (ethylene), —$CH_2CH_2CH_2$— (propylene), —$CH_2CH_2CH_2CH_2$— (butylene), —$CH_2CH_2CH_2CH_2CH_2$— (pentylene) and —$CH_2CH_2CH_2CH_2CH_2CH_2$— (hexylene). Examples of branched saturated $C_{1-10}$alkylene groups include, but are not limited to, —$CH(CH_3)$—, —$CH(CH_3)CH_2$—, —$CH(CH_3)CH_2CH_2$—, —$CH(CH_3)CH_2CH_2CH_2$—, —$CH_2CH(CH_3)CH_2$—, —$CH_2CH(CH_3)CH_2CH_2$—, —$CH(CH_2CH_3)$—, —$CH(CH_2CH_3)CH_2$—, and —$CH_2CH(CH_2CH_3)CH_2$—. Examples of linear partially unsaturated $C_{1-10}$alkylene groups include, but are not limited to, —CH═CH— (vinylene), —CH═CH—$CH_2$—, —CH═CH—$CH_2$—$CH_2$—, —CH═CH—$CH_2$—$CH_2$-$CH_2$—, —CH═CH—CH═CH—, —CH═CH—CH═CH—$CH_2$—, —CH═CH—CH═CH—$CH_2$—$CH_2$—, —CH═CH—$CH_2$—CH═CH—, and —CH═CH—$CH_2$—$CH_2$—CH═CH—. Examples of branched partially unsaturated $C_{1-10}$alkylene groups include, but are not limited to, —C(CH$_3$)=CH—, —C(CH$_3$)=CH—CH$_2$—, and —CH=CH—CH(CH$_3$)—. Examples of alicyclic saturated $C_{1-10}$alkylene groups include, but are not limited to, cyclopentylene (e.g., cyclopent-1,3-ylene), and cyclohexylene (e.g., cyclohex-1,4-ylene). Examples of alicyclic partially unsaturated $C_{1-10}$alkylene groups include, but are not limited to, cyclopentenylene (e.g., 4-cyclopenten-1,3-ylene), and cyclohexenylene (e.g., 2-cyclohexen-1,4-ylene, 3-cyclohexen-1,2-ylene, and 2,5-cyclohexadien-1,4-ylene).

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, alkylthio, sulfonyl, sulfonamido, ketone, aldehyde, ester, heterocyclyl, aromatic or heteroaromatic moieties, trifluoromethyl, cyano, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, alkylthio, sulfonyl, ketone, aldehyde, ester, a heterocyclyl, an aromatic or heteroaromatic moiety, trifluoromethyl, cyano, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, alkylthio, sulfonyl, ketone, aldehyde, ester, a heterocyclyl, an aromatic or heteroaromatic moiety, trifluoromethyl, cyano, or the like.

The term "carbocycle" is art-recognized and refers to an aromatic or non-aromatic ring in which each atom of the ring is carbon.

The terms "monocyclic," "bicyclic," or "tricyclic" ring systems refers to 5 or 6 member monocyclic rings, 8, 9 and 10 membered bicyclic ring structures, and 11, 12, 13 and 14 membered tricyclic ring structures, wherein each bond in each ring may be possess any degree of saturation that is chemically feasible. When such structures contain substituents, those substituents may be at any position of the ring system, unless otherwise specified. As specified, such ring systems may optionally comprise up to 4 heteroatoms selected from N, O or S. Those heteroatoms may replace any carbon atoms in these ring systems as long as the resulting compound is chemically stable.

The term "monocyclic" ring system, as used herein, includes saturated, partially unsaturated and fully unsaturated ring structures. The term "bicyclic" ring system, as used herein, includes systems wherein each ring is independently saturated, partially unsaturated and fully unsaturated. Examples of monocyclic and bicyclic ring systems useful in the compounds of this invention include, but are not limited to, cyclopentane, cyclopentene, indane, indene, cyclohexane, cyclohexene, cyclohexadiene, benzene, tetrahydronaphthalene, decahydronaphthalene, naphthalene, pyridine, piperidine, pyridazine, pyrimidine, pyrazine, 1,2,3-triazine, 1,2,4-triazine, 1,3,5-triazine, 1,2,3,4-tetrazine, 1,2,4,5-tetrazine, 1,2,3,4-tetrahydroquinoline, quinoline, 1,2,3,4-tetrahydroisoquinoline, isoquinoline, cinnoline, phthalazine, quinazoline, quinoxaline, 1,5-naphthyridine, 1,6-naphthyridine, 1,7-naphthyridine, 1,8-naphthyridine, 2,6-naphthyridine, 2,7-naphthyridine, pteridine, acridine, phenazine, 1,10-phenatroline, dibenzopyrans; 1-benzopyrans, phenothiazine, phenoxazine, thianthrene, dibenzo-p-dioxin, phenoxathiin, phenoxthionine, morpholine, thiomorpholine, tetrahydropyan, pyran, benzopyran, 1,4-dioxane, 1,3-dioxane, dihyropyridine, dihydropyran, 1-pyrindine, quinuclidine, triazolopyridine, β-carboline, indolizine, quinolizidine, tetrahydronaphtheridine, diazaphenanthrenes, thiopyran, tetrahydrothiopyran, benzodioxane, furan, benzofuran, tetrahydrofuran, pyrrole, indole, thiophene, benzothiopene, carbazole, pyrrolidine, pyrazole, isoxazole, isothiazole, imidazole, oxazole, thiazole, 1,2,3-triazole, 1,2,4-triazole, 1,2,3-oxadiazole, 1,2,4-oxadiazole, 1,3,4 oxadiazole, 1,2,5-oxadiazole, 1,2,3-thiadiazole, 1,2,4-thiadiazole, 1,3,4-thiadiazole, 1,2,5 thiadiazole, tetrazole, benzothiazole, benzoxazole, benzotriazole, benzimidazole, benzopyrazole, benzisothiazole, benzisoxazole and purine.

Additional monocyclic and bicyclic structures falling within the above description may be found in A. R. Katritzky, and C. W. Rees, eds. "Comprehensive Heterocyclic Chemistry: Structure, Reactions, Synthesis and Use of Heterocyclic Compounds, Vol. 1-8," Pergamon Press, NY (1984), the disclosure of which is herein incorporated by reference.

It should be understood that heterocycles may be attached to the rest of the compound by any atom of the heterocycle which results in the creation of a stable structure.

The term "ring atom", as used herein, refers to a backbone atom that makes up the ring. Such ring atoms are selected from C, N, O or S and are bound to 2 or 3 other such ring atoms (3 in the case of certain ring atoms in a bicycle ring system). The term "ring atom" does not include hydrogen.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —$SO_2^-$. "Halide" designates the corresponding anion of the halogens, and "pseudohalide" has the definition set forth on page 560 of "Advanced Inorganic Chemistry" by Cotton and Wilkinson, that is, for example, monovalent anionic groups sufficiently electronegative to exhibit a positive Hammett sigma value at least equaling that of a halide (e.g., CN, OCN, SCN, SeCN, TeCN, $N_3$, and $C(CN)_3$).

The terms "amine" and "amino" are art-recognized and refer to both unsubstituted and substituted amines, e.g., a moiety that may be represented by the general formulas:

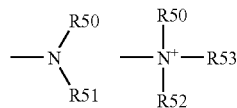

wherein R50, R51, R52 and R53 each independently represent a hydrogen, an alkyl, an alkenyl, —$(CH_2)_m$—R61, or R50 and R51 or R52, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

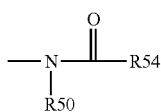

wherein R50 is as defined above, and R54 represents a hydrogen, an alkyl, an alkenyl or —$(CH_2)_m$—R61, where m and R61 are as defined above.

The term "amido" is art recognized as an amino-substituted carbonyl and includes a moiety that may be represented by the general formula:

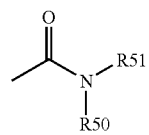

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethyl thio, and the like.

The term "carboxyl" is art recognized and includes such moieties as may be represented by the general formulas:

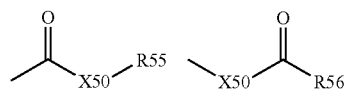

wherein X50 is a bond or represents an oxygen or a sulfur, and R55 and R56 represents a hydrogen, an alkyl, an alkenyl, —$(CH_2)_m$—R61 or a pharmaceutically acceptable salt, R56 represents a hydrogen, an alkyl, an alkenyl or —$(CH_2)_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularyl when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

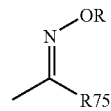

wherein R75 is hydrogen, alkyl, cycloalkyl, alkenyl, alkynyl, aryl, aralkyl, or —$(CH_2)_m$—R61. The moiety is an "oxime" when R is H; and it is an "oxime ether" when R is alkyl, cycloalkyl, alkenyl, alkynyl, aryl, aralkyl, or —$(CH_2)_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—$(CH_2)_m$—R61, where m and R61 are described above.

The term "sulfonate" is art recognized and refers to a moiety that may be represented by the general formula:

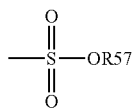

in which R57 is an electron pair, hydrogen, alkyl, cycloalkyl, or aryl.

The term "sulfate" is art recognized and includes a moiety that may be represented by the general formula:

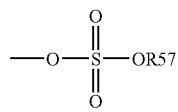

in which R57 is as defined above.

The term "sulfonamido" is art recognized and includes a moiety that may be represented by the general formula:

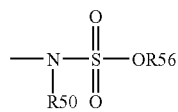

in which R50 and R56 are as defined above.

The term "sulfamoyl" is art-recognized and refers to a moiety that may be represented by the general formula:

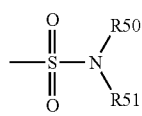

in which R50 and R51 are as defined above.

The term "sulfonyl" is art-recognized and refers to a moiety that may be represented by the general formula:

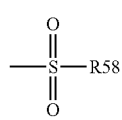

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

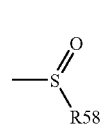

in which R58 is defined above.

The term "phosphoryl" is art-recognized and may in general be represented by the formula:

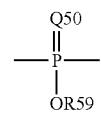

wherein Q50 represents S or O, and R59 represents hydrogen, a lower alkyl or an aryl. When used to substitute, e.g., an alkyl, the phosphoryl group of the phosphorylalkyl may be represented by the general formulas:

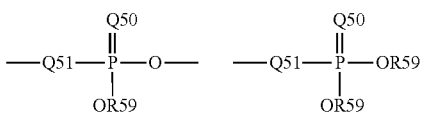

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

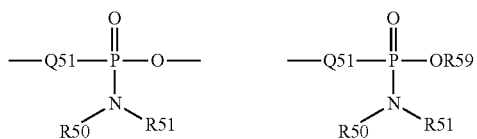

wherein Q51, R50, R51 and R59 are as defined above.

The term "phosphonamidite" is art-recognized and may be represented in the general formulas:

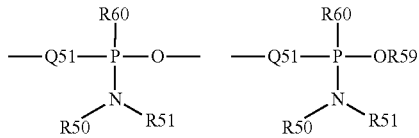

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The definition of each expression, e.g., alkyl, m, n, and the like, when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, "Handbook of Chemistry and Physics", 67th Ed., 1986-87, inside cover.

While several embodiments of the present invention are described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

EXEMPLIFICATION

The invention now being generally described, it will be more readily understood by reference to the following examples, which are included merely for purposes of illustration of certain aspects and embodiments of the present invention, and are not intended to limit the invention.

$^1$H NMR and $^{13}$C NMR spectra were recorded on Bruker spectrometer at 360/400 MHz and 75 MHz respectively with TMS as an internal standard. Standard abbreviation indicating multiplicity was used as follows: s=singlet, d=doublet, t=triplet, q=quadruplet, quin=quintuplet, m=multiplet and br=broad. HRMS experiment was performed on Q-TOF-2TM (Micromass). TLC was performed with Merck 250-mm 60F$_{254}$ silica gel plates. Preparative TLC was performed with Analtech 1000-mm silica gel GF plates. Column chromatography was performed using Merck silica gel (40-60 mesh). Analytical and preparative HPLC was carried out on an ACE AQ columns, with detection at 254 and 280 nm on a Shimadzu SPD-10A VP detector; from 10% acetonitrile in water to 100% acetonitrile with 0.05% TFA.

Example One

General Procedure for Biphenyl Octanedioic Acid Hydroxyamides (7a-7f)

The following method represents a typical procedure for synthesis of the octanedioic acid hydroxyamide-based ligands.

Preparation of octanedioic acid {2'-[2-amino-3-(1H-indol-3-yl)-propionylamino]-biphenyl-4-yl}-amide hydroxyamide (7d). To a stirring solution of Boc-L-Trp-OH (1.67 g, 5.4 mmol) and 4'-nitro-biphenyl-2-ylamine (1.18 g, 5.4 mmol) in dry pyridine (20 ml), POCl$_3$ (0.84 g, 5.4 mmol) was added dropwise at −15° C. After stirring for 1 hour at the same temperature, reaction mixture was concentrated in vacuo. The residue was dissolved in EtOAc and washed thoroughly with saturated NH$_4$Cl solution and brine, separated organic phase was dried over Na$_2$SO$_4$ and concentrated in vacuo. The crude material was purified by flash chromatography (acetone/hexane, 1:1) to give compound 3d (1.600 g, 58.2%). $^1$H NMR (CDCl$_3$, 400 Hz); δ=1.36 (s, 9H), 3.17 (dd, J=7.6 and 14.4 Hz, 1H), 3.39 (dd, J=4.0 and 14.4 Hz, 1H,), 4.39-4.46 (m, 1H), 4.95-5.12 (m, 1H), 6.99 (d, J=8.7 Hz, 1H), 7.00 (s, 1H) 7.18-7.10 (m, 2H), 7.20-7.27 (m, 2H), 7.36-7.45 (m, 2H), 7.53 (s, 1H), 7.61 (d, J=7.9 Hz, 1H), 7.90 (d, J=8.4 Hz, 2H), 8.22-8.27 (m, 2H). NMR (CDCl$_3$, 75 MHz): S=28.5, 56.5, 60.8, 110.4, 111.7, 119.2, 120.5, 122.3, 123.1, 123.8, 124.3, 125.3, 127.5, 130.0, 130.1, 130.2, 130.8, 134.3, 136.6, 144.9, 147.5, 170.4.

Method A: A suspension of compound 3d (1.80 g, 3.5 mmol) and Pd(OH)$_2$/C (20 wt. %, 0.5 g) in a mixture of methanol (10 ml) and CH$_2$Cl$_2$ (10 ml) was stirred under hydrogen atmosphere for 4 hours at room temperature. The catalyst was removed by filtration through a pad of celite and the solvent was evaporated to give a residue which was purified by flash chromatography (ethyl acetate/hexane 1:1 then 2:1) to give compound 4d (1.40 g, 83%). $^1$H NMR (CDCl$_3$, 300 Hz): δ=1.38 (s, 9H), 3.12-3.28 (m, 1H), 3.30-3.45 (m, 1H), 4.46 (br s, 1H), 5.08 (br s, 1H), 6.35 (br s, 2H), 6.61 (br s, 2H), 6.95 (s, 1H), 7.08-7.19 (m, 4H), 7.22 (t, J=7.2 Hz, 1H), 7.27-7.40 (m, 3H), 7.62 (d, J=7.3 Hz, 1H), 7.77 (br s, 1H), 8.35 (br s, 2H). $^{13}$C NMR (CD$_3$OD, 75 MHz): δ=28.6, 56.7, 80.4, 111.7, 115.9, 119.2, 120.1, 121.0, 122.5, 123.8, 124.7, 125.0, 128.1, 130.2, 130.2, 132.6, 134.7, 136.6, 145.8, 155.6, 170.1. To a stirring solution of 7-benzyloxycarbamoyl-heptanoic acid (5) (0.130 g, 0.46 mmol) in dry DMF (5 ml) DIPEA (0.120 g, 0.92 mmol) was added, and the mixture was stirred for 10 minutes at room temperature. Then PyBOP (0.480 g, 0.92 mmol) and biphenyl amine 4d (0.220 g, 0.46 mmol) were added subsequently and stirring was continued over night. The reaction mixture was diluted with diethyl ether washed with water, saturated NaHCO$_3$ solution, saturated NH$_4$Cl solution and brine, dried over Na$_2$SO$_4$. The solvent was removed by rotary evaporation and crude material was purified by flash chromatography (acetone/hexane, 1:1) to give compound 6d (0.233 g, 70%). $^1$H NMR (CDCl$_3$, 300 Hz): δ=1.30-1.50 (m, 13H), 1.60-1.85 (m, 4H), 2.06 (br s, 2H), 2.37 (t, J=7.1 Hz, 2H), 2.94-3.20 (m, 1H), 3.25-3.48 (m, 1H), 4.37 (br s, 1H), 4.92 (s, 2H), 5.21 (br s, 1H), 6.73 (br s, 2H), 6.84 (br s, 1H), 7.18-7.00 (m, 4H), 7.26-7.45 (m, 9H), 7.45-7.60 (m, 2H), 7.68 (br s, 1H), 8.30 (br s, 1H), 8.51 (br s, 1H), 8.83 (br s, 1H). To a solution of compound 6d (0.046 mg, 0.063 mmol) in CH$_2$Cl$_2$ (5 ml) TFA (2 ml) was added. After 2 hours the reaction mixture was diluted with diethyl ether, washed with saturated aqueous NaHCO$_3$ and brine, dried over Na$_2$SO$_4$ and concentrated in vacuo. The crude material was purified by flash chromatography (methanol/CH$_2$Cl$_2$, 10:1) to give benzyl-O— protected compound 7d (0.020 g, 51%). $^1$H NMR (CDCl$_3$, 300 Hz): δ=1.32-1.78 (m, 81-1), 2.04 (br s, 2H), 2.33 (br t, 2H), 3.00 (dd, J=7.9 and 14.3 Hz, 1H), 3.31 (dd, J=4.4 and 14.5 Hz, 1H), 3.71 (dd, J=4.2 and 7.5 Hz, 1H), 4.90 (br s, 2H), 6.84 (s, 1H), 7.04-7.22 (m, 6H), 7.32-7.42 (m, 7H), 7.48 (d, J=7.9 Hz, 2H), 7.61 (d, J=7.8 Hz, 1H), 7.80 (br s, 1H), 8.35 (d, J=8.1 Hz, 1H), 8.48-8.62 (br d, 1H), 9.49 (s, 1H). $^{13}$C NMR (CDCl$_3$, 75 MHz) δ=24.5, 24.7, 25.9, 26.0, 28.0, 29.3, 29.8, 29.9, 31.4, 32.4, 36.8, 46.6, 50.4, 55.3, 65.4, 77.7, 110.3, 111.0, 118.4, 119.0, 119.6, 120.5, 121.0, 121.6, 123.0, 123.9, 124.1, 127.0, 127.8, 128.2, 128.3, 128.8, 129.4, 129.6, 132.0, 133.5, 134.3, 134.8, 136.0, 137.1, 170.6, 171.5, 172.8.

A suspension of benzyl-O— protected compound 7d (0.031 g, 0.049 mmol) and Pd(OH)$_2$/C (20 wt. %, 0.010 g) in methanol (5 ml) was stirred under hydrogen atmosphere at room temperature for 4 hours. The catalyst was removed by filtration through a pad of celite and the residue was thoroughly washed with MeOH. The solvent was evaporated in vacuo, and the residue was crystallized from methanol/ether, 5:95 to give hydroxamate 7d (0.008 g, 30%). $^1$H NMR (CD$_3$OD, 300 MHz): S=1.30-1.78 (m, 8H), 2.10 (d, J=7.0 Hz, 2H), 2.37 (d, J=7.0 Hz, 2H), 3.02-3.15 (m, 1H), 3.25-3.35 (m, 1H), 3.96-4.05 (m, 1H), 6.96-7.08 (m, 1H), 7.09-7.22 (m, 4H), 7.23-7.48 (m, 5H), 7.52-7.67 (m, 3H), 7.74 (d, J=7.7 Hz, 1H). $^{13}$C NMR (DMSO-d$_6$, 75 MHz) δ=24.8, 24.9, 26.9, 28.0, 28.1, 31.9, 36.0, 53.5, 99.5, 106.1, 110.9, 114.7, 117.4, 118.6, 119.8, 121.2, 123.8, 125.2, 126.1, 126.4, 127.2, 128.7, 129.8, 132.7, 133.8, 136.0, 136.4, 137.5, 167.5, 171.3, 173.1. FAB-HRMS calculated for [C$_{31}$H$_{35}$N$_5$O$_4$+H]$^+$: 542.2761; found: 542.2762. HPLC purity: 95%.

Spectral data for octanedioic acid [2'-(2-amino-acetylamino)-biphenyl-4-yl]-amide hydroxyamide (7a). $^1$H NMR (DMSO-d$_6$, 400 MHz): S=1.37 (m, 4H), 1.48 (m, 2H), 1.57 (m, 2H), 1.93 (t, J=7.2 Hz, 2H), 2.30 (t, J=7.2 Hz, 2H), 3.43 (m, 2H), 3.62 (br s, 2H), 4.34 (t, J=4.9 Hz, 1H), 7.32 (m, 5H), 7.50 (d, J=7.5 Hz, 1H), 7.67 (d, J=8.5 Hz, 2H), 8.65 (s, 1H), 9.99 (s, 1H), 10.34 (s, 1H). $^{13}$C NMR (DMSO-d$_6$, 75 MHz): δ=25.4, 25.5, 28.8, 30.8, 32.6, 34.8, 36.8, 119.4, 125.3, 126.8, 128.0, 128.4, 129.5, 130.8, 133.2, 133.9, 136.2, 139.1, 139.6, 166.0, 169.5, 171.8. FAB-HRMS calculated for [C$_{22}$H$_{28}$N$_4$O$_4$+H]$^+$: 413.2189; found: 413.2182. HPLC purity: 96%.

Spectral data for octanedioic acid [2'-(2-amino-3-phenyl-propionylamino)-biphenyl-4-yl]-amide hydroxyamide (7b). $^1$H NMR (DMSO-d$_6$, 400 MHz): δ=1.23 (m, 4H), 1.49 (m, 2H), 1.59 (m, 2H), 1.94 (t, J=7.0 Hz, 2H), 2.31 (t, J=7.0 Hz, 2H), 2.75 (dd, J=8 and 13 Hz, 1H), 3.01 (dd, J=4.0 and 13.0 Hz, 1H), 3.34 (m, 2H), 3.52 (m, 1H), 7.14-7.35 (m, 10H), 7.64 (d, J=8.4 Hz, 2H), 8.22 (d, J=8.1 Hz, 1H), 8.66 (br s, 1H), 9.96 (s, 1H), 10.34 (s, 1H). $^{13}$C NMR (DMSO-d$_6$, 75 MHz): δ=25.4, 28.8, 32.7, 36.8, 55.9, 119.5, 121.5, 124.5, 126.7, 128.1, 129.7, 129.8, 130.6, 132.5, 132.6, 135.2, 138.6, 139.2, 169.5, 171.7, 173.1. FAB-HRMS calculated for [C$_{29}$H$_{34}$N$_4$O$_4$+H]$^+$: 503.2658; found: 503.2648. HPLC purity: 95%.

Spectral data for octanedioic acid hydroxyamide {2'-[(pyrrolidine-2-carbonyl)-amino]-biphenyl-4-yl}-amide (7c). $^1$H NMR (DMSO-d$_6$, 400 MHz): δ=1.09 (m, 4H), 1.48-1.58 (m, 4H), 1.82-1.94 (m, 5H), 2.19 (m, 1H), 2.30 (m, 3H), 3.15 (m, 2H), 4.17 (m, 1H), 7.17-1.66 (m, 8H), 8.66 (br s, 1H), 9.95 (br s, 1H), 10.00 (bs, 1H), 10.35 (br s, 1H). $^{13}$C NMR (DMSO-d$_6$, 75 MHz): δ=23.9, 25.4, 28.8, 29.6, 32.6, 36.8, 46.1, 59.9, 119.3, 125.7, 128.1, 128.6, 129.3, 129.5, 130.7, 133.3, 133.9, 139.2, 169.5, 171.7. FAB-HRMS calculated for [C$_{25}$H$_{32}$N$_4$O$_4$+H]$^+$: 453.2502; found: 453.2494. HPLC purity: 98%.

Preparation of octanedioic acid {2'-[2-amino-3-(4-hydroxy-phenyl)-propionylamino]-biphenyl-4-yl}-amide hydroxyamide (7e). Method B: A mixture of nitro compound 3e (2.11 g, 3.7 mmol) and SnCl$_2$ (7.05 g, 37.1 mmol) in methanol/dioxane (30 ml, 7/3) was refluxed overnight. The solvent was evaporated; the residue was diluted with saturated NaHCO$_3$ and EtOAc and stirred vigorously for 30 minutes. The mixture was filtered and the residue solid was thoroughly washed with EtOAc. The organic layer was separated and the aqueous layer was extracted with EtOAc for two times. The combined organic phase was dried over Na$_2$SO$_4$ and evaporated in vacuo. The crude material was purified by flash chromatography (ethyl acetate/hexane 1:2) to give compound 4e (1.20 g, 60%). $^1$H NMR. (CDCl$_3$, 300 MHz,) δ=1.38 (s, 9H), 2.93-3.10 (m, 2H), 3.75 (br s, 2H), 4.29 (br s, 1H), 4.93-5.00 (m, 1H), 5.04 (s, 2H), 6.64 (d, J=7.9 Hz, 1H), 6.80-6.95 (m, 4H), 7.05-7.20 (m, 4H), 7.30-7.46 (m, 6H), 7.70 (br s, 1H), 8.39 (d, J=8.1 Hz, 1H). $^{13}$C NMR (CD$_3$OD, 75 MHz) δ=28.6, 38.1, 70.4, 115.5, 115.7, 120.8, 124.6, 127.6, 127.8, 128.1, 128.3, 129.0, 130.4, 130.8, 132.5, 134.7, 137.3, 146.5, 158.3, 169.5.

Spectral data (7e). $^1$H NMR (CD$_3$OD, 300 MHz) δ=1.30-1.75 (m, 8H), 2.11 (t, J=7.1 Hz, 2H), 2.39 (t, J=7.1 Hz, 2H), 2.70-2.82 (m, 1H), 2.90-3.00 (m, 1H), 3.65 (t, J=5.8 Hz, 1H), 6.74 (d, J=8.2 Hz, 2H), 7.02 (d, J=7.2 Hz, 2H), 7.10-7.40 (m, 6H), 7.61 (d, J=8.2 Hz, 2H), 7.90 (d, J=7.8 Hz, 1H). $^{13}$C NMR (CD$_3$OD, 75 MHz) δ=15.7, 25.7, 25.9, 28.8, 28.9, 32.7, 36.8, 39.2, 56.6, 115.5, 120.3, 123.9, 127.5, 127.9, 129.6, 130.4, 130.5, 134.3, 134.3, 135.1, 138.4, 156.5, 171.9, 173.2, 173.7. FAB-HRMS calculated for [C$_{29}$H$_{34}$N$_4$O$_5$+H]$^+$: 519.2602; found: 519.2595. HPLC purity: 95%.

Preparation of (4'-nitro-biphenyl-2-yl)-Carbamic acid tert-butyl ester (31). Method C: A mixture of 4'-nitro-biphenyl-2-ylamine (1) (0.857 g, 4.0 mmol) and di-tert-butyl dicarbonate (0.870 g, 4.0 mmol) in toluene was heated to 100° C. overnight, and then additional amount of di-tert-butyl dicarbonate (0.175 g, 0.8 mmol) was added. The mixture was kept at 100° C. for another 4 hours and the solvent was then evaporated in vacuo. The solid residue was washed with hexanes/EtOAc 4:1, filtered, and dried to yield (4'-Nitro-biphenyl-2-yl)-Carbamic acid tert-butyl ester (31) (1.0 g, 79%).

Example 2

General Procedure for Biphenyl 6-Mercapto-Acetylamino-Hexanoic Acid Amides (10a-e)

The following method represents a typical procedure for synthesis of the 6-mercapto-acetylamino-hexanoic acid amide-based ligands.

Preparation of 6-(2-mercapto-acetylamino)-hexanoic acid {2'-[2-amino-3-(1H-indol-3-yl)-propionylamino]-biphenyl-4-yl}-amide (10d). To a stirring solution of 6-(2-tritylsulfanyl-acetylamino)-hexanoic acid (8) (0.218 g, 0.48 mmol) in dry DMF (3 ml) DIPEA (0.126 g, 0.97 mmol) was added, and the mixture was stirred for 10 minutes at room temperature. Then PyBOP (0.508 g, 0.97 mmol) and biphenyl amine 4d (0.230 g, 0.48 mmol) were added and stirring was continued over night. The reaction mixture was diluted with diethyl ether, washed consecutively with cold water, saturated NaHCO$_3$ solution, saturated NH$_4$Cl solution and brine, dried over Na$_2$SO$_4$. The solvent was removed by rotary evaporation and crude material was purified by flash chromatography (acetone/hexane, 1:1) to give compound 9d (0.224 g, 51%). $^1$H NMR (CD$_3$OD, 300 MHz) δ=1.30-1.50 (m, 13H), 1.69 (t, J=6.7 Hz, 2H), 2.28-2.40 (m, 2H), 2.90-3.02 (m, 2H), 3.05-3.20 (m, 3H), 3.24-3.45 (m, 1H), 4.38 (br s, 1H), 5.21 (br s, 1H), 6.11 (t, J=5.4 Hz, 1H), 6.68-6.82 (m, 3H), 6.94-7.18 (m, 4H), 7.20-7.48 (m, 22H), 7.53 (d, J=7.7 Hz, 1H), 7.69 (br s, 1H), 8.15 (s, 1H), 8.27 (d, J=6.9 Hz, 1H), 9.08 (s, 1H). $^{13}$C NMR (CDCl$_3$, 75 MHz)=14.6, 19.3, 21.4, 25.4, 26.7, 28.6, 29.3, 36.4, 37.5, 39.9, 60.8, 68.2, 80.4, 109.9, 111.9, 119.0, 119.8, 121.6, 121.6, 122.3, 123.7, 124.9, 127.5, 127.7, 128.5, 129.8, 130.3, 132.6, 133.6, 134.6, 136.7, 138.0, 144.3, 155.6, 168.6, 170.6, 171.6, 172.2.

To a solution of compound 9d (0.070 g, 0.077 mmol) in CH$_2$Cl$_2$ TFA (1 ml) was added. The resulting yellow solution was treated dropwise with triethylsilane until the color disappeared. The mixture was then stirred for 2 hours and the solvent was evaporated in vacuo. The residue was dissolved in EtOAc and consecutively washed with saturated NaHCO$_3$ solution and brine, organic phase was dried over Na$_2$SO$_4$ and evaporated. The crude material was purified by flash chromatography (methanol/CH$_2$Cl$_2$, 1:10) to give compound 10d (0.026 mg, 60%). $^1$H NMR (CD$_3$OD, 400 Hz): δ=1.50-1.48 (m, 2H), 1.53-. 1.65 (m, 2H), 1.68-1.78 (m, 2H), 2.40 (t, J=7.4 Hz, 2H), 3.03 (dd, J=7.1 and 14.3 Hz, 1H), 3.13 (s, 2H), 3.15-3.28 (m, 3H), 3.69 (dd, J=6.9 and 12.4 Hz, 1H), 6.97 (t, J=7.1 Hz, 1H), 7.02-7.13 (m, 4H), 7.18-7.28 (m, 2H), 7.30-7.40 (m, 2H), 7.49 (d, J=8.4 Hz, 2H), 7.58 (d, J=7.9 Hz, 1H), 7.97 (d, J=8.0 Hz, 1H). $^{13}$C NMR (CD$_3$OD, 75 MHz): δ=25.4, 26.4, 26.5, 29.0, 29.0, 30.4, 36.7, 39.5, 39.7, 42.0, 55.9, 109.9, 111.3, 118.5, 118.9, 120.3, 121.5, 123.8, 123.3, 125.3, 127.7, 127.9, 129.6, 130.2, 134.5, 137.2, 138.3, 170.1, 173.4. FAB-HRMS calculated for [C$_{31}$H$_{36}$N$_5$O$_3$S+H]$^+$: 558.2539; found: 558.2533. HPLC purity: 96%.

Spectral data for 6-(2-mercapto-acetylamino)-hexanoic acid [2'-(2-amino-acetylamino)-biphenyl-4-yl]-amide (10a). $^1$H NMR (DMSO-d$_6$, 400 MHz): S=1.32 (m, 2H), 1.45 (m, 2H), 1.61 (m, 2H), 2.32 (t, J=7.3 Hz, 2H), 3.10 (m, 2H), 3.35 (m, 4H), 3.47 (s, 2H), 7.23-7.37 (m, 7H), 7.70 (d, J=8.5 Hz, 2H), 7.91 (d, J=7.9 Hz, 1H), 8.11 (t, J=5.3 Hz, 1H), 9.77 (s, 1H), 10.00 (s, 1H). $^{13}$C NMR (DMSO-d$_6$, 75 MHz): δ=24.9, 26.1, 28.8, 36.4, 38.2, 42.0, 42.9, 119.1, 123.5, 125.1, 127.7, 129.3, 130.3, 132.6, 133.8, 134.2, 138.8, 167.6, 168.7, 171.3. FAB-HRMS calculated for [C$_{22}$H$_{28}$N$_4$O$_3$S+H]$^+$: 429.1960; found: 429.1953. HPLC purity: 97%.

Spectral data for 6-(2-Mercapto-acetylamino)-hexanoic acid [2'-(2-amino-3-phenyl-propionylamino)-biphenyl-4-yl]-amide (10b). NMR (DMSO-d$_6$, 400 MHz): δ=1.07 (t, J=7.0 Hz, 1H), 1.17 (t, J=7.0 Hz, 1H), 1.31 (m, 2H), 1.44 (m, 2H), 1.59 (m, 2H), 2.31 (m, 2H), 2.85 (m, 1H), 3.07 (m, 4H), 3.48 (br s, 2H), 3.90 (m, 1H), 7.14-7.37 (m, 10H), 7.64 (d, J=8.3 Hz, 2H), 7.77 (d, J=7.7 Hz, 1H), 8.11 (br s, 1H), 9.81 (br s, 1H), 9.98 (s, 1H). $^{13}$C NMR (DMSO-d$_6$, 75 MHz): S=25.2, 26.5, 29.2, 36.8, 38.2, 42.4, 46.1, 55.0, 119.5, 124.9, 125.9, 127.2, 127.8, 128.8, 129.5, 129.8, 130.6, 132.9, 134.2, 135.0, 136.2, 139.1, 168.0, 169.3, 171.7. FAB-HRMS calculated for [C$_{29}$H$_{34}$N$_4$O$_3$S]$^+$: 518.2351; found: 518.2339. HPLC purity: 96%.

Spectral data for pyrrolidine-2-carboxylic acid {4'-[6-(2-mercapto-acetylamino)-hexanoylamino]-biphenyl-2-yl}-amide (10c). $^1$H NMR (DMSO-d$_6$, 400 MHz): δ=1.25-1.70 (m, 8H), 1.78 (m, 1H), 1.96 (m, 1H), 2.23-2.35 (m, 4H), 2.55 (m, 1H), 3.08 (m, 3H), 3.59 (m, 1H), 7.13-7.34 (m, 7H), 730 (d, J=11.2 Hz, 2H), 8.11 (m, 1H), 8.28 (d, J=10.8 Hz, 1H), 10.00 (br s, 1H), 10.13 (br s, 1H). $^{13}$C NMR (DMSO-d$_6$, 75 MHz): δ=25.2, 26.2, 26.5, 29.2, 30.7, 36.8, 42.4, 46.8, 60.9, 119.5, 120.4, 124.1, 128.6, 129.3, 129.8, 130.4, 132.0, 132.6, 135.4, 139.2, 168.0, 171.7, 173.5. FAB-HRMS calculated for [C$_{25}$H$_{32}$N$_4$O$_3$S]$^+$: 468.2195; found: 468.2186. HPLC purity: 98%.

Preparation of 6-(2-mercapto-acetylamino)-hexanoic acid {2'-[2-amino-3-(4-hydroxy-phenyl)-propionylamino]-biphenyl-4-yl}-amide (10e). A suspension of compound 9e (0.050 g, 0.051 mmol) and Pd(OH)$_2$/C (20 wt. %, 0.010 g) in methanol (5 ml) was stirred under hydrogen atmosphere at room temperature for 4 hours. The catalyst was removed by filtration through a pad of celite and the residue was thoroughly washed with MeOH. The solvent was evaporated in vacuo, and the product was subjected to further reaction without additional purification. To a solution of trityl compound (0.030 g, 0.034 mmol) in CH$_2$Cl$_2$ TFA (1 ml) was added. The resulting yellow solution was treated dropwise with triethylsilane until the color disappeared. The mixture was then stirred for 2 hours and the solvent was evaporated in vacuo. The residue was dissolved in EtOAc and consecutively washed with saturated NaHCO$_3$ solution and brine, organic phase was dried over Na$_2$SO$_4$ and evaporated. The crude material was purified by flash chromatography (methanol/ CH$_2$Cl$_2$, 1:10) to give compound 10e (0.012 g, 44% for two steps).
$^1$H NMR (CD$_3$OD, 400 Hz): δ=1.45 (quin, J=8.2 Hz, 2H), 1.59 (quin, J=6.9 Hz, 2H), 1.75 (quin, J=7.4 Hz, 2H), 2.93 (dd, J=5.3 and 13.6 Hz, 1H), 3.14 (s, 2H), 3.23 (t, J=6.9 Hz, 2H), 3.57 (dd, J=5.6 and 7.0 Hz, 1H), 6.74 (d, J=8.3 Hz, 2H), 7.02 (d, J=8.2 Hz, 2H), 7.17 (d, J=8.3 Hz, 2H), 7.20-7.30 (m, 2H), 7.33-7.39 (m, 1H), 7.61 (d, J=8.4 Hz, 2H), 7.96 (d, J=8.0 Hz, 1H). $^{13}$C NMR (CD$_3$OD, 75 MHz): δ=25.4, 26.4, 26.5, 27.2, 29.0, 29.0, 36.8, 39.5, 39.7, 42.0, 56.9, 115.4, 120.3, 123.4, 125.4, 127.9, 128.1, 129.7, 130.3, 130.5, 134.3, 134.4, 134.7, 138.4, 156.4, 170.1, 173.5, 174.3. FAB-HRMS calculated for [C$_{29}$H$_{34}$N$_4$O$_4$S+H]$^+$: 535.2379; found: 535.2330. HPLC purity: 97%.

Example Three

General Procedure for Phenylthiazole Octanedioic Acid Hydroxyamides (14-23)

The following method represents a typical procedure for synthesis of the octanedioic acid hydroxyamide-based ligands.

Preparation of octanedioic acid [4-(3-Nitro-phenyl)-thiazol-2-yl]-amide methyl ester (14). A stirring solution of 4-(3-nitrophenyl)-thiazol-2-ylamine (11) (2.21 g, 10 mmol) and suberic acid monomethyl ester (13) (1.88 g, 10 mmol) in dry pyridine (20 ml) was cooled to −15° C. and POCl$_3$ (1.2 ml, 13 mmol) was added dropwise over 30 minutes. After stirring for another 1 hour at same temperature, the reaction mixture was diluted with EtOAc and washed thoroughly with 1N HCl solution and brine. The organic phase was dried over Na$_2$SO$_4$. The solvent was removed by rotary evaporation. The crude solid was washed with EtOAc to give compound 14 (2.40 g, 61.5%). $^1$H NMR (400 MHz, DMSO-d$_6$) δ12.3 (1H, s), 8.74 (1H, d, J=1.4 Hz), 8.35 (1H, d, J=7.1 Hz), 8.18 (1H, d, J=7.8 Hz), 7.93 (1H, s), 7.74 (1H, t, J=7.9 Hz), 3.58 (3H, s), 2.46 (2H, t, J=7.5 Hz), 2.30 (2H, t, J=7.3 Hz), 1.61 (2H, t, J=6.5 Hz), 1.53 (2H, t, J=6.8 Hz), 1.30 (4H, brs). $^{13}$C NMR (100 MHz, DMSO-d$_6$) δ172.1, 158.8, 148.7, 146.7, 136.2, 132.1, 130.8, 122.7, 120.5, 110.8, 51.6, 35.2, 33.6, 28.6, 28.5, 24.8, 24.6.

Preparation of octanedioic acid benzyloxy-amide [4-(2-nitro-phenyl)-thiazol-2-yl]-amide (15). Compound 15 was prepared using the methodology described for the preparation of compound 14, by substituting 4-(3-nitrophenyl)-thiazol-2-ylamine with 4-(2-nitrophenyl)-2-thiazolamine (12) and using of compound 5 instead of compound 13. $^1$H NMR (400 MHz, DMSO-d$_6$) δ (ppm). 12.14 (1H, s), 10.93 (1H, s); 7:88 (1H; d, J=7.4 Hz), 7.77 (1H, t, J=7.0 Hz), 7.72 (1H, d, J=7.4 Hz), 7.60 (1H, t, J=7.0 Hz), 7.51 (1H, s), 7.38-7.33 (5H, m), 4.78 (2H, s), 2.44 (2H, t, J=7.3 Hz), 1.94 (2H, t, J=7.3), 1.58 (2H, m), 1.49 (2H, m), 1.30-1.18 (4H, m).

Preparation of octanedioic acid hydroxyamide [4-(2-amino-phenyl)-thiazol-2-yl]-amide (16). To a mixture of compound 15 (0.040 g, 0.083 mmol) in methanol (2 ml) was added 1 ml of concentrated HCl. The suspension was cooled to 0° C. Then SnCl$_2$ (0.094 g, 0.49 mmol) was added and the reaction mixture was stirred overnight at room temperature. The mixture was then diluted with 5 ml of water, adjusted to pH 10 with 5N NaOH and extracted with ethyl acetate (10 mL×3). The combined organic layers were washed with water, dried over K$_2$CO$_3$ and concentrated in vacuo. The crude product was purified by reverse phase HPLC to afford Octanedioic acid hydroxyamide [4-(2-amino-phenyl)-thiazol-2-yl]-amide 16 (0.016 g, 53% yield). NMR (400 MHz, DMSO-d$_6$ cont 5% TFA) δ (ppm) 12.13 (1H, s), 7.56 (1H, d, J=7.0 Hz), 7.40 (1H, s), 7.09 (1H, t, J=7.0 Hz), 6.83 (1H, d, J=7.0 Hz), 6.72 (1H, m), 3.75-3.39 (4H, brs), 2.44 (2H, t, J=7.3 Hz), 2.29 (2H, t, J=7.3), 1.61 (2H, m), 1.51 (2H, m), 1.30 (4H, m).

Preparation of octanedioic acid hydroxyamide [4-(2-nitrophenyl)-thiazol-2-yl]-amide (17). A mixture of compound 15 (0.040 g, 0.083 mmol) in methylene chloride (1 mL) was cooled to −30° C. while boron tribromide (0.18 ml) 1M in methylene chloride was added dropwise. After stirring at room temperature for 2 hours, the mixture was cooled to 0° C. and quenched with saturated sodium bicarbonate. The reaction mixture was diluted with ethyl acetate and washed sequentially with saturated NaHCO$_3$, and brine. The organic layer was dried over sodium sulfate and concentrated in vacuo to provide a crude residue which was purified by reverse phase HPLC to afford octanedioic acid hydroxyamide [4-(2-nitro-phenyl)-thiazol-2-yl]-amide 17 (0.018 g, 55% yield).

Preparation of octanedioic acid [4-(3-Nitro-phenyl)-thiazol-2-yl]-amide (18). To a solution of compound 14 (0.391 g, 1.0 mmol) in a mixture of MeOH (10 ml) and water (10 ml) was added LiOH—H$_2$O (0.839 g, 20.0 mmol), and the mixture was stirred at room temperature for 3 hour. Then the reaction mixture was acidified with 1N HCl dropwise to pH 5 and extracted with EtOAc. The organic layer was washed with water and saturated brine and dried over Na$_2$SO$_4$. The solvent was evaporated to give compound 18 (0.322 g, 85.6%). $^1$H NMR (300 MHz, DMSO-d$_6$) δ12.3 (1H, s), 8.72 (1H, s), 8.33 (1H, d, J=7.6 Hz), 8.16 (1H, dd, J=7.9, 2.8 Hz), 7.91 (1H, s), 7.72 (1H, t, J=8.0 Hz), 2.45 (2H, t, J=6.5 Hz), 2.19 (2H, t, J=5.7 Hz), 1.60 (2H, brs), 1.49 (2H, t, J=6.3 Hz), 1.30-1.18 (4H, m). $^{13}$C NMR (75 MHz, DMSO-d$_6$) M75.3, 172.5, 159.2, 149.1, 147.1, 136.6, 132.5, 131.2, 123.0, 120.9, 111.2, 35.7, 34.4, 31.2, 29.1, 25.3, 25.1.

Preparation of octanedioic acid hydroxyamide [4-(3-Nitro-phenyl)-thiazol-2-yl]-amide (19). To a solution of compound 18 (0.100 g, 0.26 mmol) in dry THF was added Et$_3$N (0.18 ml, 1.3 mmol) under Nitrogen, and the solution was stirred for 5 minutes. The solution was cooled to −15° C. and stirred for another 5 minutes. Then, iso-butyl chloroformate (67 μl 0.52 mmol) was added dropwise and the mixture was stirred for 15 minutes. The solid was filtered off. The filtrate was cooled to 0° C. and NH$_2$OH 50% water solution (1 ml) was added for 10 minutes. The reaction mixture was diluted with EtOAc and washed with saturated aqueous NH4Cl and brine and then dried over Na$_2$SO$_4$. The solvent was removed by rotary evaporation. The crude solid was washed with EtOAc and MeOH to give compound 19 (0.027 g, 26.4%). $^1$H NMR (300 MHz, DMSO-d$_6$) δ 12.3 (1H, s), 10.3 (1H, s), 8.72 (1H, s), 8.67 (1H, brs), 8.34 (1H, d, J=7.7 Hz), 8.17 (1H, dd, J=8.1, 1.5 Hz), 7.91 (1H, s), 7.73 (1H, t, J=7.9 Hz), 2.45 (2H, t, J=7.2 Hz), 1.94 (2H, t, J=7.2 Hz), 1.60 (2H, brs), 1.50 (2H, t, J=6.1 Hz), 1.50-1.35 (4H, m). $^1$H NMR (100 MHz, DMSO-d6) δ 172.1, 169.5, 158.8, 148.7, 146.7, 136.2, 132.1, 130.8, 122.7, 120.4, 110.8, 35.3, 32.6, 28.7, 25.4, 24.9.

Preparation of octanedioic acid [4-(3-Amino-phenyl)-thiazol-2-yl]-amide methyl ester (20). A suspension of compound 14 (0.391 g, 1 mmol) and Pd/C (10 wt. %, 50 mg) in EtOH and AcOH (20 ml+1 ml) was reacted under hydrogen atmosphere at 50° C. for 2 hours. The catalyst was removed by filtration through a pad of Celite. After removal of the solvent in vacuo, the crude material was dissolved in EtOAc and washed with NaHCO$_3$ solution and brine and dried over Na$_2$SO$_4$. The solvent was removed by rotary evaporation. The crude solid was purified by flash chromatography (EtOAc/ hexane, 2:1) to give compound 20 (0.261 g, 72.4%). $^1$H NMR (300 MHz, CDCl$_3$) δ 11.2 (1H, s), 7.22 (1H, s), 7.20 (1H, s), 7.16 (1H, brs), 7.10 (1H, s), 6.70-6.66 (1H, m), 3.69 (3H, s), 2.28 (2H, t, J=7.4 Hz), 2.06 (2H, dd, J=7.3, 4.7 Hz), 1.61-1.45 (4H, m), 1.22-1.08 (4H, m). $^{13}$C NMR (75 MHz, CDCl$_3$) δ 174.6, 171.8, 159.6, 150.1, 147.3, 135.7, 130.2, 116.9, 115.3, 113.0, 108.1, 51.9, 36.1, 34.3, 29.07, 29.01, 25.09, 25.00, 21.4.

Preparation of octanedioic acid [4-(3-Amino-phenyl)-thiazol-2-yl]-amide (21). Compound 21 was prepared using the methodology described for the preparation of compound 18, by substituting compound 14 with compound 20. Yield (0.276 g, 79.8%). $^1$H NMR (300 MHz, CDCl$_3$) δ 7.21 (1H, t, J=7.7 Hz), 7.07 (1H, d, J=8.2 Hz), 6.99 (2H, s), 6.69 (1H, d, J=7.8 Hz), 2.49 (2H, t, J=7.3 Hz), 2.40 (2H, t, J=7.1 Hz), 1.78 (2H, brs), 1.69 (2H, t, J=6.7 Hz), 1.50-1.35 (4H, m). $^{13}$C NMR (75 MHz, CDCl$_3$) δ 179.6, 172.2, 160.8, 149.7, 147.1, 135.0, 130.2, 117.3, 115.6, 113.5, 108.1, 36.7, 34.4, 29.1, 28.9, 25.5, 24.9.

Preparation of {3-[2-(7-hydroxycarbamoyl-heptanoylamino)-thiazol-4-yl]-phenyl}-carbamic acid ethyl ester (22). Compound 22 was prepared using the methodology described for the preparation of compound 19, by substituting compound 18 with compound 21. The crude material was purified by preparative HPLC to give product (0.130 g, 11.5%). NMR (300 MHz, DMSO-d6) δ 12.2 (1H, s), 10.3 (1H, s), 9.68 (1H, s), 8.11 (1H, s), 7.47 (2H, brs), 7.31 (2H, brs), 4.13 (2H, q, J=7.1 Hz), 2.44 (2H, t, 5=7.3 Hz), 1.93 (2H, t, J=6.8 Hz), 1.59 (2H, m), 1.48 (2H, m), 1.27-1.23 (5H, m). $^1$H NMR. (100 MHz, DMSO-d6) δ 172.0, 169.5, 158.3, 154.0, 149.2, 140.0, 135.3, 129.4, 120.3, 118.2, 116.0, 108.3, 60.6, 35.2, 32.6, 28.7, 25.4, 25.0, 14.9.

Preparation of octanedioic acid hydroxyamide [4-(3-amino-phenyl)-thiazol-2-yl]-amide (23). To a solution of hydroxylamine hydrochloride (0.958 g, 13.8 mmol) in MeOH-KOH (0.772 g, 13.8 mmol) was added at 40° C. for 10 minutes. The reaction mixture was cooled to 0° C. and filtered. Compound 20 (0.250 g, 0.69 mmol) was added to the filtrate followed by KOH (50 mg, 0.89 mmol) at room temperature. After 2 hours, water (20 ml) was added, followed by 1 N HCl until pH reached 6.5. The reaction mixture was extracted with EtOAc, and organic layer was washed with brine, dried over Na$_2$SO$_4$ and filtered. The solvent was removed by rotary evaporation. The crude solid was purified by preparative HPLC to give compound 23 (0.110 g, 43.9%). $^1$H NMR (300 MHz, CD$_3$OD) δ 7.98 (1H, d, J=7.8 Hz), 7.90 (1H, s), 7.55 (1H, t, J=7.8 Hz), 7.51 (1H, s), 7.29 (1H, dd, J=7.8, 1.2 Hz), 2.51 (2H, t, J=7.2 Hz), 2.11 (2H, t, J=7.2 Hz), 1.74 (2H, t, J=7.0 Hz), 1.65 (2H, t, J=7.0 Hz), 1.50-1.35 (4H, m). $^{13}$C NMR (100 MHz, CD$_3$OD) δ 172.1, 158.0, 147.4, 136.3, 129.7, 125.1, 120.8, 119.2, 108.5, 34.6, 28.0, 27.9, 24.7, 24.3.

Example Four

Inhibition of Malaria

Compounds (Ab-b/7f, Ab-t/26, yc-84/25, yc-90/19, and yc-88/23) were dissolved in about 50 μL DMSO to make 1 mM solutions. These solutions were then diluted to a concentration of about 500 nM with CM; parasites (3D7, 7G8, or DD2) were incubated with the resulting solutions. Parasitemia growth inhibition was measured by FACS. Results of these experiments are shown in FIGS. 14-18.

INCORPORATION BY REFERENCE

All of the U.S. patents and U.S. published patent applications cited herein are hereby incorporated by reference. In addition, U.S. Patent Application 2006/047123, U.S. Patent Application 2002/177594, and International Patent Application WO 2002/026696 are hereby incorporated by reference. Further, WO 2004/067480 A2 (Oxford Glycosciences (UK) Ltd), WO 2004/009536 A1 (4SC AG and G2M Cancer Drugs AG), WO 2004/046094 A1 (Queen Mary & Westfield College, University College London and Barts and the London NHS Trust), WO 2004/113336 A1 (Chroma Therapeutics, Ltd.), WO 2004/072047 A1 (Fujizawa Pharmaceutical Co. Ltd.), WO 2004/089293 A2 (Memorial Sloan-Kettering Cancer Center), WO 2004/071401 A2 (Fujizawa Pharmaceutical Co. Ltd.), WO 2004/063169 A1 (Fujizawa Pharmaceutical Co. Ltd.), US 2004/0229889 A1 (Fujizawa Pharmaceutical Co. Ltd.), WO 2004/082638 A2 (Syrrx, Inc), US 2004/0254220 A1 (Syrrx), WO 2004/063146 A1 (Italfarmaco SPA), WO 2004/092115 A2 (Axys Pharmaceuticals Inc.), WO 2004/065354 A1 (Topotarget UK Ltd.), WO 2004/013130 A1 (Argenta Discovery Ltd.), US 2004/0122079 A1 (Hoffmann-La Roche AG), WO 2004/035525 A1 (MethylGene, Inc.), U.S. Pat. No. 6,897,220 (MethylGene, Inc.), WO 2004/052838 A1 (Hoffmann-La Roche AG), WO 2004/087693 A1 (Hoffmann-La Roche AG), WO 2004/069133 A2 (Hoffmann-La Roche AG), US 2004/0162317 A1 (Hoffmann-La Roche AG), WO 2004/069803 A2 (Hoffmann-La Roche AG), WO 2004/071400 A2 (Shenzhen Chipscreen Biosciences Ltd.), US 2004/0224991 A1 (Shenzhen Chip-Screen Biosciences, Ltd.), WO 2004/110418 A2 (Kalypsis, Inc.), and US 2004/0023944 A1 (Beacon Laboratories, Inc.) are hereby encorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound, or a pharmaceutically acceptable salt thereof, selected from the group consisting of

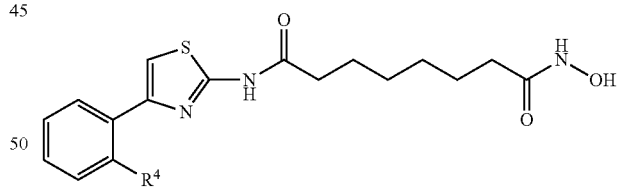

and

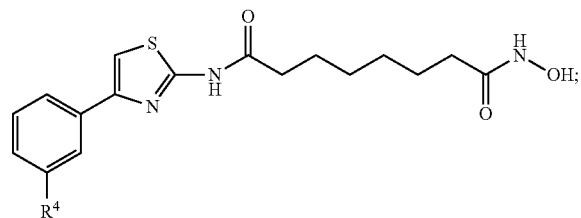

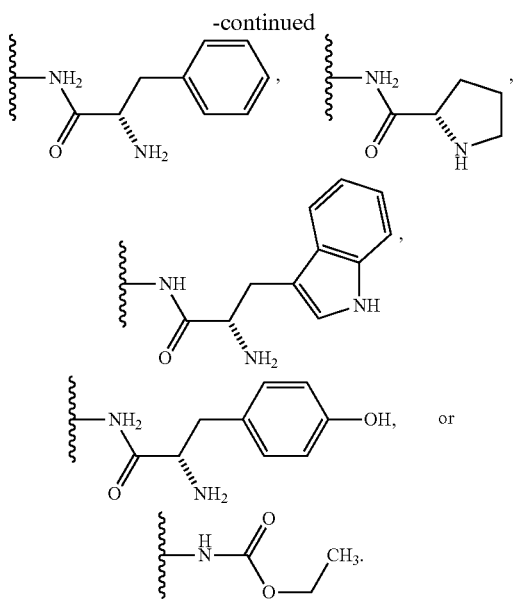

2. A method of treating malaria, comprising the step of: administering to a subject in need thereof a therapeutically effective amount of a compound, or a pharmaceutically acceptable salt thereof, selected from the group consisting of

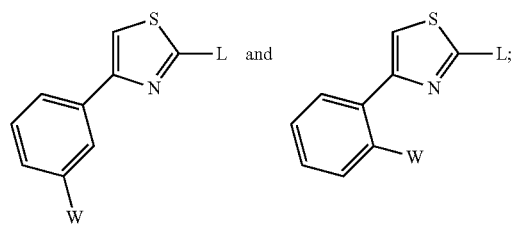

wherein
W is halo, azido, alkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, amino, alkylamino, arylamino, acylamino, heteroarylamino, nitro, sulfhydryl, imino, amido, phosphonate, phosphinate, acyl, carboxyl, oxycarbonyl, aryloxy, silyl, thioether, sulfo, sulfonate, sulfonyl, sulfonamido, formyl, cyano, or isocyano;
L is -($Q^1$)-N(H)C(=O)-($Q^2$)-Z;
$Q^1$ is $C_{1-3}$alkylene or a bond;
$Q^2$ is $C_{1-10}$alkylene;
Z is

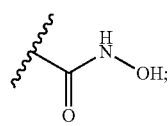 [SMILES: *C(=O)NO]

and
the stereochemical configuration at any stereocenter is R, S, or a mixture of these configurations.

3. The method of claim 2, further comprising co-administering to said subject an antimalarial compound selected from the group consisting of aryl amino alcohols, cinchona alkaloids, 4-aminoquinolines, type 1 or type 2 folate synthesis inhibitors, 8-aminoquinolines, antimicrobials, peroxides, naphthoquinones and iron-chelating agents.

4. The method of claim 2, further comprising co-administering to said subject an antimalarial compound selected from the group consisting of quinine, quinidine, mefloquine, halofantrine, chloroquine, amodiaquine, proguanil, chloroproguanil, pyrimethamine, primaquine, 8-[(4-amino-1-methylbutyl)amino]-2,6-dimethoxy-4-methyl-5-[(3-trifluoromethyl)phenoxy]quinoline succinate (WR238,605), tetracycline, doxycycline, clindamycin, azithromycin, fluoroquinolones, artemether, arteether, artesunate, artelinic acid, atovaquone, and desferrioxamine.

5. The method of claim 2, further comprising co-administering chloroquine to said subject.

6. The method of claim 2, wherein said compound is

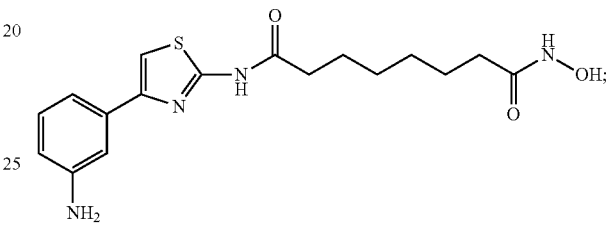

and further comprising co-administering chloroquine to said subject.

7. The compound of claim 1, wherein the compound is

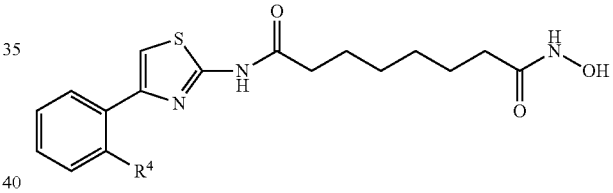

or a pharmaceutically acceptable salt thereof.

8. The compound of claim 1, wherein the compound is

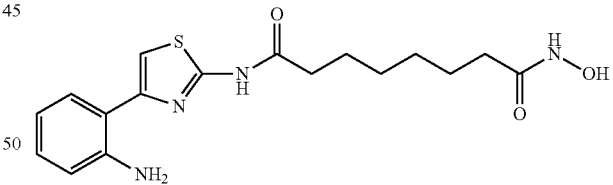

or a pharmaceutically acceptable salt thereof.

9. The compound of claim 1, wherein the compound is

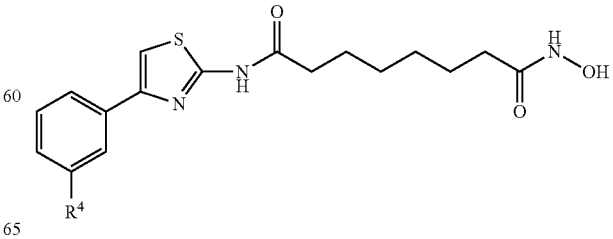

or a pharmaceutically acceptable salt thereof.

10. The compound of claim 1, wherein the compound is
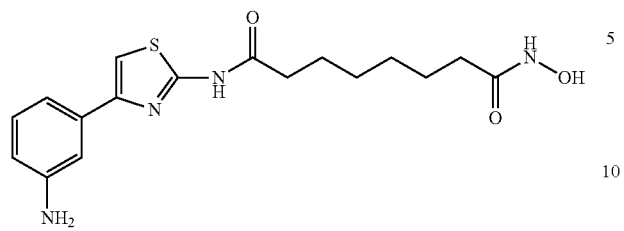
or a pharmaceutically acceptable salt thereof.

UNITED STATES PATENT AND TRADEMARK OFFICE
CERTIFICATE OF CORRECTION

PATENT NO. : 8,653,278 B2
APPLICATION NO. : 12/375348
DATED : February 18, 2014
INVENTOR(S) : Alan P. Kozikowski et al.

It is certified that error appears in the above-identified patent and that said Letters Patent is hereby corrected as shown below:

In the Claims:

Column 86, claim 1, lines 60-65, replace

"wherein R$^4$ is 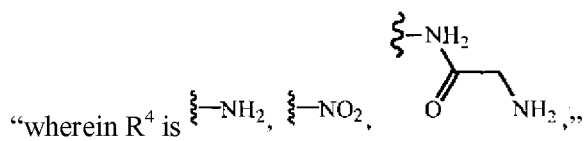,"

with

-- wherein R$^4$ is 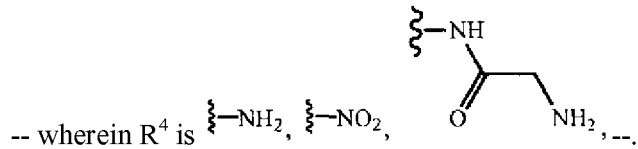,--.

Column 87, claim 1, lines 1-5, replace

" 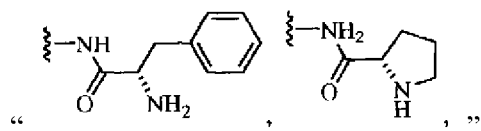, "

with

-- 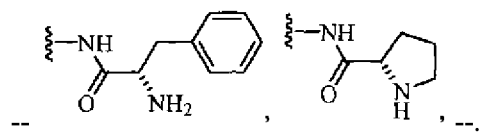,--.

Signed and Sealed this
Twenty-seventh Day of May, 2014

Michelle K. Lee
*Deputy Director of the United States Patent and Trademark Office*

CERTIFICATE OF CORRECTION (continued)

Column 87, claim 1, lines 15-19, replace

" 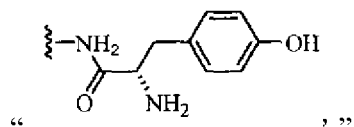 , "

with

-- 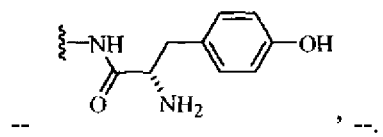 , --.

Column 87, claim 2, line 48, replace

"aryloxy,"

with

-- acyloxy, --.

UNITED STATES PATENT AND TRADEMARK OFFICE
CERTIFICATE OF CORRECTION

PATENT NO. : 8,653,278 B2
APPLICATION NO. : 12/375348
DATED : February 18, 2014
INVENTOR(S) : Alan P. Kozikowski et al.

It is certified that error appears in the above-identified patent and that said Letters Patent is hereby corrected as shown below:

In the Specification

At Column 1, Line number 16-20:
"This invention was made with support provided by the Department of Defense (Grant No. PC030471), and the National Cancer Institute (Grant No. P02 CA74175); therefore, the government has certain rights in the invention."

Should read:
--This invention was made with government support under grant number CA074175 awarded by the National Institutes of Health and grant number W81XWH-04-1-0170 awarded by the Department of Defense. The government has certain rights in the invention.--

Signed and Sealed this
Tenth Day of October, 2023

Katherine Kelly Vidal
*Director of the United States Patent and Trademark Office*